US007670802B2

(12) United States Patent
Proudfoot et al.

(10) Patent No.: US 7,670,802 B2
(45) Date of Patent: Mar. 2, 2010

(54) **CXC-CHEMOKINE ANTAGONISTS ISOLATED FROM *RHIPICEPHALUS SANGUINEUS***

(75) Inventors: Amanda Proudfoot, Chens sur Leman (FR); Christine Power, Thoiry (FR)

(73) Assignee: Merck Serono SA, Coinsins, Vaud (CH)

( * ) Notice: Subject to any disclaimer, the term of this patent is extended or adjusted under 35 U.S.C. 154(b) by 0 days.

(21) Appl. No.: 12/067,221

(22) PCT Filed: Oct. 30, 2006

(86) PCT No.: PCT/EP2006/067939

§ 371 (c)(1),
(2), (4) Date: Mar. 18, 2008

(87) PCT Pub. No.: WO2007/051781

PCT Pub. Date: May 10, 2007

(65) Prior Publication Data

US 2008/0227711 A1 Sep. 18, 2008

Related U.S. Application Data

(60) Provisional application No. 60/733,547, filed on Nov. 4, 2005.

(30) Foreign Application Priority Data

Oct. 31, 2005 (EP) .................................. 05110205

(51) Int. Cl.
*C12N 15/62* (2006.01)
*C12N 15/63* (2006.01)
*A61K 38/00* (2006.01)
*C07K 14/00* (2006.01)
*C07H 21/04* (2006.01)

(52) U.S. Cl. ................ 435/69.1; 435/252.3; 435/320.1; 435/69.5; 435/71.1; 514/2; 514/12; 530/350; 536/23.4; 536/23.5

(58) Field of Classification Search ........................ None
See application file for complete search history.

(56) References Cited

U.S. PATENT DOCUMENTS 7,393,660 B2 * 7/2008 Power et al. ................ 435/69.1
2006/0228327 A1 10/2006 Proudfoot et al.
2007/0224125 A1 9/2007 Power et al.

FOREIGN PATENT DOCUMENTS

WO WO 00/27873 5/2000
WO WO 01/58941 A1 8/2001
WO WO 2005/063812 A2 7/2005

OTHER PUBLICATIONS

Alarcon-Chaidez, F. J. et al. "Characterization of a recombinant immunomodulatory protein from the salivary glands of *Dermacentor andersoni*" *Parasite Immunology*, 2003, pp. 69-77, vol. 25.

Aljamali, M.N. et al. "RNA interference in ticks: a study using histamine binding protein dsRNA in the female tick *Amblyomma americanum*" *Insect Molecular Biology*, 2003, pp. 299-305, vol. 12, No. 3.
Baggiolini, M. "Chemokines in pathology and medicine" *Journal of internal Medicine*, 2001, pp. 91-104, vol. 250.
Baggilolini, M. et al. "Human Chemokines: An Update" *Annu. Rev. Immunol*, 1997, pp. 675-705, vol. 15.
Beck, C. G. et al. "The Viral CC Chemokine-binding Protein vCCI Inhibits Monocyte Chemoattractant Protein-1 Activity by Masking Its CCR2B-binding Site" *The Journal of Biological Chemistry*, Nov. 16, 2001, pp. 43270-43276, vol. 276, No. 46.
Ben-Bassat, A. "Methods for Removing N-Terminal Methionine from Recombinant Proteins" *Bioprocess Technol*.1991, pp. 147-159, vol. 12.
Brown, A. et al. "The Total Chemical Synthesis of Monocyte Chemotactic Protein-1 (MCP-1)" *Journal of Peptide Science*, 1996, pp. 40-46, vol. 2.
Burns, J. et al. "Comprehensive Mapping of Poxvirus vCCI Chemokine-binding Protein" *The Journal of Biological Chemistry*, Jan. 25, 2002, pp. 2785-2789, vol. 277, No. 4.
Bursill, C.A. et al. "Broad-Spectrum CC-Chemokine Blockade by Gene Transfer Inhibits Macrophage Recruitment and Atherosclerotic Plaque Formation in Apolipoprotein E-Knockout Mice" *Circulation*, 2004, pp. 2460-2466, vol. 110.
Chuang, V. T. et al. "Pharmaceutical Strategies Utilizing Recombinant Human Serum Albumin" *Pharmaceutical Research*, May 2002, pp. 569-577, vol. 19, No. 5.
Clackson, T. et al. "Making antibody fragments using phage display libraries" *Nature*, Aug. 15, 1991, pp. 624-628, vol. 352.
Cleland, J. et al. "Emerging protein delivery methods" *Current Opinion in Biotechnology*, 2001, pp. 212-219, vol. 12.
Coleman, R. A. et al. "Use of human tissue in ADME and safety profiling of development candidates" *Drug Discovery Today*, Nov. 21, 2001, pp. 1116-1126, vol. 6, No. 21.
Doughtery, D. A. "Unnatural amino acids as probes of protein structure and function" *Current Opinion in Chemical Biology*, 2000, pp. 645-652, vol. 4.
Ferreira, B. R. et al. "Saliva of *Rhipicephalus sanguineus* tick impairs T cell proliferation and IFN-γ-induced macrophage microbicidal activity" *Veterinary Immunology and Immunopatholgy*, Mar. 26, 1998, pp. 279-293, vol. 64.
Gendel, S. M. "Sequence Analysis for Assessing Potential Allergenicity" *Ann. N.Y. Acad. Sci.*, 2002, pp. 87-98, vol. 964.
Gillespie, R. D. et al. "Identification of an IL-2 Binding Protein in the Saliva of the Lyme Disease Vector Tick, *Ixodes scapularis*" *The Journal of Immunology*, 2001, pp. 4319-4326, vol. 166.
Goding, J.W. "3. Production of Monoclonal Antibodies" In: *Monoclonal Antibodies: Principals and Practice*, 1986, pp. 59-103, Academic Press, Harcourt Javanovich, publisher.
Golebiowski, A. et al. "High-throughput organic synthesis of peptide mimetics" *Current Opinion in Drug Discovery & Development*, 2001, pp. 428-434, vol. 4.

(Continued)

*Primary Examiner*—Christine J Saoud
(74) *Attorney, Agent, or Firm*—Saliwanchik, Lloyd & Saliwanchik

(57) ABSTRACT

A novel CXC-chemokine binding protein is cloned from the salivary glands of *Rhipicephalus sanguineus*. Compounds prepared in accordance with the present invention can be used as anti-inflammatory and immuno-modulatory compounds and in the treatment or prevention of CXC-chemokine-related diseases.

23 Claims, 22 Drawing Sheets

OTHER PUBLICATIONS

Graslund, T. et al. "Production of a Thermostable DNA Polymerase by Site-Specific Cleavage of a Heat-Eluded Affinity Fusion Protein" *Protein Expression and Purification*, 1997, pp. 125-132, vol. 9.

Greenwald, R.B. et al. "Effective drug delivery by PEGylated drug conjugates" *Advanced Drug Delivery Reviews*, 2003, pp. 217-250, vol. 55.

Hajnicka, V. et al. "Anti-interleukin-8 activity of tick salivary gland extracts" *Parasite Immunology*, 2001, pp. 483-489, vol. 23.

Hajnicka, V. et al. "Manipulation of host cytokine network by ticks: a potential gateway for pathogen transmission" *Parasitology*, 2005, pp. 333-342, vol. 130.

Harris, J. M. et al. "Effect of Pegylation on Pharmaceuticals" *Nature Review Drug Discovery*, Mar. 2003, pp. 214-221, vol. 2.

Hill, C. A. et al. "A method for extraction and analysis of high quality genomic DNA from ixodid ticks" *Medical and Veterinary Entomology*, 2003, pp. 224-227, vol. 17.

Holt, L. J. et al. "Domain antibodies: proteins for therapy" *TRENDS in Biotechnology*, Nov. 2003, pp. 484-490, vol. 21, No. 11.

Hoogenboom, H. R. et al. "By-passing Immunization Human Antibodies from Synthetic Repertoires of Germline V Gene Segments Rearranged in Vitro" *J. Mol. Biol*, 1992, pp. 381-388, vol. 227.

Hruby, V. J. et al. "Conformational and Topographical Considerations in Designing Agonist Peptidomimetics from Peptide Leads" *Current Medicinal Chemistry*, 2000, pp. 945-970, vol. 7.

Jensen, K. K. et al. "Disruption of CCL21-Induced Chemotaxis In Vitro and In Vivo by M3, a Chemokine-Binding Protein Encoded by Murine Gammaherpesvirus 68" *Journal of Virology*, Jan. 2003, pp. 624-630, vol. 77.

Jones, P. T. et al. "Replacing the complementarity- determining regions in a human antibody with those from a mouse" *Nature*, May 29, 1986, pp. 522-525, vol. 321.

Kipriyanov, S. M. et al. "Generation and Production of Engineered Antibodies" *Molecular Biotechnology*, 2004, pp. 39-60, vol. 26.

Kocakova, P. et al. "Effect of fast protein liquid chromatography fractionated salivary gland extracts from different ixodid tick species on interleukin-8 binding to its cell receptors" *Folia Parasitologica*, 2003, pp. 79-84, vol. 50.

Kohler, et al. "Continuous cultures of fused cells secreting antibody of predefined specificity" *Nature*, Aug. 7, 1975, p. 495, vol. 256.

Li, A.P. "Screening for human ADME/Tox drug properties in drug discovery" *Drug Discovery Today*, Apr. 2001, pp. 357-366, vol. 6, No. 7.

Luo, Y., et al. "Novel biomaterials for drug delivery" *Expert Opinion Ther. Patents*, 2001, pp. 1395-1410, vol. 11. No. 9.

Madden, R. D. et al. "A proteomics approach to characterizing tick salivary secretions" *Experimental and Applied Acarology*, 2003, pp. 77-87, vol. 28.

Marks, J. D. et al. "By-passing Immunization Human Antibodies from V-gene Libraries Displayed on Phage" *J. Mol. Biol.*, 1991, pp. 581-597, vol. 222.

Marshall, S. A. et al. "Rational design and engineering of therapeutic proteins" *Drug Discovery Today*, Mar. 2003, pp. 212-221, vol. 8, No. 5.

Mulenga, A. et al. "Issues in tick vaccine development: identification and characterization of potential candidate vaccine antigens" *Microbes and Infection*, 2000, pp. 1353-1361, vol. 2.

Murrell, A. et al. "A Total-Evidence Phylogeny of Ticks Provides Insights into the Evolution of Life Cycles and Biogeography" *Molecular Phylogenetics and Evolution*, Nov. 2001, pp. 244-258, vol. 21, No. 2.

Murphy, L. R. et al. "Simplified amino acid alphabets for protein fold recognition and implications for folding" *Protein Engineering*, 2000, pp. 149-152, vol. 13, No. 3.

Nilsson, J. et al. "Affinity Fusion Strategies for Detection, Purification and Immobilization of Recombinant Proteins" *Protein Expression and Purification*, 1997, pp. 1-16, vol. 11.

Pearson, W. R. "Flexible Sequence Similarity Searching with the FASTA3 Program Package" *Methods in Molecular Biology*, 2000, pp. 185-219, vol. 132.

Pillai, O. et al. "Polymers in drug delivery" *Current Opinion in Chemical Biology*, 2001, pp. 447-451, vol. 5.

Presta, L. "Antibody engineering for therapeutics" *Current Opinion in Structural Biology*, 2003, pp. 519-525, vol. 13.

Pyo, R. et al. "Inhibition of Intimal Hyperplasia in Transgenic Mice Conditionally Expressing the Chemokine-Binding Protein M3" *American Journal of Pathology*, Jun. 2004, pp. 2289-2297, vol. 164, No. 6.

Rapoport, T.A., et al. "Protein transport across the eukaryotic endoplasmic reticulum and bacterial inner membranes" *Annual Review Biochemistry*, 1996, pp. 271-303, vol. 65.

Rogov, S. L. et al. "A numerical measure of amino acid residues similarity based on the analysis of their surroundings in natural protein sequences" *Protein Engineering*, 2001, pp. 459-463, vol. 14, No. 7.

Scatchard, G. "The Attractions of Proteins for Small Molecules and Ions" *Ann NY Acad. Sci.*, 1949, pp. 660-672, vol. 51.

Schellekens, H. "Bioequivalence and the Immunogenicity of Biopharmaceuticals" *Nature Review Drug Discovery*, Jun. 2002, pp. 457-462, vol. 1.

Seet, B.T. et al. "Molecular determinants for CC-chemokine recognition by a poxvirus CC-chemokine inhibitor" *Proc. Natl. Acad. Science USA*, Jul. 31, 2001, pp. 9008-9013, vol. 98, No. 16.

Ullmann, A. J. et al. "A preliminary linkage map of the tick, *Ixodes scapularis*" *Experimental and Applied Acarology*, 2002, pp. 107-126, vol. 28.

Vaitukaitis, J. et al. "A method for producing specific antisera with small doses of Immunogen" *J. Clin. Endocr*, 1971, p. 988, vol. 33.

Valenzuela, J.G. et al. "Editorial: Exploring the messages of the salivary glands of *Ixodes Ricinus*" *Am. J. Trop. Med. Hyg.*, 2002, pp. 223-224, vol. 66, No. 3.

Van Valkenburgh, H. A. et al. "Coexpression of Proteins with Methionine Aminopeptidase and/or N-Myristoyltransferase in *Escherichia coli* to Increase Acylation and Homogeneity of Protein Preparations" *Methods in Enzymology*, 2002, pp. 186-193, vol. 344.

Vasserot, A.P. et al. "Optimization of protein therapeutics by directed evolution" *Drug Discovery Today*, Feb. 2003, pp. 118-126, vol. 8, No. 3.

Villain, M. et al. "Covalent capture: a new tool for the purification of synthetic and recombinant polypeptides" *Chemistry & Biology*, 2001, pp. 673-679, vol. 8.

Wang, H. et al. "Molecular individuality: polymorphism of salivary gland proteins in three species of ixodid tick" *Experimental and Applied Acarolgy*, 1999, pp. 969-975, vol. 23.

Ward, E.S., et al. "Binding activities of a repertoire of single immunoglobulin variable domains secreted from *Escherichia coli*" *Nature*, Oct. 12, 1989, p. 544, vol. 341.

Webb, L. M. et al. "The gammaherpesvirus chemokine binding protein can inhibit the interaction of chemokines with glycosaminoglycans" *The FASEB Journal*, Jan. 20, 2004, pp. 571-573, vol. 18.

* cited by examiner

Fig. 1

```
  1  CGGCCGGGGG AGCAAACATC GCAGTTGCTG AACGGTTGCG CTCGTCTTAT AAGCAGGAGT
 61  AATACCGGTG ATCAGAGGGC GTATAACGGT AAGGAAGGTA GTGAGCTTAT TCCTTTGTAC

121  GAGACATTGT GCATCGCAGG T ATG GTG TCG ATG AAG ACA ACG CAT CAT GTC
                            Met Val Ser Met Lys Thr Thr His His Val

172  CTA TTT CTG CTA GTT GCT TTG GAA TCA ATG CGA CCC TAC ACG ACT GCT
     Leu Phe Leu Leu Val Ala Leu Glu Ser Met Arg Pro Tyr Thr Thr Ala

220  CTT GTT TCA ACT ATT GAG TCA AGA ACG AGT GGA GAT GGC GCA GAT AAC
     Leu Val Ser Thr Ile Glu Ser Arg Thr Ser Gly Asp Gly Ala Asp Asn

268  TTT GAT GTA GTA TCT TGT AAT AAG AAT TGC ACT TCA GGT CAA AAC GAA
     Phe Asp Val Val Ser [Cys] Asn Lys Asn [Cys] Thr Ser Gly Gln Asn Glu

316  TGC CCT GAA GGC TGT TTT TGC GGC TTG TTG GGC CAG AAC AAA AAA GGT
     [Cys] Pro Glu Gly [Cys] Phe [Cys] Gly Leu Leu Gly Gln Asn Lys Lys Gly

364  CAT TGC TAC AAA ATT ATA GGG AAC CTT TCT GGA GAA CCA CCA GTT GTA
     His [Cys] Tyr Lys Ile Ile Gly Asn Leu Ser Gly Glu Pro Pro Val Val

412  AGG CGT TAA GGAGATGACC TACAGCTCAG ATGAATAATA AAAAAAATTA AGACTAANAA
     Arg Arg Stop

471  AAAAAAAAAA AAAAAAAAAA AAANCCTTGT CGGCCGCCT
```

Fig. 2

```
                      Evasin 3 PCR2F                    Evasin 3 PCR1F
                ───────────────────────▶         ─────────────────────────▶

1    GGGGACAAGT TTGTACAAAA AAGCAGGCTT CGCCACCATG GTGTCGATGA
                                                   M   V  S  M    T  T

61    TCATGTCCTA TTTCTGCTAG TTGCTTTGGA ATCAATGCGA CCCTACACGA
        H  H  V  L   F  L  L   V  A  L    E  S  M  R   P  Y  T    T  A

121    TTCAACTATT GAGTCAAGAA CGAGTGGAGA TGGCGCAGAT AACTTTGATG
        V  S  T  I   E  S  R    T  S  G    D  GA  D   N  F  D    V  V  S

181    TAATAAGAAT TGCACTTCAG GTCAAAACGA ATGCCCTGAA GGCTGTTTTT
         C  N  K  N    C  T  S   G  Q  N    E  C  P  E   G  C  F    C  G

241    GGGCCAGAAC AAAAAAGGTC ATTGCTACAA AATTATAGGG AACCTTTCTG
        L  G  Q  N   K  K  G    H  C  Y  K    I  I  G    N  L  S    G  E

Evasin 3 PCR1R
                ◀───────────────────────
301    AGTTGTAAGG CGTCACCATC ACCATCACCA TTGAAACCCA GCTTTCTTGT
          P  V  V  R   R  H  H    H  H  H                Evasin 3 PCR2R
                                                  ◀─────────────────────────

361    CCCC
```

```
       5'NdeI-eva3 ecoli
    ─────────────────────────▶
  1 GGAATTCCAT ATGCTTGTTT CAACTATTGA GTCAAGAACG AGTGGAGATG
                M  L  V   S  T  I  E   S  R  T   S  G  D 51 GCGCAGATAA CTTTGATGTA GTATCTTGTA ATAAGAATTG CACTTCAGGT
     G  A  D   N  F  D  V   V  S  C   N  K  N   C  T  S  G 101 CAAAACGAAT GCCCTGAAGG CTGTTTTTGC GGCTTGTTGG GCCAGAACAA
     Q  N  E   C  P  E  G   C  F  C   G  L  L   G  Q  N ◀─────
151 AAAAGGTCAT TGCTACAAAA TTATAGGGAA CCTTTCTGGA GAACCACCAG
     K  K  G  H   C  Y  K   I  I  G   N  L  S  G   E  P  P
         3'XhoI-eva3 ecoli
    ◀─────────────────────
201 TTGTAAGGCG TTAATAACTC GAGCGG
     V  V  R   R
```

Fig. 12
A)
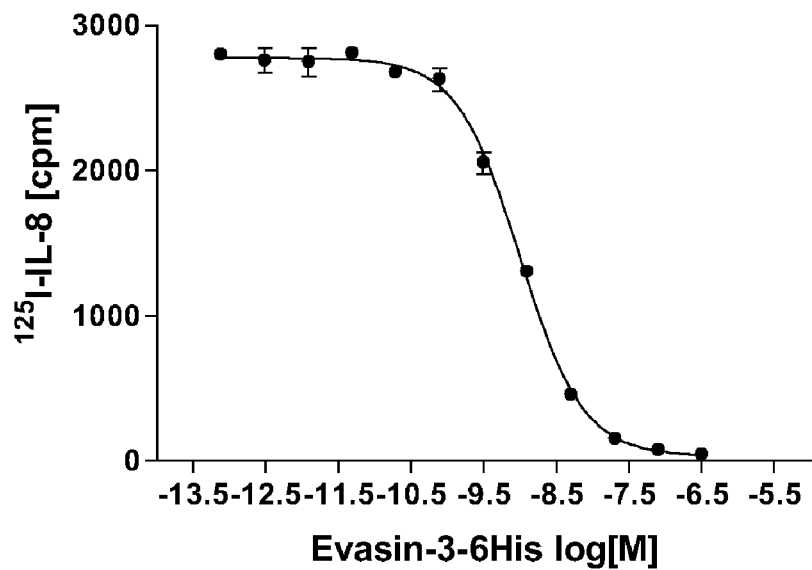
B)
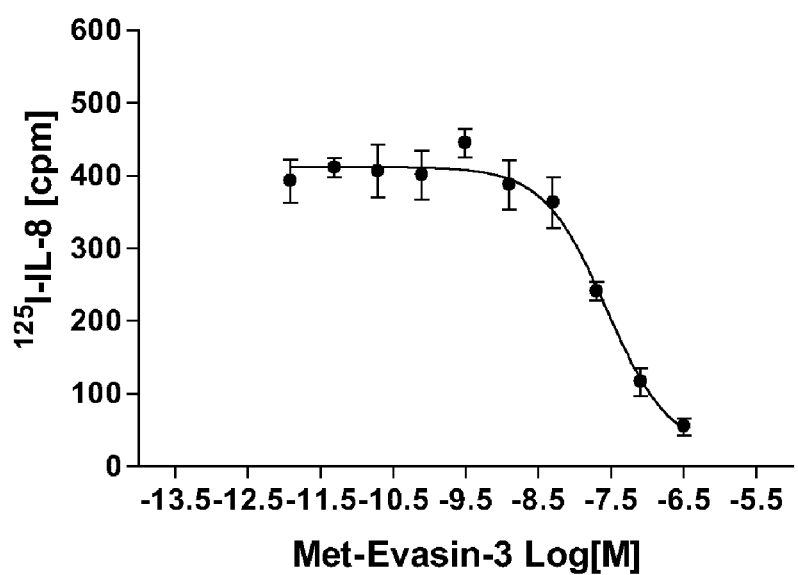

Fig. 13
A)
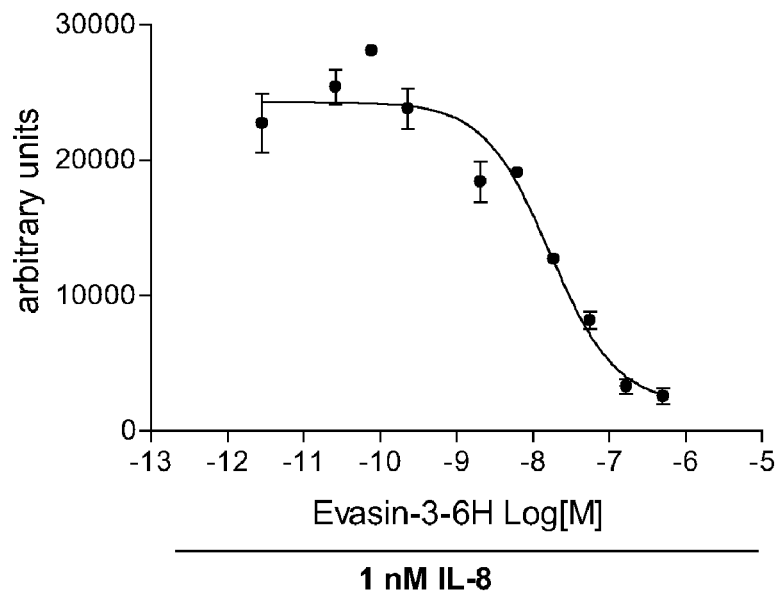
B)
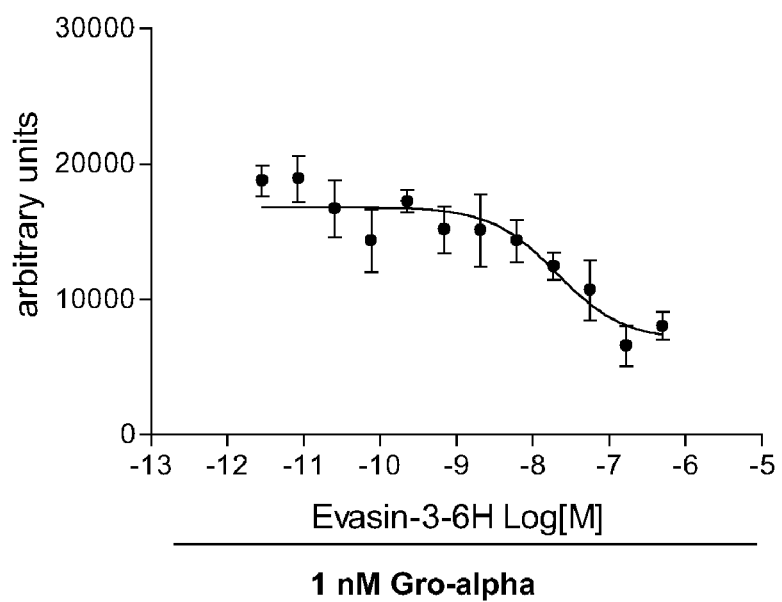

Fig. 14
A) Evasin-3-6His
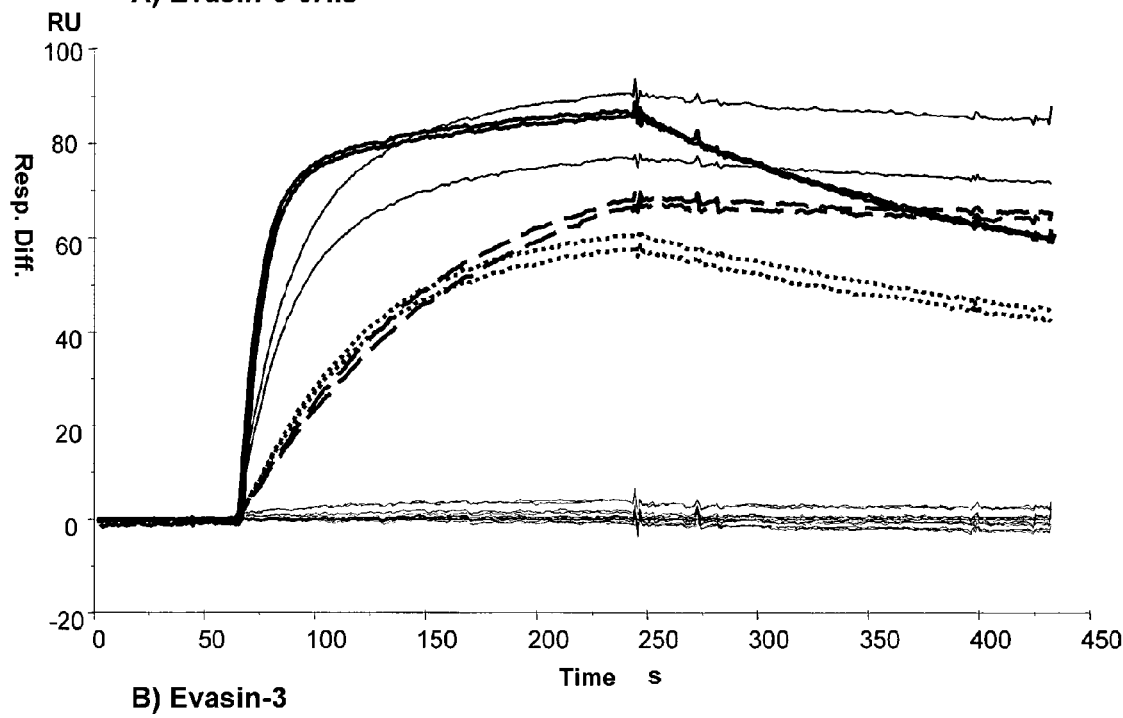
B) Evasin-3
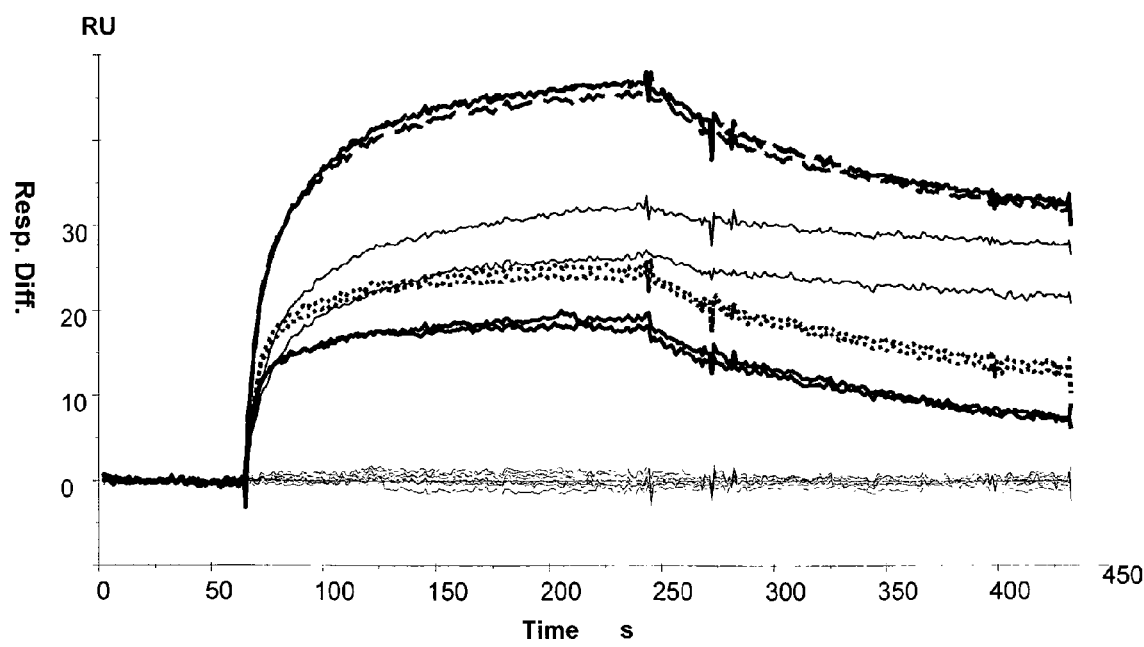

Fig. 15
A)
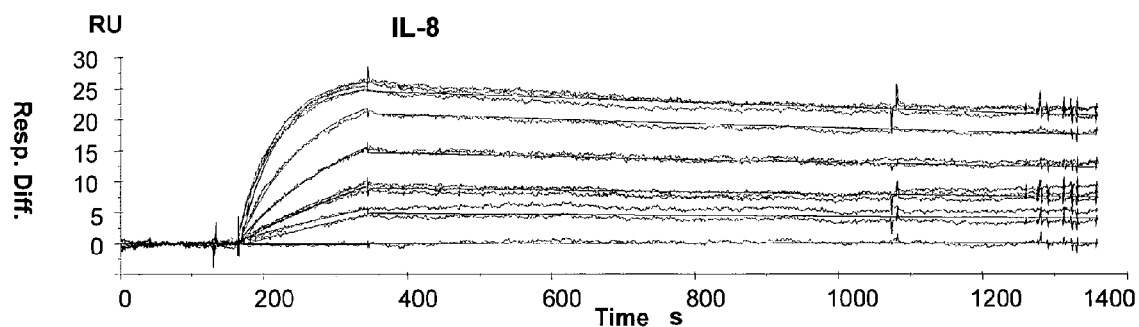
B)
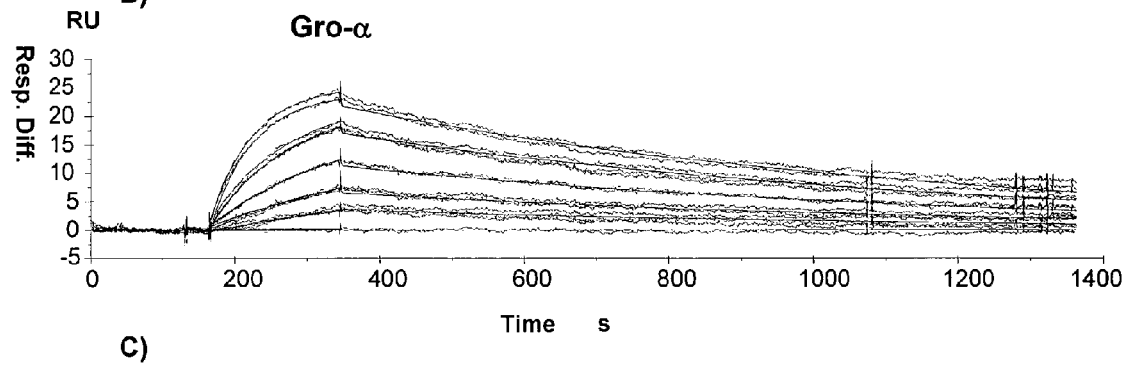
C)
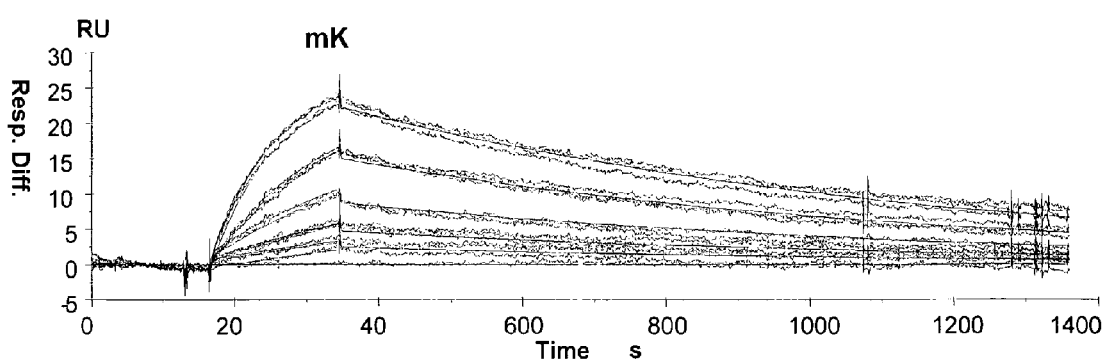

D)

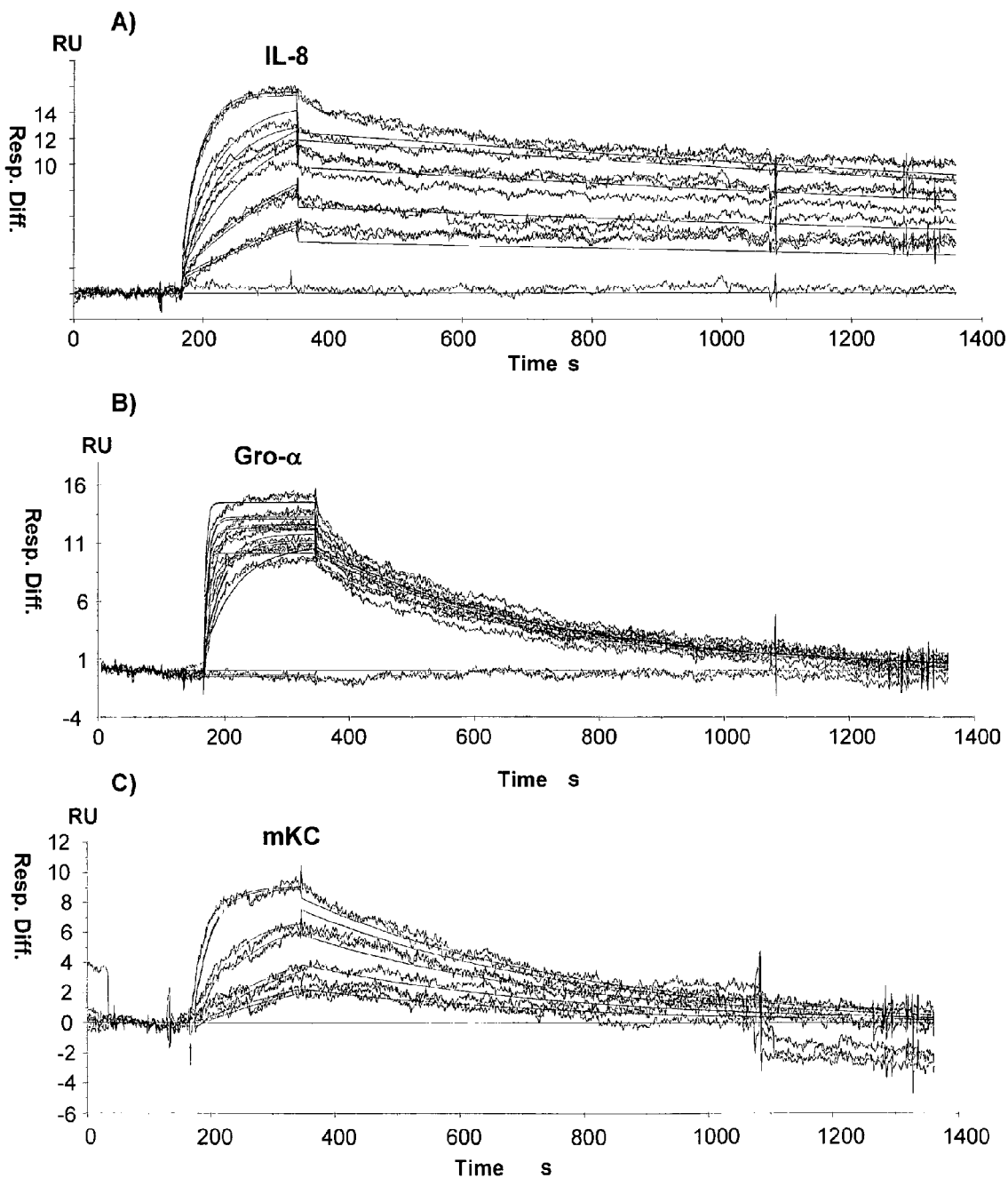

D)

CXC-CHEMOKINE ANTAGONISTS ISOLATED FROM *RHIPICEPHALUS SANGUINEUS*

CROSS-REFERENCE TO RELATED APPLICATION

This application is the U.S. national stage application of International Patent Application No. PCT/EP2006/067939, filed Oct. 30, 2006, which claims the benefit of U.S. Provisional Patent Application No. 60/733,547, filed Nov. 4, 2005, the disclosures of which are hereby incorporated by reference in their entireties, including all figures, tables and amino acid or nucleic acid sequences.

FIELD OF THE INVENTION

The invention relates to novel antagonists of CXC-chemokines, particularly antagonists of CXCL8 and related CXC chemokines, and their uses, particularly as anti-inflammatory or immuno-modulatory compounds and in the treatment or prevention of CXC-chemokine-related diseases.

BACKGROUND OF THE INVENTION

Chemokines are small, secreted pro-inflammatory proteins, which mediate directional migration of leukocytes from the blood to the site of injury. Depending on the position of the conserved cysteines characterizing this family of proteins, the chemokine family can be divided structurally into C, CC, CXC and $CX_3C$ chemokines that bind to a series of membrane receptors (Baggiolini M et al., 1997). These membrane receptors, all heptahelical G-protein coupled receptors, allow chemokines to exert their biological activity on the target cells, which may present specific combinations of receptors according to their state and/or type. The physiological effects of chemokines result from a complex and integrated system of concurrent interactions: the receptors often have overlapping ligand specificity, so that a single receptor can bind different chemokines. A single chemokine can bind to different receptors as well.

Studies on structure-activity relationships indicate that chemokines have two main sites of interaction with their receptors, the flexible amino-terminal region and the conformationally rigid loop that follows the second Cysteine. Chemokines are thought to dock onto receptors by means of the loop region, and this contact is believed to facilitate the binding of the amino-terminal region that results in receptor activation.

Usually, chemokines are produced at the site of injury and cause leukocyte migration and activation, playing a fundamental role in inflammatory, immune, homeostatic, hematopoietic, and angiogenic processes. Thus, these molecules are considered good target candidates for therapeutic intervention in diseases associated with such processes. The inhibition of chemokines, or of their receptors, can reduce leukocyte maturation, recruitment and activation, as well as other pathological processes related to angiogenesis or arteriosclerosis (Baggiolini M, 2001).

In addition to mutant inhibitory chemokines, antibodies and peptide and small molecule inhibitors blocking the receptors, the search for effective chemokine antagonists has also been extended to a series of viruses and other organisms that, when entering into contact with human or mammal hosts, show potent immunomodulatory activities affecting the host. The viral mimicry of cytokines, chemokines, and their receptors may indicate strategies of immune modulation for developing therapeutic products. Recently, immunomodulatory factors expressed by haematophagous arthropods (such as mosquitoes, sandflies and ticks) have been reviewed (Gillespie, R D et al, 2001).

In particular, the salivary glands of ticks produce a complex mixture of bioactive molecules having, in particular, anti-inflammatory, anti-haemostatic and anti-immune activities. These include bioactive proteins that control histamine, bind immunoglobulins, or inhibit the alternative complement cascade or other proteases.

Despite the large amount of literature, only a few articles list cDNA sequences identified by random sequencing and differential screenings of libraries generated from various tick tissues and/or species. However, the large majority of these sequences have not been characterized biochemically or functionally, and many annotations are entered only on the basis of sequence similarity with known proteins involved in basic cellular functions, such as those previously characterised in tick salivary glands for enzymatic activities or inducing antibody response. In particular, there is no indication of tick proteins acting as CXC-chemokine binding proteins and functioning as CXC-chemokine antagonists.

SUMMARY OF THE INVENTION

Surprisingly, it has been found that the saliva of *Rhipicephalus sanguineus* (dog tick) contains a novel protein termed Evasin-3, which binds CXC-chemokines and inhibits their activity. Evasin-3 was cloned from a *Rhipicephalus sanguineus* cDNA library, and expressed in mammalian and *E. coli* cells. This protein, as well as derivatives, fragments or mimetics thereof, can be used therapeutically, e.g., as antagonists of CXC-chemokines in mammalian organisms, or as targets for vaccination and for the control of ticks and of tick-borne pathogens.

A first aspect of the invention thus relates to a polypeptide comprising the amino acid sequence of Evasin-3 or of a fragment or analog thereof. Preferred polypeptides of this invention bind a CXC-chemokine, and inhibit its biological activity. A specific example of such a polypeptide is Evasin-3 or a fragment thereof.

A second aspect of the invention relates to nucleic acid molecules encoding a polypeptide as defined above. Such nucleic acids also include oligonucleotides isolated from them and vectors containing said molecules, in particular expression vectors.

A third aspect of this invention resides in antibodies that selectively bind the polypeptides as defined above.

A fourth aspect of this invention relates to host cells and transgenic non-human animals expressing a polypeptide as defined above, as well as methods of producing such cells and transgenic non-human animals.

A fifth aspect of this invention is a process for preparing a polypeptide as defined above, typically using recombinant technologies.

A sixth aspect of the invention is a pharmaceutical (including a vaccine or immunogenic) composition comprising a polypeptide or nucleic acid molecule as defined above and a pharmaceutically acceptable carrier or vehicle.

A seventh aspect of the invention relates to the use of a polypeptide or nucleic acid molecule as defined above as a medicament, in particular for the preparation of a medicament for regulating an immune or inflammatory response in a mammal, as well as to corresponding methods for treatment.

Other features and advantages of the invention will be apparent from the following detailed description.

DESCRIPTION OF THE FIGURES

FIG. 1: Nucleotide sequence of Evasin-3 cDNA sequence with translation of the open reading frame (ORF). The signal sequence (residues 1-26), predicted by the SIGNALP algorithm is underlined. The predicted polyadenylation site is boxed. The Cysteine residues present in the mature protein are highlighted. The predicted N-linked glycosylation sites are in bold.

FIG. 2: Nucleotide sequence and translation of Gateway compatible Evasin-3 cDNA containing 5' and 3' flanking attB sites generated by two successive rounds of PCR. The arrows indicate the position and sense of the relevant PCR primers (Primer sequences are listed in Table III). Start and stop codons are in bold. The predicted signal sequence is underlined.

FIG. 8: Alignment of Evasin-3 cDNA containing the 5' NdeI and 3' XhoI restriction sites generated by PCR. The arrows indicate the position and sense of the relevant PCR primers (summarized in Table IV). Start codons are in bold type and stop codons in italic type.

FIG. 12: A) Inhibition of $^{125}$I-IL-8 binding to CXCR1 by recombinant Evasin-3-6His purified from HEK 293 cells. The IC$_{50}$ value is 1 nM.
B) Inhibition of $^{125}$I-IL-8 binding to CXCR1 by recombinant Evasin-3 produced in *E. Coli*. The IC$_{50}$ value is 20 nM.

FIG. 13: Inhibitory effect of Evasin-3-6His on IL-8 (A) and Gro-alpha (B) induced chemotaxis of human neutrophils. The arbitrary units on the Y axis are proportional to the number of migrated cells. The IC$_{50}$ values are 16 nM for IL-8 and 20 nM for Gro-alpha.

FIG. 14: SPR analysis of CXC-chemokines binding to A) Evasin-3-6His or B) Evasin-3 immobilized on a CM4 chip. CXCL8/IL-8 (black), Gro-alpha/CXCL1 (gray), murine CXCL1/KC (dotted line) and murine CXCL2/MIP-2 (light gray) showed a positive binding whereas the other chemokines tested: CCL5/RANTES, CX3CL1/Fractalkine, CCL11/eotaxin. CCL3/MIP-1-alpha, CCL4/MIP-1β, CCL18/PARC, CCL2/MCP-1 and CXCL12/SDF-1-alpha were negative.

DETAILED DESCRIPTION OF THE INVENTION

Figure 3:
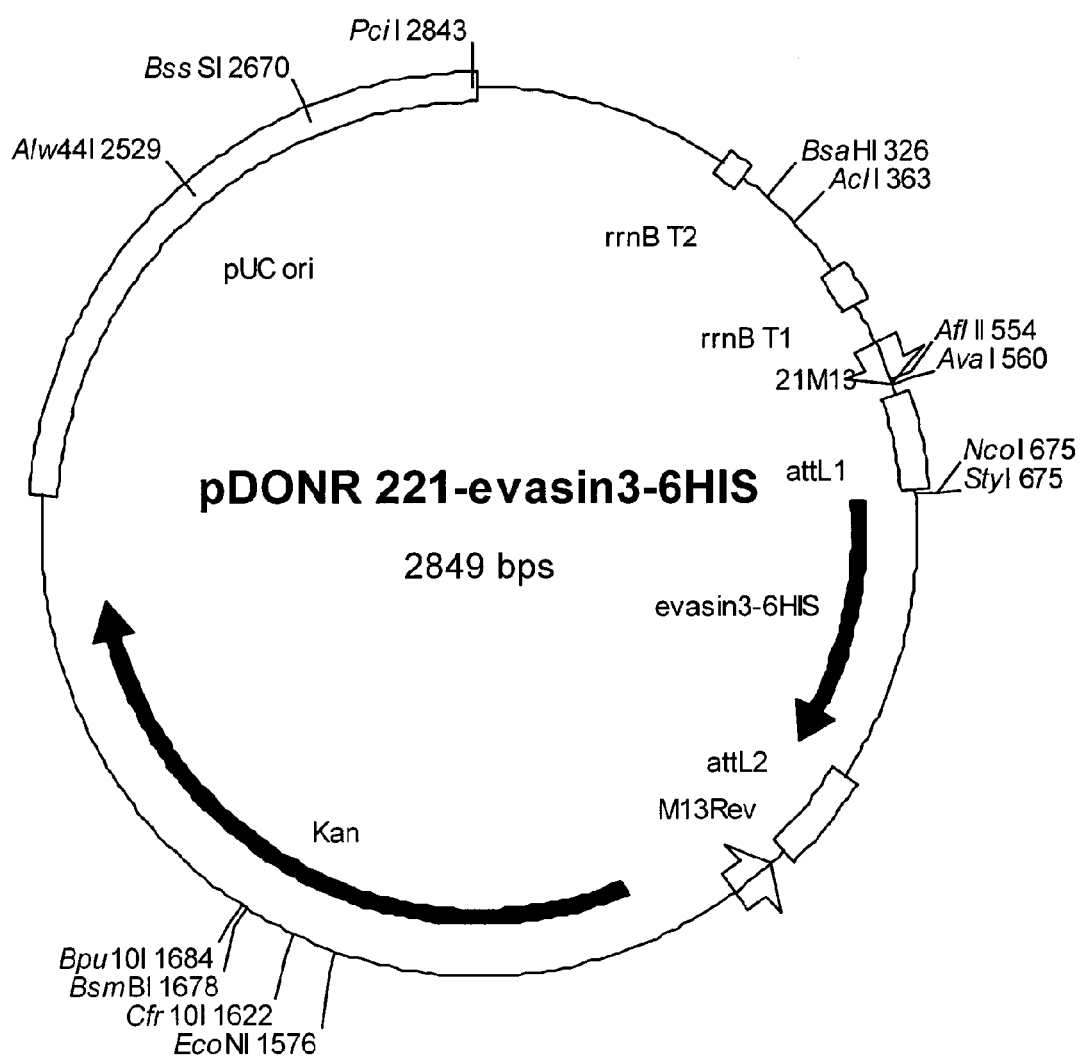
FIG. 3: (A) Map of the pDONR221_Evasin-3-6HIS Gateway entry vector. (B) Map of the pDEST8_Evasin-3-6HIS Gateway expression vector for expression in TN5 (insect) cells. (C) Map of the pEAK12d_evasin3-6HIS Gateway expression vector for expression in human embryonic kidney cells HEK293/EBNA cells. (D) Map of the pEXPII-evasin3-6HIS expression vector for expression in HEK293/EBNA cells.
Figure 3:
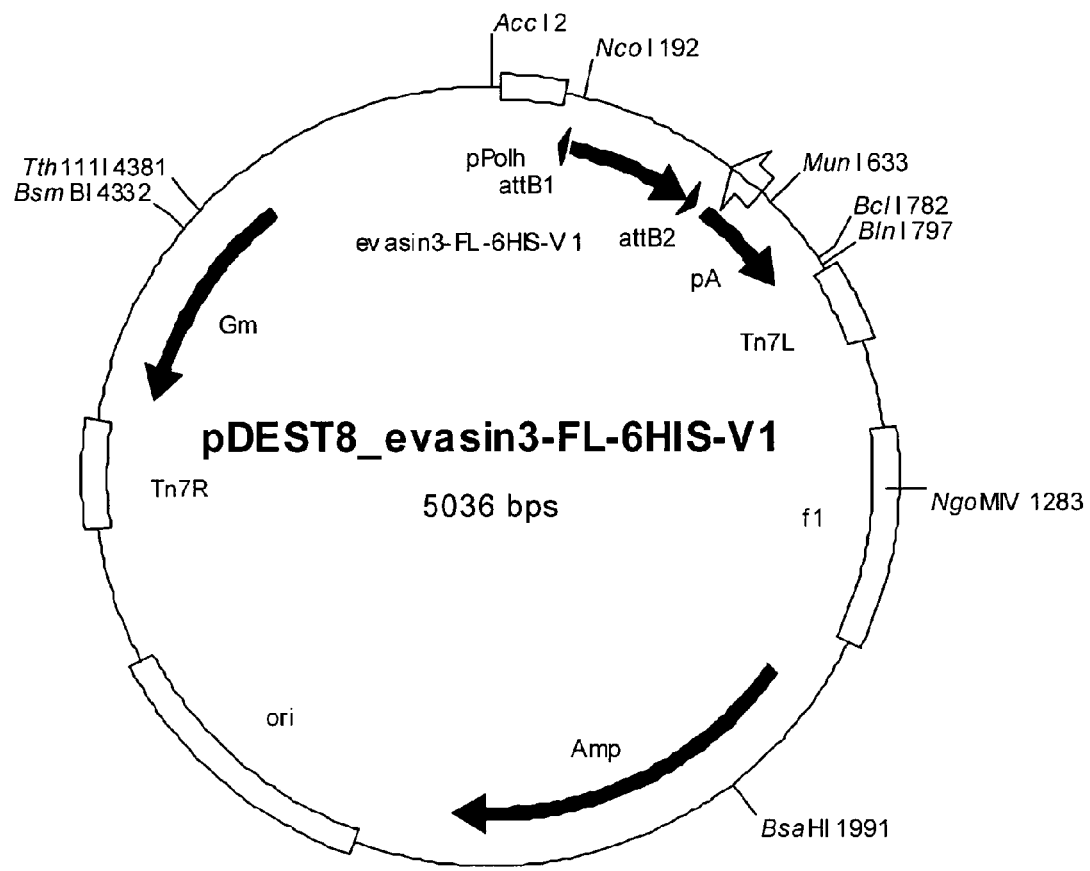
Figure 3:
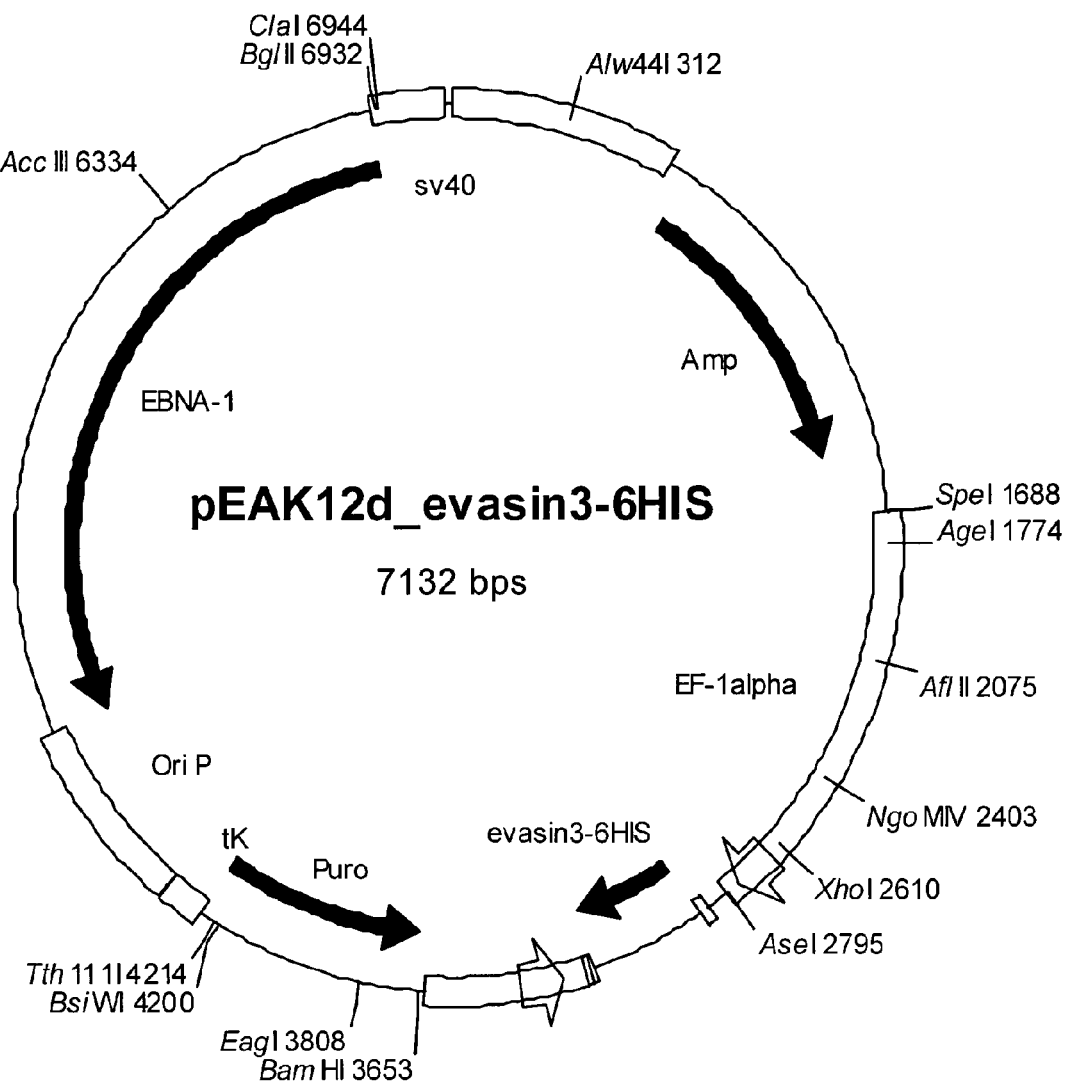
Figure 3:
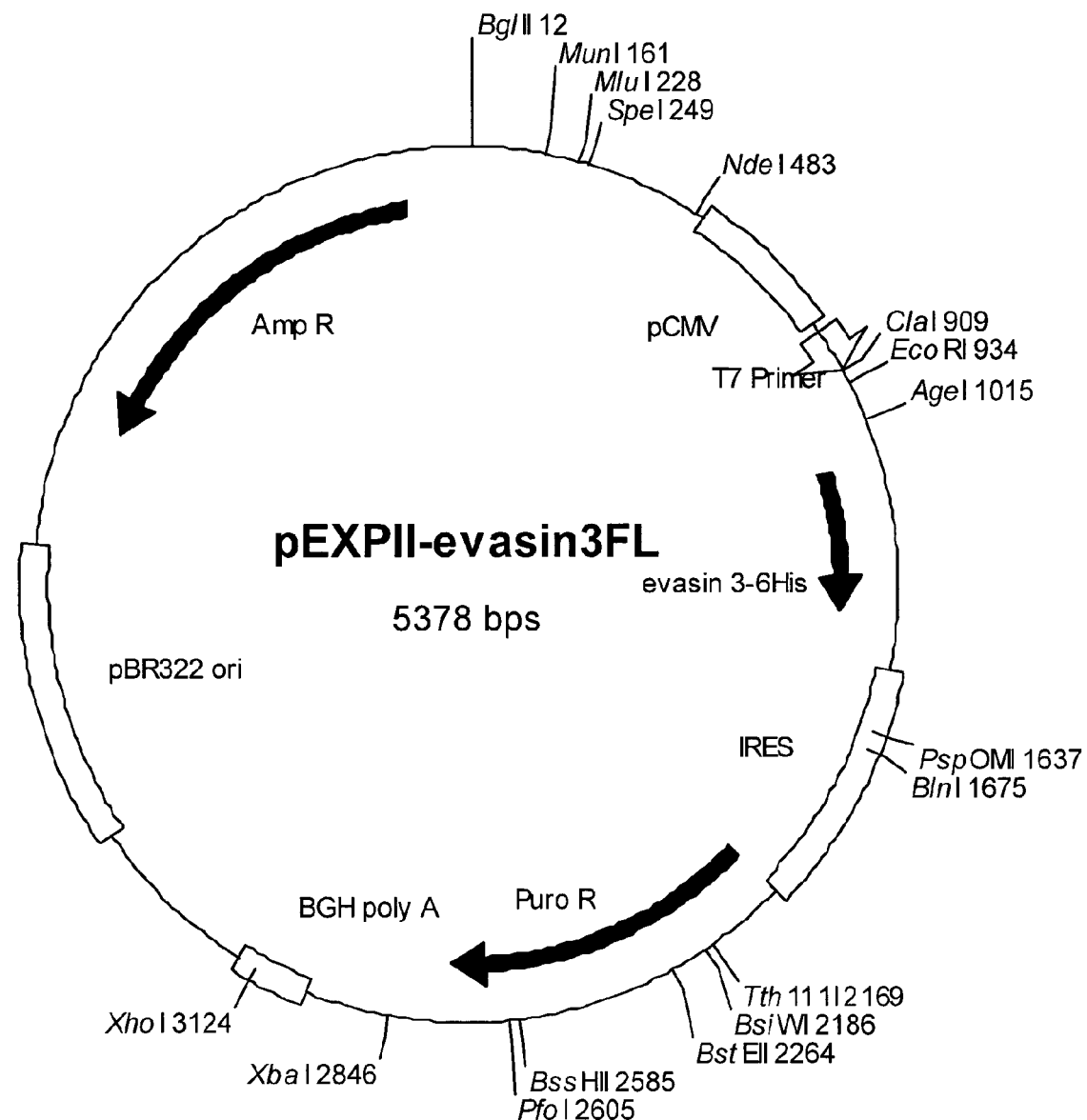

The present invention provides novel compositions and methods for regulating chemokine activity. More particularly, the present invention discloses a novel protein having CXC-chemokine binding properties, that can be used to inhibit chemokine action. The examples show that this protein, derived from tick saliva, can be expressed and purified in recombinant form, and effectively binds CXC-chemokines and will thus inhibit their action, e.g., the specific chemotactic response of cells induced by a CXC-chemokine.

A first aspect of the invention thus resides in an Evasin-3 polypeptide, i.e., any polypeptide comprising the amino acid sequence of Evasin-3 or of a fragment or analog thereof. Preferred polypeptides of this invention bind a CXC-chemokine, in particular CXCL8 (also referred to as IL-8), and inhibit the activity of said chemokine. Particular polypeptides of this invention are selected from the group consisting of:
  a) a protein comprising an amino acid sequence of Evasin-3 (SEQ ID NO: 5);
  b) a protein comprising an amino acid sequence of mature Evasin-3 (SEQ ID NO: 6) or of mature Met-Evasin-3 (SEQ ID NO:26);
  c) a protein comprising an amino acid sequence of Evasin-3-HIS (SEQ ID NO: 17);
  d) a protein comprising an amino acid sequence of mature Evasin-3-HIS (SEQ ID NO: 18);
  e) a protein encoded by a nucleic acid molecule capable of hybridization to a nucleic acid sequence encoding a protein of a), b), c) or d) under stringent conditions, said nucleic acid molecule encoding a protein that binds a CXC-chemokine and inhibits the activity of said chemokine;
  f) a protein at least about 70% identical in amino acid sequence to a protein of a), b), c), or d), and that binds a CXC-chemokine and inhibits the activity of said chemokine;
  g) a protein comprising a fragment of a protein of a), b), c), d), e), or f), which fragment retains the ability to bind a CXC-chemokine and inhibit the activity of said chemokine; and
  h) a protein comprising a fragment of a protein of a), b), c), d), e), or f), which fragment has an immuno-modulatory activity.

In a preferred embodiment, the protein is selected from the group consisting of:
  a) a protein having an amino acid sequence of Evasin-3 (SEQ ID NO: 5);
  b) a protein having an amino acid sequence of mature Evasin-3 (SEQ ID NO 6) or of mature Met-Evasin-3 (SEQ ID NO:26);
  c) a protein having an amino acid sequence of Evasin-3-HIS (SEQ ID NO: 17);
  d) a protein having an amino acid sequence of mature Evasin-3-HIS (SEQ ID NO: 18);
  e) a protein comprising a fragment of a protein of a), b), c), or d), which fragment binds a CXC-chemokine and inhibits the activity of said chemokine;
  f) a protein comprising a fragment of a protein of a), b), c), or d), which fragment has an immunomodulatory activity.

In another aspect, the invention relates to an active mutant of a protein defined above, in which mutant one or more amino acid residues have been added, deleted, or substituted and which mutant binds a CXC-chemokine and inhibits the activity of said chemokine.

The polypeptides of the invention can be in a mature form, resulting from one or more post-translational modifications (glycosylation, phosphorylation, modification with endo-/exopeptidases for eliminating the signal peptide, for example) or from the in-frame addition of sequence encoding heterologous sequences (such as tags or domains that improve the detection and/or the purification). For example, Evasin-3 can be expressed as a recombinant histidine-tagged protein in the complete (SEQ ID NO: 17) and mature form (SEQ ID NO: 18), in both a mammalian and an insect cell line.

The polypeptides of this invention or their corresponding nucleic acids may be in isolated form (e.g., not in their natural environment), including recombinant or synthetic polypeptides and nucleic acids.

The examples show that Evasin-3 polypeptides bind CXC-chemokines, in particular CXCL8 (also called IL-8) and also CXCL1 (also called Gro-α) but not CC-chemokines such as CCL2, CCL5, CCL11 or CCL17 and it can be used to inhibit (e.g., reduce) their activity. This characterization was performed by making use of a series of biochemical assays, including the use of radioactive CXC-chemokines. As demonstrated in the examples, Evasin-3 polypeptides bind CXC-chemokines, in particular CXCL8/IL-8. Such activity confers to the Evasin-3 polypeptides of this invention a broad range of therapeutic utility, as discussed below.

Within the context of the present invention, a fragment of a polypeptide designates any fragment comprising at least 5, 6, 7, 8, 9 or 10 consecutive amino acid residues of said polypeptide sequence. Particular fragments of this invention comprise 15, 20, 25 or more amino acid residues of an Evasin-3 protein as disclosed therein. Preferred fragments retain at least one biological activity of a full-length protein, e.g., an immunogenic activity or an immunomodulatory activity.

In this regard, within the context of the present invention, an "immunomodulatory activity" designates any activity detected in vitro or in vivo that affects the immune response in either a positive or negative manner. Examples of such activities are immunizing activities, immunosuppressive activities, anti-inflammatory activities, pro-/anti-apoptotic activities, or anti-tumoral activities.

Alternatively the fragment can be identified as providing an immunizing activity when administered to a mammal. These fragments should have appropriate antigenic, immunogenic properties for raising an immune response when needed (for example, against ticks or tick-borne pathogenic organisms). The literature provides many examples on how such functional sequences can be identified as candidate vaccine antigens, and eventually administered with adjuvants and/or cross-linked to a carrier. (Mulenga A et al. 2000; WO 01/80881; WO 03/030931; WO 01/87270). A specific antigen or group of antigens identified in Evasin-3 can be used for preventing or reducing ectoparasite infection or disease in an animal, so that the immunity of the animal to the ectoparasite is boosted by natural challenge of the animal with the ectoparasite (WO 95/22603). Finally, the fragment can be also used for raising antibodies directed to the entire protein for screening or diagnostic applications.

The properties of Evasin-3 defined above, and exemplified herein using recombinant variants of this sequence, can be maintained, or even potentiated, in the active mutants. This category of molecules includes natural or synthetic analogs of said sequence, wherein one or more amino acid residues have been added, deleted, or substituted, provided they display the same biological activity characterized in the present invention at comparable or higher levels, as determined by means disclosed in the Examples below.

In particular, the term "active" means that such alternative compounds should maintain, or even potentiate, the CXC-chemokine binding and immunomodulatory properties of Evasin-3.

Active mutant molecules can be generated by site-directed mutagenesis techniques, combinatorial technologies at the level of encoding DNA sequence (such as DNA shuffling, phage display/selection), or by computer-aided design studies, or any other known technique suitable thereof, which provide a finite set of substantially corresponding mutated or shortened peptides or polypeptides. These alternative molecules can be routinely obtained and tested by one of ordinary skill in the art using the teachings presented in the prior art and in the Examples below.

In accordance with the present invention, preferred changes in these active mutants are commonly known as "conservative" or "safe" substitutions, and involve non-basic residues. Conservative amino acid substitutions are those with amino acids having sufficiently similar chemical properties, in order to preserve the structure and the biological function of the molecule. It is clear that insertions and deletions of amino acids may also be made in the above defined sequences without altering their function, particularly if the insertions or deletions only involve a few amino acids, e.g., under ten, and preferably under three, and do not remove or displace amino acids which are critical to the functional conformation of a protein or a peptide.

The literature provides many models on which the selection of conservative amino acids substitutions can be performed on the basis of statistical and physico-chemical studies on the sequence and/or the structure of natural protein (Rogov S I and Nekrasov A N, 2001). Protein design experiments have shown that the use of specific subsets of amino acids can produce foldable and active proteins, helping in the classification of amino acid "synonymous" substitutions which can be more easily accommodated in the protein structure, and which can be used to detect functional and structural Evasin-3 homologs and paralogs (Murphy L R et al., 2000). The synonymous amino acid groups and more preferred synonymous groups for the substitutions are those defined in Table I.

However, in the context of Evasin-3 sequence, specific residues may have a particular importance. For example, Evasin-3 is not significantly homologous to any known proteins but contains a pair number of cysteine residues in the mature protein, in particular in the position corresponding to 22, 26, 33, 37, 39 and 50 in mature Evasin-3. Moreover, Evasin-3 contains potential glycosylation sites in the position corresponding to Asparagine 25 and 56 in the mature Evasin-3. These residues may be important for the correct folding and/or activity and should be preferably conserved in the corresponding positions of these alternative polypeptides. Alternatively, the deleted or substituted cysteines or glycosylation sites can be re-established in a different position of the protein.

Alternatively, active mutants of Evasin-3 may result from sequence alterations reducing the immunogenicity of said CXC-chemokine binding protein when administered to a mammal. The literature provides many examples of these sequence alterations that can be designed and introduced at this scope or for other functional optimizations that allow a safe and effective administration of a therapeutic protein, especially when it is a non-human, non-mammalian, or non-natural protein (Schellekens H, 2002). Examples of technical approaches for achieving these molecules are directed evolution (Vasserot A P et al., 2003), rational design (Marshall S A et al., 2003), bioinformatics (Gendel S M, 2002), the identification and the neutralization of CD4+ T-cell epitopes (WO 03/104263; WO 03/006047; WO 02/98454; WO 98/52976; WO 01/40281), fusion with other protein sequences (WO 02/79415; WO 94/11028), or conjugation with other compounds (WO 96/40792).

Active Evasin-3-derived sequences can be natural analogs or orthologs of Evasin-3 that may be isolated from, in particular, other tick species, in particular those belonging to the Ixodidae family, and more in particular to the subfamiliy Rhipicephalinae, to which *Rhipicephalus sanguineus* belongs, as well to other subfamilies like Ixodinae (including *Ixodes scapularis* and *Ixodes ricinus*) or Amblyomminae (including *Amblyomma variegatum* and *Amblyomma americanum*). Alternatively, orthologs may be identified in mammas, such as man and mouse.

Limited information is available on the genome and the transcriptome of haematophagous arthropods, and is mostly associated with ribosomal and mitochondrial sequences, which were studied to determine the phylogenetic relationships on the basis of their conservation (Murrell A et al., 2001). Tick genomic data are available only in partial and preliminary formats (Ullmann A J et al., 2002), but further analysis of the tick genes encoding CXC-chemokine binding proteins can be performed by using genomic DNA that can be extracted from ixodid ticks by applying specific methods and conditions (Hill C A and Gutierrez, J A 2003), in particular for detecting any significant polymorphism in salivary gland proteins, as already demonstrated (Wang H et al., 1999). The genomic and protein sequences of these organisms is important for understanding their physiology and biology, therefore providing information useful for understanding the role of the proteins of the invention in host, parasite, and parasite-borne pathogens relationships (Valenzuela J G, 2002b).

The biochemical and physiological characterization of the CXC-chemokine binding activities described for proteins homologous to Evasin-3 in the present invention can be performed by applying any of the technologies recently improved for the study of tick and tick-borne pathogens, such as two-dimensional gel electrophoresis (Madden R D et al., 2004) or RNA interference (Aljamali M N et al., 2003). Moreover, further studies can be performed to map the CXC-chemokine recognition site on these proteins and the mechanisms of CXC-chemokine antagonism (Seet B T et al., 2001; Beck C G et al., 2001; Burns J M et al., 2002; Webb L M et al., 2004) or to identify relevant post-translational modifications (Alarcon-Chaidez F J et al., 2003).

Another aspect of the invention are fusion proteins comprising an Evasin-3 polypeptide as defined above operably linked to a heterologous domain, e.g., one or more amino acid sequences which may be chosen amongst the following: an extracellular domain of a membrane-bound protein, immunoglobulin constant regions (Fc region), multimerization domains, export signals, and tag sequences (such as the ones helping the purification by affinity: HA tag, Histidine tag, GST, FLAAG peptides, or MBP).

In the context of a fusion protein, the expression "operably linked" indicates that the Evasin-3 polypeptide and additional amino acid sequences are associated through peptide linkage(s), either directly or via spacer residues (e.g., a linker). In this manner, the fusion protein can be produced recombinantly, by direct expression in a host cell of a nucleic acid molecule encoding the same, as will be discussed below. Also, if needed, the additional amino acid sequences included in the fusion protein can be eliminated, either at the end of the production/purification process or in vivo, e.g., by means of an appropriate endo-/exopeptidase, as will be discussed below. The heterologous moiety may be operably linked to either the N- or the C-terminal portion of the Evasin-3 polypeptide.

The design of the moieties and/or linkers, as well as methods and strategies for the construction, purification, detection, maturation, and use of fusion proteins are widely discussed in the literature (Nilsson J et al., 1997; "Applications of chimeric genes and hybrid proteins" Methods Enzymol. Vol. 326-328, Academic Press, 2000). In general, the heterologous sequences are intended to provide additional properties without impairing the therapeutic activity of the original protein (CXC-chemokine binding, for example) in a significant manner. Examples of such additional properties are an easier purification procedure, a longer lasting half-life in body fluids, an additional binding moiety, the maturation by means of an endoproteolytic digestion, the stability during recombinant production, or extracellular localization. This latter feature is of particular importance for defining a specific group of fusion or chimeric proteins included in the above definition since it allows the polypeptides to be localized in the space where the isolation and purification of these polypeptides is facilitated, and where CXC-chemokines are normally active.

The choice of one or more of these sequences to be fused to a Evasin-3 polypeptide is dependent on the specific use and/or purification protocol of said protein as recombinant protein. For example, the activity of Evasin-3 was tested in the examples by means of a fusion protein including a histidine tag sequence facilitating both detection and purification of Evasin-3. These sequences can be chosen amongst the following three basic groups of heterologous sequences.

A first group of such sequences consists of sequences helping the secretion and the purification of the protein using recombinant DNA technologies, such as a signal peptide and export signals (Rapoport T A et al., 1996), or tag sequences helping the purification by affinity (HA tag, Histidine tag, GST, FLAG, or MBP).

A second group of heterologous sequences is represented by those allowing a better stability and bioactivity of the proteins.

A typical example of a strategy allowing a prolonged half-life of a protein is the fusion with human serum albumin, or with peptides and other modified sequences (e.g. by myristoylation) that allow the binding to circulating human serum albumin (Chuang V T et al., 2002; Graslund T et al., 1997; WO 01/77137). Alternatively, the additional sequence may help the targeting to specific localization, such as in the brain (WO 03/32913).

Another way to improve the stability of a recombinant protein when administered to a subject is to generate multimers of the protein by fusing domains isolated from other proteins that allows the formation or dimers, trimers, etc. Example protein sequences allowing the multimerization of the polypeptides of the Invention are domains isolated from proteins such hCG (WO 97/30161), collagen X (WO 04/33486), C4BP (WO 04/20639), Erb proteins (WO 98/02540), or coiled coil peptides (WO 01/00814).

A well-known example of such fusion proteins is represented by the constant/Fc region of human immunoglobulin proteins, allowing the dimerization common to human immunoglobulins. Different strategies for generating fusion proteins comprising a therapeutic protein and an immunoglobulin fragment are disclosed in the literature (WO 91/08298; WO 96/08570; WO 93/22332; WO 04/085478; WO 01/03737, WO 02/66514). For example, the nucleic acid sequence encoding the mature Evasin-3 can be cloned in an expression vector fused to a nucleic acid sequence encoding the original Evasin-3 signal sequence (or any other appropriate signal /export sequence) at its 5' end, and the nucleic acid sequence encoding the constant region of human immunoglobulin lambda heavy chain IgG1 (NCBI Acc. No. CAA75302; segment 246-477) at its 3' end. The resulting vector can be used to transform a CHO or HEK293 host cell line and the clones stably expressing and secreting the recombinant fusion protein having Evasin-3 at the N-terminus and the IgG1 sequence at the C-terminus can be selected. This clone then can be used for scaling up the production and for purifying the recombinant fusion protein from the culture medium. Alternatively, the position of the nucleic acid encoding the constant region of human immunoglobulin lambda heavy chain IgG1 and Evasin-3 can be inversed, and the resulting protein can be expressed and secreted using still the original signal sequence of Evasin-3, or any other appropriate signal/export sequence. Using this technology it can be also possible to generate heterodimers if two different constructs expressing one Evasin-3-Fc fusion protein and the other a different Fc-based fusion protein (for example another CXC-chemokine antagonist) are co-expressed in the same host cell (WO 00/18932).

A further group of heterologous sequences is represented by those adding a further functional activity that can synergise or amplify the ones shown by Evasin-3. These sequences, which are expected to be either isolated from an extracellular domain of a membrane-bound protein (such as a CXC-chemokine receptor) or to be present in a secreted protein, can be active as well as a CXC-chemokine antagonist, and in general should have an immunomodulatory activity.

As mentioned above, the additional sequence included in the fusion proteins may be eliminated, e.g., at the end of the production or purification process, or in vivo, if needed, e.g., by means of an appropriate endo-/exopeptidase. For example, the linker sequence included in the recombinant protein may present a recognition site for an endopeptidase (such as a caspase) that can be used to enzymatically detach the desired protein from the heterologous sequence either in vivo or in vitro. Alternatively, if the protein sequence to be expressed does not contain an initiating methionine (for example, if the sequence encodes for only the mature sequence of the protein, without the signal peptide), a protein of the Invention can be expressed correctly in a host cell with a starting Methionine. This additional amino acid may then be either maintained in the resulting recombinant protein, or eliminated by means of an exopeptidase, such as Methionine Aminopeptidase, according to methods disclosed in the literature (Van Valkenburgh H A and Kahn R A, 2002; Ben-Bassat A, 1991).

Further variants or analogs of the polypeptides of the invention can be obtained in the form of peptide mimetics (also called peptidomimetics), in which the nature of peptide or polypeptide has been chemically modified at the level of amino acid side chains, of amino acid chirality, and/or of the peptide backbone. These alterations are intended to provide antagonists with improved purification, potency and/or pharmacokinetics features. For example, when peptide susceptibility to cleavage by peptidases following injection into the subject is a problem, replacement of a particularly sensitive peptide bond with a non-cleavable peptide mimetic can provide a peptide more stable and thus more useful as a therapeutic. Similarly, the replacement of an L-amino acid residue is a standard way of rendering the peptide less sensitive to proteolysis, and finally more similar to organic compounds other than peptides. Also useful are amino-terminal blocking groups such as t-butyloxycarbonyl, acetyl, theyl, succinyl, methoxysuccinyl, suberyl, adipyl, azelayl, dansyl, benzyloxycarbonyl, fluorenylmethoxycarbonyl, methoxyazelayl, methoxyadipyl, methoxysuberyl, and 2,4-dinitrophenyl. Many other modifications providing increased potency, prolonged activity, ease of purification, and/or increased half-life are known in the art (WO 02/10195; Villain M et al., 2001). Preferred alternative, "synonymous" groups for amino acid derivatives included in peptide mimetics are those defined in Table II. By "amino acid derivative" is intended an amino acid or amino acid-like chemical entity other than one of the 20 genetically encoded naturally occurring amino acids. In particular, the amino acid derivative may contain substituted or non-substituted alkyl moieties that can be linear, branched, or cyclic, and may include one or more heteroatoms. The amino acid derivatives can be made de novo or obtained from commercial sources (Calbiochem-Novabiochem AG, Switzerland; Bachem, USA). The techniques for the synthesis and the development of peptide mimetics, as well as non-peptide mimetics, are well known in the art (Hruby V J and Balse P M, 2000; Golebiowski A et al., 2001). Various methodologies for incorporating unnatural amino acids into proteins, using both in vitro and in vivo translation systems, to probe and/or improve protein structure and function are also disclosed in the literature (Dougherty D A, 2000).

As will be discussed below, the polypeptides of the invention may be prepared by any procedure known in the art, including recombinant technologies and chemical synthesis technologies.

In a further aspect the invention resides in a nucleic acid molecule encoding a polypeptide as defined above, i.e., a polypeptide comprising the amino acid sequence of Evasin-3 or of a fragment or analog thereof. Particular nucleic acid molecules of this invention are selected from the group consisting of:

a) a nucleic acid molecule encoding a protein comprising an amino acid sequence of Evasin-3 (SEQ ID NO: 5);
b) a nucleic acid molecule encoding a protein comprising an amino acid sequence of mature Evasin-3 (SEQ ID NO: 6) or of mature Met-Evasin-3 (SEQ ID NO:26);
c) a nucleic acid molecule encoding a protein comprising an amino acid sequence of Evasin-3-HIS (SEQ ID NO: 17);
d) a nucleic acid molecule encoding a protein comprising an amino acid sequence of mature Evasin-3-HIS (SEQ ID NO: 18);
e) a nucleic acid molecule capable of hybridization to a nucleic acid molecule of a), b), c) or d) under stringent conditions, and which encodes a protein that binds a CXC-chemokine;
f) a nucleic acid molecule encoding a protein at least about 70% identical in amino acid sequence to a protein of a), b), c), or d), and that binds a CXC-chemokine;
g) a nucleic acid molecule encoding a protein comprising a fragment of a protein encoded by a nucleic acid molecule of a), b), c), d), e), or f), which fragment binds a CXC-chemokine; and
h) a degenerate variant of a nucleic acid molecule of a), b), c), d), e), f) or g).

In particular, the nucleic acid molecule encodes a protein selected from the group consisting of:

a) a protein having an amino acid sequence of Evasin-3 (SEQ ID NO: 5);
b) a protein having an amino acid sequence of mature Evasin-3 (SEQ ID NO 6) or of mature Met-Evasin-3 (SEQ ID NO:26);
c) a protein having an amino acid sequence of Evasin-3-HIS (SEQ ID NO: 17);
d) a protein having an amino acid sequence of mature Evasin-3-HIS (SEQ ID NO: 18);
e) a protein comprising a fragment of a protein of a), b), c), or d), which fragment binds a CXC-chemokine;
f) a protein comprising a fragment of a protein of a), b), c), or d), which fragment has an immuno-modulatory activity;
g) an active mutant of a protein of a), b), c), or d), in which mutant one or more amino acid residues have been added, deleted, or substituted and which mutant binds a CXC-chemokine; and
h) a fusion protein, which fusion protein comprises a protein of a), b), c), d), e), f), or g) operably linked to one or more amino acid sequences chosen amongst the following: an extracellular domain of a membrane-bound protein, an immunoglobulin constant region, a multimerization domain, a signal peptide, an export signal, and a tag sequence.

Within the context of the present invention, a "degenerate variant" designates all nucleic acid sequences that, by virtue of the degeneracy of the genetic code, code for the same amino acid sequence as a reference nucleic acid.

Furthermore, the term "nucleic acid molecule" encompasses all different types of nucleic acids, including without limitation deoxyribonucleic acids (e.g., DNA, cDNA, gDNA, synthetic DNA, etc.), ribonucleic acids (e.g., RNA, mRNA, etc.) and peptide nucleic acids (PNA). In a preferred embodiment, the nucleic acid molecule is a DNA molecule, such as a double-stranded DNA molecule, typically a cDNA.

If the main aspects are directed to the DNA and protein sequences of Evasin-3 disclosed in the examples, specific embodiments include a series of Evasin-3-related sequences, such as DNA or RNA sequences capable of hybridizing under moderately stringent conditions (pre-washing solution of 5×SSC, 0.5% SDS, 1.0 mM EDTA (pH 8.0) and hybridization conditions of 50° C., 5×SSC, overnight) to the DNA sequences encoding Evasin-3, and that code for a CXC-chemokine binding protein.

For example, the Invention provides the sequence of the cDNA of *Rhipicephalus sanguineus* expressing Evasin-3 (SEQ ID NO: 3), the associated Open Reading Frame (ORF; SEQ ID NO: 4), a modified cDNA sequence allowing the expression of Evasin-3 as a recombinant protein fused to an histidine tag in mammalian or insect host cells (SEQ ID NO: 15).

In other preferred embodiments the Evasin-3 sequences are DNA molecules encoding proteins that are at least about 70%, preferably 80%, and most preferably 90% identical in amino acid sequence to Evasin-3. This value can be calculated with any of the dedicated programs, such as FASTA (Pearson W R, 2000), and, for fragment or partial sequences, it is calculated on that portion of Evasin-3 that is present in the fragment.

Another preferred embodiment is an oligonucleotide that comprises a fragment of, or that hybridizes specifically to a region of the sequence of a nucleic acid molecule as defined above. Such oligonucleotides typically contain between 5 and 100 nucleotides in length, and can be selected e.g., from the group consisting of oligonucleotides of at least about 20 nucleotides in length, oligonucleotides of at least about 30 nucleotides in length, and oligonucleotides of at least about 50 nucleotides in length. These oligonucleotides can be used for detecting (by PCR or Southern blot, for example) the non-/coding sequences in transcripts encoding Evasin-3 and related sequences in a sample, or for generating and subcloning recombinant variants of Evasin-3, as shown in the example for the 3' end of the primers used for subcloning and modifying Evasin-3 coding sequence as a histidine tagged variant (evasin3PCR forward and reverse; SEQ ID NO: 7 and 8).

In a further aspect, the nucleic acid molecules defined above can be comprised in a cloning or expression vector. In this regard, a particular embodiment of this invention resides in an expression vector comprising a promoter operably associated with a nucleic acid molecule as defined above, in particular a tissue specific, constitutive promoter or regulated (e.g., inducible) promoter. The vector may comprise any additional regulatory element, such as a terminator, enhancer, origin of replication, selection marker, etc. The vector may be a plasmid, phagemid, cosmid, viral vector, phage, artificial chromosome, and the like.

In a particular embodiment, this vector can comprise:
a) a DNA of the invention; and
b) an expression cassette;
wherein said DNA (a) is operably associated with a tissue specific, a constitutive, or an inducible promoter included in sequence (b).

Optionally, if the coding nucleic acid (i.e., sequence (a)) does not contain a codon for an initiating methionine (for example, if this sequence encodes only the mature sequence of the protein, without the signal peptide) the vector or expression cassette may also contain an ATG sequence that is cloned at the 5' of such sequence so that it can be expressed correctly with an initiatingMethionine. This additional amino acid may be then either maintained in the resulting recombinant protein, or eliminated by means of an enzyme, such as Methionine Aminopeptidase, according to methods disclosed in the literature (Van Valkenburgh H A and Kahn R A, 2002; Ben-Bassat A, 1991).

This vector may allow the expression of the proteins of the Invention not only in the condition of tissue culture but also in vivo, for either experimental or therapeutic reasons. For example, cells over-expressing the protein of the Invention can be transferred (e.g. encapsulated) in an animal model to check the physiological effects of the constant administration of the protein, and eventually before applying the cells to humans. Alternatively, the vector can be used for retrovirus-mediated gene transfer, or any other technology allowing the introduction and the expression of a vector or of the isolated DNA coding sequence in animal under the control of an endogenous promoter. This approach allows the generation of transgenic non-human animals in which the proteins of the Invention are expressed constitutively or in a regulated manner (e.g. in specific tissues and/or following the induction with specific compounds). Similar approaches were applied to other non-mammalian chemokine-binding proteins, showing various developmental and pathological effects (Jensen K K et al., 2003; Pyo R et al., 2004; Bursill C A et al., 2004).

Another aspect of the Invention are host cells transformed or transfected with a cloning or expression vector above indicated. These vectors can be used in a process of preparation of the polypeptides of the Invention. In this respect, an aspect of the Invention is a method of preparing an Evasin-3 polypeptide as defined above, comprising culturing recombinant cells as defined above under conditions allowing or promoting expression and recovering the Evasin-3 polypeptide. When the vector expresses the polypeptide as a protein secreted in the extracellular space, the protein can be more easily collected and purified from cultured cells in view of further processing.

Many books and reviews provide teachings on how to clone and produce recombinant proteins using vectors and Prokaryotic or Eukaryotic host cells, such as some titles in the series "A Practical Approach" published by Oxford University Press ("DNA Cloning 2: Expression Systems", 1995; "DNA Cloning 4: Mammalian Systems", 1996; "Protein Expression", 1999; "Protein Purification Techniques", 2001). In particular, the examples show how, once that the DNA sequence encoding for Evasin-3 has been identified by screening the *Rhipicephalus sanguineus* cDNA library, the ORF can be adapted, modified, and inserted into expression vectors for obtaining the corresponding recombinant protein.

In general, the vectors can be episomal or non-/homologously integrating vectors, which can be introduced into the appropriate host cells by any suitable means (transformation, transfection, conjugation, protoplast fusion, electroporation, calcium phosphate-precipitation, direct microinjection, etc.) to transform them. Factors of importance in selecting a particular plasmid, viral, or retroviral vector include: the ease with which recipient cells that contain the vector, may be recognized and selected from those recipient cells which do not contain the vector; the number of copies of the vector which are desired in a particular host; and whether it is desirable to be able to "shuttle" the vector between host cells of different species. The vectors should allow the expression of the isolated proteins of the invention, or the fusion proteins comprising them in the prokaryotic or Eukaryotic host cell under the control of appropriate transcriptional initiation/termination regulatory sequences, which are chosen to be constitutively active or inducible in said cell. A cell line substantially enriched in such cells can be then isolated to provide a stable cell line (as shown in the example with HEK293 and TN5 cell lines).

For eukaryotic host cells (e.g. yeasts, insect or mammalian cells), different transcriptional and translational regulatory sequences may be employed, depending on the nature of the host. They may be derived from viral sources, such as adenovirus, bovine papilloma virus, Simian virus or the like, where the regulatory signals are associated with a particular gene which has a high level of expression. Examples are the TK promoter of the Herpes virus, the SV40 early promoter, the yeast gal4 gene promoter, etc. Transcriptional initiation regulatory signals may be selected which allow for repression and activation, so that expression of the genes can be modulated. The cells, which have been stably transformed by the introduced DNA, can be selected by also introducing one or more markers, which allow for selection of host cells which contain the expression vector. The marker may also provide for phototrophy to an auxotropic host, biocide resistance, e.g. antibiotics, or heavy metals such as copper, or the like. The selectable marker gene can either be directly linked to the DNA gene sequences to be expressed, or introduced into the same cell by co-transfection. Additional elements may also be needed for optimal synthesis of proteins of the invention.

Host cells for recombinant production may be either prokaryotic or eukaryotic cells. Particularly suitable prokaryotic cells include bacteria (such as *Bacillus subtilis* or *E. coli*) transformed with a recombinant bacteriophage, plasmid or cosmid DNA expression vector. Preferred are eukaryotic host cells, e.g. mammalian cells, such as human, monkey, mouse, and Chinese Hamster Ovary (CHO) cells, because they provide post-translational modifications to protein molecules, including correct folding or glycosylation at correct sites. Alternative eukaryotic host cells are yeast cells transformed with yeast expression vectors. Also yeast cells can carry out post-translational peptide modifications including glycosylation. A number of recombinant DNA strategies exist which utilize strong promoter sequences and high copy number plasmids that can be utilized for production of the desired proteins in yeast. Yeast recognizes leader sequences in cloned mammalian gene products and secretes peptides bearing leader sequences (i.e., pre-peptides).

For long-term, high-yield production of a recombinant polypeptide, stable expression is preferred. For example, cell lines, which stably express the polypeptide of interest, may be transformed using expression vectors which may contain viral origins of replication and/or endogenous expression elements and a selectable marker gene on the same or on a separate vector. Following the introduction of the vector, cells may be allowed to grow for 1-2 days in an enriched media before they are switched to selective media. The purpose of the selectable marker is to confer resistance to selection, and its presence allows growth and recovery of cells that successfully express the introduced sequences. Resistant clones of stably transformed cells may be proliferated using tissue culture techniques appropriate to the cell type. A cell line substantially enriched in such cells can be then isolated to provide a stable cell line.

A particularly preferred method of high-yield production of a recombinant polypeptide of the present invention is through the use of dihydrofolate reductase (DHFR) amplification in DHFR-deficient CHO cells, by the use of successively increasing levels of methotrexate as described in U.S. Pat. No. 4,889,803. The polypeptide obtained may be in a glycosylated form.

Mammalian cell lines available as hosts for expression are known in the art and include many immortalised cell lines available from the American Type Culture Collection (ATCC) including, but not limited to, Chinese hamster ovary (CHO), HeLa, baby hamster kidney (BHK), monkey kidney (COS), C127, 3T3, HEK 293, Bowes melanoma and human hepatocellular carcinoma (for example Hep G2) cells and a number of other cell lines. In the baculovirus system, the materials for baculovirus/insect cell expression systems are commercially available in kit form from, inter alia, Invitrogen.

Alternatively, the polypeptides of this invention may be prepared by artificial synthesis. In this regard, examples of chemical synthesis technologies are solid phase synthesis and liquid phase synthesis. As a solid phase synthesis, for example, the amino acid corresponding to the carboxy-terminus of the peptide to be synthetised is bound to a support which is insoluble in organic solvents, and by alternate repetition of reactions, one wherein amino acids with their amino groups and side chain functional groups protected with appropriate protective groups are condensed one by one in order from the carboxy-terminus to the amino-terminus, and one where the amino acids bound to the resin or the protective group of the amino groups of the peptides are released, the peptide chain is thus extended in this manner. Solid phase synthesis methods are largely classified by the tBoc method and the Fmoc method, depending on the type of protective group used. Typically used protective groups include tBoc (t-butoxycarbonyl), Cl-Z (2-chlorobenzyloxycarbonyl), Br-Z (2-bromobenzyloxycarbonyl), Bzl (benzyl), Fmoc (9-fluorenylmethoxycarbonyl), Mbh (4,4'-dimethoxydibenzhydryl), Mtr (4-methoxy-2,3,6-trimethylbenzenesulphonyl), Trt (trityl), Tos (tosyl), Z (benzyloxycarbonyl) and C12-Bzl (2,6-dichlorobenzyl) for the amino groups; NO2 (nitro) and Pmc (2,2,5,7,8-pentamethylchromane-6-sulphonyl) for the guanidino groups); and tBu (t-butyl) for the hydroxyl groups). After synthesis of the desired polypeptide, it is subjected to the de-protection reaction and cut off from the solid support. Such peptide cutting reaction may be carried with hydrogen fluoride or tri-fluoromethane sulfonic acid for the Boc method, and with TFA for the Fmoc method. Totally synthetic proteins of size comparable to that of Evasin-3 are disclosed in the literature (Brown A et al., 1996).

The polypeptides of the present invention can be produced, formulated, administered, or generically used in other alternative forms that can be preferred according to the desired method of use and/or production. The protein of the invention can be post-translationally modified, for example by glycosylation as shown in the examples.

In general the protein of the invention can be provided in the form of active fractions, precursors, salts, derivatives, conjugates or complexes.

As indicated above, the term "active" or "biologically active" means that such alternative compounds should maintain, or even potentiate, the CXC-chemokine binding and/or immunomodulatory properties of Evasin-3.

The term "fraction" refers to any fragment of the polypeptidic chain of the compound itself, alone or in combination with related molecules or residues bound to it, for example residues of sugars or phosphates. Such molecules can result also from other modifications that do not normally alter primary sequence, for example in vitro chemical derivatization of peptides (acetylation or carboxylation), and those made by modifying the protein post-translationally, such as by phosphorylation (introduction of phosphotyrosine, phosphoserine, or phosphothreonine residues) or by glycosylation (by exposing the peptide to enzymes which affect glycosylation e.g., mammalian glycosylating or deglycosylating enzymes) during its synthesis and/or in further processing steps. In particular, Evasin-3 has been characterized in tick saliva and in both recombinant forms disclosed herein as being more or less heavily glycosylated. This modification may be performed in vitro, by using the appropriate modifying enzyme, or in vitro, by choosing the appropriate host cells for recombinant production.

The "precursors" are compounds which can be converted into the compounds of present invention by metabolic and enzymatic processing prior or after the administration to the cells or to the body.

The term "salts" herein refers to both salts of carboxyl groups and to acid addition salts of amino groups of the peptides, polypeptides, or analogs thereof, of the present invention. Salts of a carboxyl group may be formed by means known in the art and include inorganic salts, for example, sodium, calcium, ammonium, ferric or zinc salts, and the like, and salts with organic bases as those formed, for example, with amines, such as triethanolamine, arginine or lysine, piperidine, procaine and the like. Acid addition salts include, for example, salts with mineral acids such as, for example, hydrochloric acid or sulfuric acid, and salts with organic acids such as, for example, acetic acid or oxalic acid. Any of such salts should have substantially similar activity to the peptides and polypeptides of the invention or their analogs.

The term "derivatives" as used herein refers to derivatives that can be prepared from the functional groups present on the lateral chains of the amino acid moieties or on the amino-/ or carboxy-terminal groups according to known methods. Such derivatives include for example esters or aliphatic amides of the carboxyl-groups and N-acyl derivatives of free amino groups or O-acyl derivatives of free hydroxyl-groups and are formed with acyl-groups as for example alcanoyl- or aroyl-groups.

The proteins of the Invention can be in the form of an active conjugate or complex with a molecule chosen amongst radioactive labels, biotin, fluorescent labels, cytotoxic agents, and drug delivery agents. Useful conjugates or complexes can be generated, using molecules and methods known in the art, for various reasons, for example for allowing the detection of the interaction with CXC-chemokines or other proteins (radioactive or fluorescent labels, biotin), therapeutic efficacy (cytotoxic agents), or improving the agents in terms of drug delivery efficacy, such as polyethylene glycol and other natural or synthetic polymers (Harris J M and Chess R B, 2003; Greenwald R B et al., 2003; Pillai O and Panchagnula R, 2001). In this regard, the present invention contemplates chemically modified polypeptides and proteins as disclosed herein, in which the polypeptide or the protein is linked with a polymer. Typically, the polymer is water soluble so that the conjugate does not precipitate in an aqueous environment, such as a physiological environment. An example of a suitable polymer is one that has been modified to have a single reactive group, such as an active ester for acylation, or an aldehyde for alkylation. In this way, the degree of polymerization can be controlled. An example of a reactive aldehyde is polyethylene glycol propionaldehyde, or mono-(C1-C10) alkoxy, or aryloxy derivatives thereof (see, for example, U.S. Pat. No. 5,252,714). The polymer may be branched or unbranched. Moreover, a mixture of polymers can be used to produce the conjugates. The conjugates used for therapy can comprise pharmaceutically acceptable water-soluble polymer moieties. Suitable water-soluble polymers include polyethylene glycol (PEG), monomethoxy-PEG, mono-(C1-C10) alkoxy-PEG, aryloxy-PEG, poly-(N-vinyl pyrrolidone) PEG, tresyl monomethoxy PEG, PEG propionaldehyde, bis-succinimidyl carbonate PEG, propylene glycol homopolymers, a polypropyleneoxide/ethylene oxide co-polymer, polyoxyethylated polyols (e.g., glycerol), polyvinyl alcohol, dextran, cellulose, or other carbohydrate-based polymers. Suitable PEG may have a molecular weight from about 600 to about 60,000, including, for example, 5,000, 12,000, 20,000 and 25,000. A conjugate can also comprise a mixture of such water-soluble polymers. As an illustration, the Evasin-3 polypeptide or variant of the present invention can be modified with PEG, a process known as "PEGylation." PEGylation can be carried out by any of the PEGylation reactions known in the art (see, for example, EP 0 154 316). For example, PEGylation can be performed by an acylation reaction or by an alkylation reaction with a reactive polyethylene glycol molecule. In an alternative approach, conjugates are formed by condensing activated PEG, in which a terminal hydroxy or amino group of PEG has been replaced by an activated linker (see, for example, U.S. Pat. No. 5,382,657). The PEG may be linear or branched. It stabilizes the protein, may increase the half-life and improve the bioactivity.

These Evasin-3-derived compounds may be produced following a site-directed modification of an appropriate residue, in an internal or terminal position. Residues can be used for attachment, provided they have a side-chain amenable for polymer attachment (i.e., the side chain of an amino acid bearing a functional group, e.g., lysine, aspartic acid, glutamic acid, cysteine, histidine, etc.). Alternatively, a residue at these sites can be replaced with a different amino acid having a side chain amenable for polymer attachment.

For example, an additional Cysteine allowing direct PEGylation can be added at the N- or C-terminus of the mature protein sequence by recombinant DNA technologies or enzymatically. Alternatively, the Cysteine may be included in the protein by the substitution of a residue, for example in correspondence of a glycosylation site.

In another aspect the present invention relates to antibodies that selectively bind the proteins of the invention.

The term "antibody" as used herein encompasses monoclonal and polyclonal antibodies, chimeric, humanized, fully human, bispecific or multispecific antibodies as well as fragments thereof such as single chain antibodies (scFv) or domain antibodies, as further explained below.

Within the context of this invention, the term "selective" binding indicates that the antibodies preferentially bind the target polypeptide or epitope, i.e., with a higher affinity than any binding to any other antigen or epitope. In other words, binding to the target polypeptide can be discriminated from non-specific binding to other antigens. It is preferred that the antibodies according to the present invention exhibit binding affinity (Ka) to the target polypeptide or epitope of $10^6 \, M^{-1}$ or greater, preferably $10^7 \, M^{-1}$ or greater, more preferably $10^8 \, M^{-1}$ or greater and most preferably $10^9 \, M^{-1}$ or greater. The binding affinity of an antibody can be readily determined by one of ordinary skill in the art, for example, by Scatchard analysis (Scatchard G., 1949).

Antibodies of this invention may be monoclonal or polyclonal antibodies, or fragments or derivative thereof having substantially the same antigen specificity.

Methods of preparing polyclonal antibodies from various species, including rodents, primates and horses, have been described for instance in Vaitukaitis et al (1971). Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the polypeptide of SEQ ID NO 5, 6, 17, 18 or a variant as described hereabove or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). Repeated injections may be performed. Blood samples are collected and immunoglobulins or serum are separated.

The antibodies may, alternatively, be monoclonal antibodies. The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. The modifier "monoclonal" indicates the character of the antibody as being obtained from a substantially homogeneous population of antibodies, and is not to be construed as requiring production of the antibody by any particular method.

Methods of producing monoclonal antibodies may be found, for instance, in Kohler et al (Nature 256 (1975) 495), incorporated therein by reference.

In a hybridoma method, a mouse, hamster, or other appropriate host animal, is typically immunized with an immunizing agent (the immunizing agent will typically include the polypeptide of SEQ ID NO: 5, 6, 17, 18 or a variant as described hereabove or a fusion protein thereof or an expression vector containing the coding sequence of said protein) to elicit lymphocytes that produce or are capable of producing antibodies that will specifically bind to the immunizing agent. Alternatively, the lymphocytes may be immunized in vitro. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding 1986). Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells. Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies.

The culture medium in which the hybridoma cells are cultured can then be assayed for the presence of monoclonal antibodies directed against the immunizing peptide. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art.

After the desired hybridoma cells are identified, the clones may be subcloned by limiting dilution procedures and grown by standard methods (Goding, supra). Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells.

The "monoclonal antibodies" may also be isolated from phage antibody libraries using the techniques described in Clackson et al., 1991 and Marks et al, 1991.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

Antibodies may also be produced by selection of combinatorial libraries of immunoglobulins, as disclosed for instance in Ward et al (1989).

The antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of non-human species (donor antibody) such as mouse, rat or rabbit having the desired specificity, affinity and capacity. In some instances, Fv framework residues of the human immunoglobulin are replaced by corresponding non-human residues.

Methods for humanizing non-human antibodies are well known in the art. Humanization can be essentially performed following the method of Winter and co-workers (Jones et al., Nature, 321:522-525 (1986)), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species.

Human antibodies can also be produced using various techniques known in the art, including phage display libraries (Hoogenboom and Winter, (1991). Similarly, human antibodies can be made by the introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016

The invention also pertains to immunoconjugates comprising an antibody conjugated to heterologous moieties, such as cytotoxic agents, labels, drugs or other therapeutic agents, covalently bound or not, either directly or through the use of coupling agents or linkers. Cytotoxic agent include chemotherapeutic agent, toxin (e.g., an enzymatically active toxin of bacterial, fungal, plant, or animal origin, or fragments thereof), or a radioactive isotope (i.e., a radioconjugate).

Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re.

In another embodiment, the antibody may be conjugated to a "receptor" (such as streptavidin) for utilization in tumor pretargeting wherein the antibody-receptor conjugate is administered to the patient, followed by removal of unbound conjugate from the circulation using a clearing agent and then administration of a "ligand" (e.g., avidin) that is conjugated to a cytotoxic agent (e.g., a radionucleotide).

Moreover, antibodies or antibody fragments of the present invention can be PEGylated using methods in the art and described herein. The antibodies disclosed herein may also be formulated as immunoliposomes. Liposomes with enhanced circulation time are disclosed in U.S. Pat. No. 5,013,556.

The invention also pertains to "Antibody fragments" which comprise a portion of an intact antibody, preferably the antigen binding or variable region of the intact antibody. Examples of antibody fragments include Fab, Fab', F(ab')2, and Fv fragments; diabodies; linear antibodies; single-chain antibody molecules; monobodies; diabodies; camelized monobodies; domain antibodies and multispecific antibodies formed from antibody fragments.

"Fv" is the minimum antibody fragment which contains a complete antigen-recognition and binding site. This region consists of a dimer of one heavy and one light-chain variable domain in tight, non-covalent association. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen.

The Fab fragment also contains the constant domain of the light chain and the first constant domain (CH1) of the heavy chain. Fab fragments differ from Fab' fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known. The "light chains" of antibodies (immunoglobulins) from any vertebrate species can be assigned to one of two clearly distinct types, called kappa and lambda, based on the amino acid sequences of their constant domains.

"Single-chain antibody molecules" are fragments of an antibody comprising the VH and VL domains of said antibody, wherein these domains are present in a single polypeptide chain. Preferably, the Fv polypeptide further comprises a polypeptide linker between the VH and VL domains which enables the single-chain antibody molecule to form the desired structure for antigen binding.

The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161.

The term "monobody" as used herein, refers to an antigen binding molecule with a heavy chain variable domain and no light chain variable domain. A monobody can bind to an antigen in the absence of light chains and typically has three CDR regions designated CDRH1, CDRH2 and CDRH3. A heavy chain IgG monobody has two heavy chain antigen binding molecules connected by a disulfide bond. The heavy chain variable domain comprises one or more CDR regions, preferably a CDRH3 region.

A "camelized monobody" refers to a monobody or antigen binding portion thereof obtained from a source animal of the camelid family, including animals with feet with two toes and leathery soles. Animals in the camelid family include camels, llamas, and alpacas. It has been reported that camels (*Camelus dromedaries* and *Camelus bactrianus*) often lack variable light chain domains when IgG-like material from their serum is analyzed, suggesting that sufficient antibody specificity and affinity can be derived from VH domains (three CDR loops) alone.

Also included into the invention are single domain antibodies. Single domain antibodies, also called domain antibodies or dAbs, are the smallest functional binding units of antibodies, corresponding to the variable regions of either the heavy (VH) or light (VL) chains of human antibodies. Domain antibodies have a molecular weight of approximately 13 kDa, or less than one-tenth the size of a full antibody. In contrast to conventional antibodies, domain antibodies are well expressed in bacterial, yeast, and mammalian cell systems. In addition, many domain antibodies are highly stable and retain activity even after being subjected to harsh conditions, such as freeze-drying or heat denaturation which makes them amenable to a wide range of pharmaceutical formulation conditions and manufacture processes.

The proteins of the invention can be provided in more or less purified forms. The examples show how to clone nucleic acids necessary for expressing recombinant Evasin-3, how to purify recombinant or natural Evasin-3 using the affinity for CXC-chemokines and chromatographic technologies, and how to select cells properly expressing this protein by means of assays for detecting CXC-chemokine binding activities, in particular CXCL8 binding activities.

In particular, purification of the natural, synthetic or recombinant antagonists of the invention can be carried out by any one of the methods known for this purpose, i.e. any conventional procedure involving extraction, precipitation, chromatography, electrophoresis, or the like. A further purification procedure that may be used in preference for purifying the protein of the invention is affinity chromatography using monoclonal antibodies or affinity groups, which bind the target protein and which are produced and immobilized on a gel matrix contained within a column. Impure preparations containing the proteins are passed through the column. The protein will be bound to the column by heparin or by the specific antibody while the impurities will pass through. After washing, the protein is eluted from the gel by a change in pH or ionic strength. Alternatively, HPLC (High Performance Liquid Chromatography) can be used. The elution can be carried using a water-acetonitrile-based solvent commonly employed for protein purification. Purified preparations of the proteins of the Invention, as used herein, refers to the preparations which are at least 1% (by dry weight), and preferably at least 5%, of said proteins.

Another aspect of the present invention is a pharmaceutical composition comprising an Evasin-3 polypeptide as defined above (in the form of proteins and their alternative forms described above) as active ingredient, and a suitable diluent or carrier.

Another aspect of the present invention is a pharmaceutical composition comprising a nucleic acid molecule encoding an Evasin-3 polypeptide as defined above, or a corresponding vector or recombinant host cell, and a suitable diluent or carrier.

A further aspect of this invention relates to the use of an Evasin-3 polypeptide as defined above, or a nucleic acid encoding the same, for the manufacture of a medicament for use in regulating an immune response in a subject.

These compositions can be used as medicaments, in particular, for regulating an immune or inflammatory response in a mammal, and more particularly as anti-inflammatory compounds.

In general, given the involvement of CXC-chemokines in many human and veterinary disorders, the CXC-chemokine binding proteins of the invention can be used as antagonists of CXC-chemokines for the treatment or prevention of CXC-chemokine-related disorders in animals. A non-exhaustive list of CXC-chemokine-related disorders includes: inflammatory diseases, autoimmune diseases, immune diseases, infections, allergic diseases, cardiovascular diseases, metabolic diseases, gastrointestinal diseases, neurological diseases, sepsis, diseases related to transplant rejection, or fibrotic diseases. Non-limiting examples of these diseases are the following: arthritis, rheumatoid arthritis (RA), psoriatic arthritis, psoriasis, rheumatoid arthritis, restenosis, sepsis, osteoarthritis, systemic lupus erythematosus (SLE), systemic sclerosis, scleroderma, polymyositis, glomerulonephritis, fibrosis, allergic or hypersensitivity diseases, dermatitis, asthma, chronic obstructive pulmonary disease (COPD), inflammatory bowel disease (IBD), Crohn's disease, fibromas, ulcerative colitis, multiple sclerosis, septic shock, viral infection, cancer, endometriosis, transplantation, graft-versus-host disease (GVHD) cardiac and renal reperfusion injury, and atherosclerosis.

In particular, the CXC-chemokine binding proteins of the invention can be used for the treatment or prevention of psoriasis.

The proteins of the invention, or specific fragments, can be used as active ingredients in the manufacture of pharmaceutical compositions for regulating an immune or inflammatory response in a mammal, for example of anti-inflammatory compositions. Alternatively, the proteins of the invention, or specific fragments, can be used as active ingredients in the manufacture of pharmaceutical compositions for the vaccination of a mammal against parasites, virus, or bacteria. The process for the preparation of such pharmaceutical compositions comprises combining Evasin-3 together with a pharmaceutically acceptable diluent or carrier.

A pharmaceutical composition containing a protein of the invention as active ingredient can be used for binding a CXC-chemokine in vivo, blocking the binding of a CXC-chemokine to a corresponding cell surface receptor and consequently producing a potentially therapeutic effect, such as an anti-inflammatory effect. A pharmaceutical composition containing a protein of the invention as active ingredient, can be used also for binding to CXC-chemokine analogues present in viruses, bacteria, or parasites to block entry of said virus, bacteria, or parasite into cells. Pharmaceutical compositions for vaccination of a mammal against a parasite, a virus or a bacteria, can comprise a fragment of the protein of the invention as active ingredient. The compositions above indicated can further comprise an additional immunosuppressant or anti-inflammatory substance.

The pharmaceutical compositions may contain, in combination with the proteins of the invention as active ingredient, suitable pharmaceutically acceptable diluents, carriers, biologically compatible vehicles and additives which are suitable for administration to an animal (for example, physiological saline solution) and eventually comprising auxiliaries (like excipients, stabilizers, or adjuvants) which facilitate the processing of the active compounds into preparations which can be used pharmaceutically. The pharmaceutical compositions may be formulated in any acceptable way to meet the needs of the mode of administration. For example, the use of biomaterials and other polymers for drug delivery, as well the different techniques and models to validate a specific mode of administration, are disclosed in literature (Luo B and Prestwich G D, 2001; Cleland J L et al., 2001).

"Pharmaceutically acceptable" is meant to encompass any carrier, which does not interfere with the effectiveness of the biological activity of the active ingredient and that is not toxic to the host to which is administered. For example, for parenteral administration, the above active ingredients may be formulated in unit dosage form for injection in vehicles such as saline, dextrose solution, serum albumin and Ringer's solution. Carriers can be selected also from starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the various oils, including those of petroleum, animal, vegetable or synthetic origin (peanut oil, soybean oil, mineral oil, sesame oil).

Any accepted mode of administration can be used and determined by those skilled in the art to establish the desired blood levels of the active ingredients. For example, administration may be by various parenteral routes such as subcutaneous, intravenous, intradermal, intramuscular, intraperitoneal, intranasal, transdermal, rectal, oral, or buccal routes. The pharmaceutical compositions of the present invention can also be administered in sustained or controlled release dosage forms, including depot injections, osmotic pumps, and the like, for the prolonged administration of the polypeptide at a predetermined rate, preferably in unit dosage forms suitable for single administration of precise dosages.

Parenteral administration can be by bolus injection or by gradual perfusion over time. Preparations for parenteral administration include sterile aqueous or non-aqueous solutions, suspensions, and emulsions, which may contain auxiliary agents or excipients known in the art, and can be prepared according to routine methods. In addition, suspension of the active compounds as appropriate oily injection suspensions may be administered. Suitable lipophilic solvents or vehicles include fatty oils, for example, sesame oil, or synthetic fatty acid esters, for example, sesame oil, or synthetic fatty acid esters, for example, ethyl oleate or triglycerides. Aqueous injection suspensions that may contain substances increasing the viscosity of the suspension include, for example, sodium carboxymethyl cellulose, sorbitol, and/or dextran. Optionally, the suspension may also contain stabilizers. Pharmaceutical compositions include suitable solutions for administration by injection, and contain from about 0.01 to 99.99 percent, preferably from about 20 to 75 percent of active compound together with the excipient.

It is understood that the dosage administered will be dependent upon the age, sex, health, and weight of the recipient, kind of concurrent treatment, if any, frequency of treatment, and the nature of the effect desired. The dosage will be tailored to the individual subject, as is understood and determinable by one of skill in the art. The total dose required for each treatment may be administered by multiple doses or in a single dose. The pharmaceutical composition of the present invention may be administered alone or in conjunction with other therapeutics directed to the condition, or directed to other symptoms of the condition. Usually a daily dosage of active ingredient is comprised between 0.01 to 100 milligrams per kilogram of body weight per day. Ordinarily 1 to 40 milligrams per kilogram per day given in divided doses or in sustained release form is effective to obtain the desired results. Second or subsequent administrations can be performed at a dosage, which is the same, less than, or greater than the initial or previous dose administered to the individual.

Another aspect of the invention is the use of a protein encoded by a DNA of the Invention as a medicament, in particular in the preparation of a composition for regulating an immune or inflammatory response in a mammal.

Further aspects of the Invention are methods for immunising an animal against a blood-feeding ectoparasite, or for regulating an immune or inflammatory response in an animal in need thereof, comprising administering to said animal with a protein of the Invention said animal for a time and under conditions sufficient to regulate said immune response.

Another aspect of the invention is a method for treating or preventing CXC-chemokine-related diseases comprising the administration of an effective amount of the compounds of the present invention.

An "effective amount" refers to an amount of the active ingredients that is sufficient to affect the course and the severity of the disease, leading to the reduction or remission of such pathology. The effective amount will depend on the route of administration and the condition of the patient.

The wording "CXC-chemokine-related diseases" indicates any disease due to an excessive or uncontrolled CXC-chemokine production, leading to a massive monocyte/macrophage/neutrophil/T-cell infiltration, and wherein the administration of Evasin-3 may provide a beneficial effect. A non-exhaustive list of such chronic, acute, or inherited diseases is provided above.

The therapeutic applications of the CXC-chemokine antagonists of the invention and of the related reagents can be evaluated (in terms or safety, pharmacokinetics and efficacy) by the means of in vivo or in vitro assays making use of mammalian cells, tissues and models (Coleman R et al., 2001; Li A, 2001; Methods Mol. Biol. vol. 138, "Chemokines Protocols", edited by Proudfoot A et al., Humana Press Inc., 2000; Methods Enzymol, vol. 287 and 288, Academic Press, 1997). A non-limiting list of assays includes: calcium mobilisation, degranulation, upregulation of pro-inflammatory cytokines, upregulation of proteases, inhibition of cellular recruitment in vitro and in vivo.

Further aspects of the invention are test kits containing any of the compound disclosed in association to the CXC-chemokine binding proteins of the invention. For example, a kit for detecting a CXC-chemokine or an analogue, a CXC-chemokine binding protein or a receptor, the interaction of CXC-chemokine and a CXC-chemokine binding protein, or antagonists or agonists of said interaction, comprising a detecting reagent and at least a compound selected from the group consisting of:
  a) A nucleic acid molecule (e.g., a DNA);
  b) An oligonucleotide;
  c) A protein; and
  d) An antibody;
derived from the CXC-chemokine binding protein of the Invention.

These kits can be used in methods applicable in vitro or in vivo in which a sample is contacted by one of these compounds, which can be labeled or immobilized on a solid support.

The present invention has been described with reference to the specific embodiments, but the content of the description comprises all modifications and substitutions, which can be brought by a person skilled in the art without extending beyond the meaning and purpose of the claims.

The invention will now be described by means of the following Examples, which should not be construed as in any way limiting the present invention. The Examples will refer to the Figures specified here below.

EXAMPLES

Example 1

Screening of the *Rhipicephalus sanguineus* cDNA Library for CXC-Chemokine Binding Activities and Cloning of Evasin-3

Materials and Methods b. Construction of the *Rhipicephalus sanguineus* cDNA Library and of the Control Plasmid Expressing vCCI Salivary glands were harvested from 100 adult ticks (*Rhipicephalus sanguineus*) and were immediately stored in ice-cold RNAlater™ solution (Ambion) until further use. Total RNA was extracted using the TRIzol™ method (Invitrogen) according to the manufacturer's instructions. The cDNA library was constructed in the phagemid vector λTriplEX2 using the SMART cDNA library construction kit (Clontech). The cDNAs were size-fractionated with a ChromaSpin 400 column (Clontech) according to the manufacturer's instructions before ligation to the vector. The size of the cloned cDNA inserts in the library ranged from about 0.6 kb to 1.5 kb and the frequency of inserts was approximately 80%.

The cDNA inserts from the *Rhipicephalus sanguineus* salivary gland cDNA library in pTriplEX2 were excised with restriction enzyme SfiI, and subcloned into the mammalian cell expression vector pEXP-lib (Clontech). The pEXP-Lib vector contains an expression cassette comprising the human cytomegalovirus (CMV) major immediate early promoter/enhancer followed by a multiple cloning site; an internal ribosome entry site (IRES) of the encephalomyocarditis virus (ECMV); a gene encoding puromycin resistance (puromycin-N-acetyl-transferase); and the polyadenylation signal of the bovine growth hormone. The multiple cloning site contains two distinct Sfi I sites (Sfi IA and Sfi IB, that differ in their interpalindromic sequences), which allows the directional subcloning of cDNA inserts from the pTriplEX2 vector to pEXPII.

The control protein vCCI (NCBI Acc. no. CAC05575; SEQ ID NO: 1) was expressed by cloning the cDNA encoding the protein (NCBI Acc. no. AJ277111; SEQ ID NO: 2) into pEXP-lib as described above to generate pEXP-lib vCCI.

c. Library Screening Using HEK293 Cells Supernatants

Human embryonic kidney cells 293 (HEK293 cells; ATCC Cat. No. CRC-1573) were maintained in DMEM-F12 Nut Mix, 10% heat-inactivated fetal calf serum, 2 mM L-Glutamine, 100 units/ml penicillin-streptomycin solution.

The pEXP-lib plasmids expressing *Rhipicephalus sanguineus* cDNA library were grouped into pools that were transfected into HEK293 cells using a GenePorter2 transfection kit (Gene Therapy Systems) according to the manufacturer's protocol. The pEXP-lib plasmid expressing the control protein vCCI was transfected into HEK293 in the same manner.

Culture medium from transfected HEK293 cells was harvested from cells grown in complete medium after three days in culture. The conditioned medium was centrifuged to remove cell debris, and the supernatant used in a cross-linking assay.

For cross-linking experiments conditioned media samples were transferred to a 96-well plate (Costar). A radiolabeled CC-chemokine ($^{125}$I-CXCL8/IL-8) was added to a final concentration of 0.23 nM to 50 µl of each sample of supernatant, and incubated with shaking for 1 hour at room temperature. A 25 µl aliquot from each well was then transferred to a new well containing 5 µl of 25 mM BS3 (cross-linking reagent) and further incubated for 1 hour with shaking. After this time 5 µl of 10× sample buffer (125 mM Tris base, pH 6.8, containing 10% SDS, 5 mM EDTA, 20% glycerol, 0.2% w/w bromophenol blue, 1 M DTT) were added to each well to stop the cross-linking reaction. The samples were then boiled for 5 minutes and electrophoresed on a 10% Bis-Tris SDS-polyacrylamide gel (Invitrogen NuPAGE, catalog no. NP0301 BOX). After electrophoresis the gel was sealed in Saran wrap™ and exposed to a K-type storage phosphoimaging screen (Biorad) for 3 to 16 hours. Imaging screens were scanned at a resolution of 100 µm using a Biorad Personal FX phosphoimager.

Results

The saliva of the tick *Rhipicephalus sanguineus* has been shown to contain immunomodulating activities, such as suppression of IgG and cytokine production (Matsumoto K et al., 2003) or T cell proliferation (Ferreira B R and Silva J S, 1998), but not activities directed specifically to CC- or CXC-chemokines. However chemokine binding activity has been detected in the saliva of other tick species (Hajnicka et al., 2005)

In order to detect a CXC-chemokine binding activity in *Rhipicephalus sanguineus* at the DNA/protein sequence level a cDNA library was generated from *Rhipicephalus sanguineus* salivary glands. Pools of the cDNAs from this library were used to transfect mammalian cells (HEK293).

In this system cDNAs which encode secreted proteins are expressed by the HEK293 cells and secreted into the culture medium. The supernatants can be tested directly, in a cross-linking assay using a radio-labeled CXC-chemokine ($^{125}$I-CXCL8/IL-8). The addition of the cross-linking reagent to the radio-labeled CXC-chemokine/CXC-chemokine binding protein stabilizes the protein complex by linking the two molecules covalently. The resulting complex can be identified by SDS-polyacrylamide gel electrophoresis (SDS-PAGE) and subsequent autoradiography as a band shift from the molecular weight of the native chemokine to the molecular weight of the complex. This cross-linking method is highly sensitive as nanogram amounts of protein can be detected.

As a positive control, conditioned medium from HEK cells transfected with vCCI was tested in parallel. As a negative control, conditioned medium from mock transfected HEK 293 cells was used. cDNA pools which gave rise to a positive signal in the cross linking assay were subjected to successive rounds of screening and deconvolution until a single transfected cDNA responsible for the CXC-chemokine binding activity could be identified. The resultant cDNA was called Evasin-3 (FIG. 1).

The cDNA encoding Evasin-3 (SEQ ID NO: 3) contains an Open Reading Frame (ORF; SEQ ID NO: 4) encoding a protein of 92 amino acids (SEQ ID NO: 5). The protein sequence is predicted to contain a signal peptide sequence (residues 1-26), which when cleaved generates a mature protein of 66 amino acids (SEQ ID NO: 6). Evasin 3 has no significant homology with any known proteins.

Further features of Evasin-3 are 2 potential glycosylation sites (at Asparagine 51, and 82, according to the numbering of the full protein), and a series of Cysteines that can be paired to form disulfide bridges (residues 48, 52, 59, 63, 65 and 76, according to the numbering of the full protein).

Example 2

Purification and Characterization of Evasin-3 Expressed in HEK293 EBNA Cell Culture Supernatant as a 6His-Tagged Recombinant Protein Materials and Methods a. Subcloning of Evasin-3 cDNA into the Expression Vectors pDEST8 and pEAK12d Using the Gateway™ Cloning Process The first stage of the Gateway cloning process involves a two step PCR reaction (PCR1 and PCR2) which generates the ORF of Evasin-3 flanked at the 5' end by an attB1 recombination site and Kozak sequence, and flanked at the 3' end by a sequence encoding an in frame 6 Histidine (6His) tag, a stop codon and the attB2 recombination site (Gateway compatible cDNA; FIG. 2). The PCR 1 reaction (in a final volume of 50 µl) contains: 2 µl of pEXP-Lib-Evasin-3, 3 µl dNTPs (5 mM), 5 µl of 10×Pfx polymerase buffer, 1 µl MgSO$_4$ (50 mM), 1.5 µl each of gene specific primer (10 µM) (evasin3 PCR1F (SEQ ID NO: 7) and evasin3 PCR1R; SEQ ID NO: 8), and 0.5 µl Platinum Pfx DNA polymerase (Invitrogen). The 1$^{st}$ PCR reaction was performed using an initial denaturing step of 95° C. for 2 minutes, followed by 10 cycles of 94° C. for 30 s; 48° C. for 30 s and 68° C. for 1 min 30 s; and a holding cycle of 4° C. The amplification products were purified directly using the QIAquick PCR Purification Kit (QIAGEN). The PCR product was eluted in 50 µl EB buffer (10 mM Tris-HCl, pH 8.5) according to the manufacturer's instructions.

The second PCR reaction (in a final volume of 50 µl) contained 10 µl purified PCR1 product, 3 µl dNTPs (5 mM), 10 µl of 10×Pfx polymerase buffer, 1 µl MgSO$_4$ (50 mM), 1.5 µl of each Gateway conversion primer (10 µM) (evasin3 PCR2F, SEQ ID NO: 9) and evasin3 PCR2 R; SEQ ID NO:10) and 0.5 µl of Platinum Pfx DNA polymerase. The conditions for the second PCR reaction were: 95° C. for 1 min; 4 cycles of 94° C. for 15 seconds, 50° C. for 30 seconds and 68° C. for 2 min; 20 cycles of 94° C. for 15 seconds, 55° C. for 30 seconds, and 68° C. for 1 min; and a holding cycle at 4° C. The resultant PCR products were visualized on a 1.5% agarose gel in 1×TAE buffer (Invitrogen) and a band migrating at the predicted molecular mass (430 bp) was purified from the gel using the QIAquick Gel Extraction Kit (QIAGEN) and eluted in 50 µl EB Buffer according to the manufacturer's instructions.

The second stage of the Gateway cloning process involves subcloning of the Gateway modified PCR product into the Gateway entry vector pDONR221. Five µl of purified PCR2 product were incubated with 1.5 µl pDONR221 vector (0.1 µl/µl), 2 µl BP buffer and 1.5 µl of BP clonase enzyme mix (Invitrogen) in a final volume of 10 µl at room temperature for 1 hour. The reaction was stopped by addition of proteinase K 1 µl (2 µg/µl) and incubated at 37° C. for a further 10 min. An aliquot of this reaction (1 µl) was used to transform *E. coli* DH10B cells by electroporation as follows: a 20 µl aliquot of DH10B electrocompetent cells (Invitrogen) was thawed on ice and 1 µl of the BP reaction mix was added. The mixture was transferred to a chilled 0.1 cm electroporation cuvette and the cells electroporated using a BioRad Gene-Pulser™ according to the manufacturer's protocol. SOC medium (1 ml), which had been pre-warmed to room temperature, was added immediately after electroporation. The mixture was transferred to a 15 ml snap-cap tube and incubated, with shaking (220 rpm) for 1 hour at 37° C. Aliquots of the transformation mixture (10 µl and 100 µl) were then plated on L-broth (LB) plates containing kanamycin (40 µl/ml) and incubated overnight at 37° C.

Plasmid mini-prep DNA was prepared from 5 ml cultures from 4 of the resultant kanamycin resistant colonies using a Qiaprep Turbo 9600 robotic system (Qiagen). Plasmid DNA (200-500 ng) was subjected to DNA sequencing with 21M13 and M13Rev primers using the BigDyeTerminator system (Applied Biosystems cat. no. 4336919) according to the manufacturer's instructions. Sequencing reactions were purified using Montage SEQ 96 cleanup plates (Millipore cat. no. LSKS09624) then analyzed on an Applied Biosystems 3700 DNA sequencer.

Plasmid eluate (1.5 µl or approx. 100 ng) from one of the clones, which contained the correct sequence (pDONR221_Evasin-3-HIS, FIG. 3A) was then used in recombination reactions containing 1.5 µl of either pDEST8 vector or pEAK12d vector (0.1 µg/µl), 2 µl LR buffer and 1.5 µl of LR clonase (Invitrogen) in a final volume of 10 µl. The mixtures were incubated at room temperature for 1 hour. The reactions were stopped by addition of Proteinase K (2 µg) and incubated at 37° C. for a further 10 minutes. An aliquot of each reaction (1 µl) was used to transform *E. coli* DH10B cells by electroporation as follows: a 20 μl aliquot of DH10B electrocompetent cells (Invitrogen) was thawed on ice and 1 μl of the LR reaction mix was added. The mixture was transferred to a chilled 0.1 cm electroporation cuvette and the cells electroporated using a BioRad Gene-Pulser™ according to the manufacturer's recommended protocol. SOC media (1 ml), which had been pre-warmed to room temperature, was added immediately after electroporation. The mixture was transferred to a 15 ml snap-cap tube and incubated, with shaking (220 rpm) for 1 hour at 37° C. Aliquots of the transformation mixture (10 μl and 100 μl) were then plated on L-broth (LB) plates containing ampicillin (100 μg/ml) and incubated overnight at 37° C.

Plasmid mini-prep DNA was prepared from 5 ml cultures inoculated with 6 of the resultant ampicillin-resistant colonies subcloned into each vector using a Qiaprep Bio Robot 8000 (Qiagen). Plasmid DNA (200-500 ng) in the pEAK12d vector was subjected to DNA sequencing with pEAK12F (SEQ ID NO: 11) and pEAK12R primers (SEQ ID NO:12). Similarly, plasmid DNA (200-500 ng) in the pDEST8 vector was subjected to DNA sequencing with pDEST8F (SEQ ID NO: 13) and pDEST8R primers (SEQ ID NO: 14) as described above.

Plasmid maxi-prep DNA was prepared from a 500 ml culture of the sequence verified clones (pEAK12d_Evasin-3-HIS and pDEST8_Evasin-3-HIS) (FIGS. 3C and 3B respectively) using Qiagen Plasmid MEGA Kit (QIAGEN) according to the manufacturer's instructions. Plasmid DNA was resuspended at a concentration of 1 μl/μl in sterile water (or 10 mM Tris-HCl pH 8.5) and stored at −20° C.

The primer sequences used in the different sub-/cloning steps are summarized in Table III.

b. Insertion of a 6His Tag at the C Terminal of the ORF Sequence of the pEXPII-evasin3 Plasmid Using Quik-Chamge II Site-Directed Mutagenesis Kit (Stratagene).

The first stage of the site directed mutagenesis process involves a PCR reaction which generates a mutated plasmid with the ORF of Evasin-3 flanked at the 3' end by a sequence encoding an in frame 6 Histidine (6His) tag. The PCR reaction (in a final volume of 50 μl) contains: 1 μl (50 ng) of plasmid pEXP-Lib-Evasin-3, 1 μl dNTP mix, 5 μl of 10× reaction buffer, 2 μl each of gene specific primer (62.5 μM) (evasin3-6HisF and evasin3-6His R; SEQ ID NO: 19 and 20), and 1 μl Pfu Ultra HF DNA polymerase according to the manufacturer's instructions. The PCR reaction was performed using an initial denaturing step of 95° C. for 30 s, followed by 18 cycles of 95° C. for 30 s; 55° C. for 1 minute and 68° C. for 5 min 30 s; and a holding cycle of 4° C.

The second stage of the site directed mutagenesis process involves the treatment of the PCR product with the Dpn1 endonuclease, specific for methylated and hemimethylated DNA, to digest the parental methylated plasmid DNA and to select for mutation containing newly synthesized DNA. The PCR product was incubated with 1 μl Dpn1 restriction enzyme (10 U/μl) at 37° C. for 1 hour, according to manufacturer's instructions.

An aliquot of Dpn1 restriction digest reaction (1 μl) was used to transform E. coli XL-1 blue cells by heat shock as follows: a 50 μl aliquot of XL-1 blue competent cells (Stratagene) was thawed on ice and 1 μl of the Dpn1 reaction mix was added. The mixture was incubated on ice for 30 min and cells were heat-shocked at 42° C. for 45 s. after the cells were transferred to an ice bath for 2 min. NZY medium (0.5 ml), which had been pre-warmed to 42° C., was then added. The mixture was transferred to a 15 ml snap-cap tube and incubated, with shaking (220 rpm) for 1 hour at 37° C. Aliquots of the transformation mixture (250 μl) were then plated on L-broth (LB) plates containing ampicillin (100 μg/ml) and incubated overnight at 37° C.

Plasmid mini-prep DNA was prepared from 5 ml cultures from 4 of the resultant colonies using a Qiaprep Turbo 9600 robotic system (Qiagen). Plasmid DNA (200-500 ng) was subjected to DNA sequencing with a T7 primer (SEQ ID NO: 16) using the BigDyeTerminator system (Applied Biosystems cat. no. 4336919) according to the manufacturer's instructions. Sequencing reactions were purified using Montage SEQ 96 cleanup plates (Millipore cat. no. LSKS09624) then analyzed on an Applied Biosystems 3700 DNA sequencer.

Plasmid maxi-prep DNA was prepared from a 500 ml culture of the sequence verified clone (pEXPII_Evasin-3-HIS) (FIG. 3D) using Qiagen Plasmid MEGA Kit (QIAGEN) according to the manufacturer's instructions. Plasmid DNA was resuspended at a concentration of 1 μl/μl in sterile water (or 10 mM Tris-HCl pH 8.5) and stored at −20° C.

The primer sequences used in the different sub-/cloning steps are summarized in Table III.

C. Purification of Recombinant Evasin-3-HIS Expressed in HEK293 Cells

Cell culture supernatant 450 ml or 250 ml from HEK293-EBNA cells was harvested 6 days after transfection with either pEAK12d-Evasin-3-HIS or with pEXPII Evasin-3-HIS and diluted with 2 volumes of 50 mM sodium phosphate buffer pH 7.5 containing 0.6 M NaCl and 8.7% (vol/vol) glycerol. The sample was filtered through a 0.22 μm membrane filter, then loaded at 20 ml/min at 4° C. onto a metal chelate affinity column PORUS 20 MC of 4 ml (PerSeptive Biosystem) charged with $Ni^{2+}$ ions with a solution of 100 mM $Ni(II)SO_4$ (Fluka, ref 72280) using an Vision Workstation system (PerSeptive Biosystem). Non-specifically bound material was removed by washing the column at 20 ml/min with 28 column volumes (CVs) of 50 mM sodium phosphate buffer pH 7.5 containing 0.6 M NaCl, 8.7% glycerol (Catalogue No: 49781; Fluka) and 20 mM imidazole (Fluka, ref 56749). The column was eluted in 2.7 ml fractions with 5.5 CVs of 50 mM sodium phosphate buffer, pH 7.5, containing 0.6 M NaCl, 8.7% glycerol and 400 mM imidazole (Catalogue No: 56749; Fluka) at 2.0 ml/min. The eluted protein peak was desalted by size exclusion chromatography using a Sephadex G-25 column of 20 ml (Pharmacia) eluted in 2.7 ml fractions with 1 CV of PBS containing 20% glycerol.

Evasin-3-HIS-containing fractions were pooled and dialysed against 5 litres of 50 mM ammonium bicarbonate pH 8.0 for 16 h and then lyophilised using a Freeze-dryer mobile 12EL (Virtis) and resuspended in 100 μl sterile water. The concentrated pool was subjected to size exclusion chromatography as second step of purification. An SX200 10/300 GL column (bed volume of 25 ml; catalogue No: 17-5175-01; Amersham Biosciences), which was first equilibrated in 50 mM ammonium bicarbonate, was injected with 200 μl of the Evasin-3-HIS, diluted with 1 volume of 50 mM ammonium bicarbonate. The protein was eluted in fractions of 0.5 ml each at 2.5 ml/min. Evasin-3-HIS protein containing fractions were pooled, lyophilised, aliquoted, and stored at −80° C.

d. Western Blot, SDS-PAGE Cross-linking and Size Exclusion Chromatography Analysis of Recombinant Evasin-3-HIS For Western blot analysis the column eluates were diluted 1:3 with 3× sample buffer (bromophenol Blue with 125 mM Tris-HCl pH 6.8 containing 20% Glycerol, 10% SDS, 5 mM EDTA and 100 mM DTT) and boiled at 95° C. for 5 minutes.

The samples and a HIS-tagged molecular weight standard (Catalogue No: LC5606; Invitrogen) were electrophoresed on a 10% Bis-Tris gel run in MES-buffer at 200 V for 35 min. The electrophoresed proteins were electro-transferred onto a 0.45 μm nitrocellulose membrane (Catalogue No: LC2001; Invitrogen) in transfer buffer (39 mM glycine, 48 mM Tris base, and 20% methanol, pH 8.3) for 1 hour at room temperature, using a constant current of 290 mA. The membrane was blocked by incubating in 20 ml blocking solution (0.1% Tween 20, 5% milk powder in PBS), for 1 hour at room temperature on a rocker platform. The membrane was then incubated in 15 ml of the solution containing the primary anti-histidine tag antibody (diluted 1:1000 in 0.1% Tween 20, 2.5% milk powder in PBS) for 2 hours at room temperature with shaking. The primary antibodies used were His-probe H-15 (sc-803; Santa Cruz Biotechnology) or His-probe G-18 (sc-804; Santa Cruz Biotechnology). The membrane was rinsed with wash buffer (0.1% Tween 20 in PBS) and washed with 3 changes of wash buffer (10 minutes each). The membrane was then incubated in HRP-conjugated secondary antibody (diluted 1:3000 in PBS with 0.1% Tween 20, 2.5% milk powder) for 2 hours at room temperature with shaking. The membrane was washed again as described previously. Finally, the membrane was blotted dry, and antibody staining was visualized using the ECL™ Western Blotting Detection Reagents kit (Catalogue No: RPN2106; Amersham Pharmacia), according to manufacturer's instructions.

For SDS-PAGE analysis, the column eluates were diluted 1:1 with 2× sample buffer (Invitrogen) containing 100 mM DTT and boiled for 5 minutes. The samples and a molecular weight standard (Benchmark Protein Ladder; Invitrogen) were electrophoresed on a 10% Bis-Tris gel run in MES-buffer at 200 V for 35 min. The electrophoresed proteins were stained using Simply Blue SafeStain (Invitrogen) according to the manufacturer's instructions: the gel was rinsed three times with distilled water for 5 min, stained for 1 hour at room temperature and washed with water for 1 hour.

For cross-linking experiments, HEK 293 cells were transfected with pEAK12d-Evasin-3-6His. After 6 days, 50 μl of culture supernatant were transferred to a 96-well plate (Costar). Either a $^{125}$I-CC-chemokine ($^{125}$I-CCL5/RANTES, $^{125}$I-CCL11/eotaxin, CCL2/$^{125}$I-MCP-1, $^{125}$I-CCL17/TARC or $^{125}$I-CCL27/CTACK), a $^{125}$I-CXC-chemokine ($^{125}$I-CXCL8/IL-8, $^{125}$I-CXCL1/Gro-alpha or $^{125}$I-CXCL10/IP-10) or a cytokine ($^{125}$I-IL-1 or $^{125}$I-IL-2), was added to a final concentration of 0.23 nM, and incubated with shaking for 1 hour at room temperature. A 25 μl aliquot from each well was then transferred to a new well containing 5 μl of 25 mM BS3 (cross-linking reagent) and further incubated for 1 hour with shaking and the reaction quenched by the addition of 5 μl of 10× sample buffer (125 mM Tris base, pH 6.8, containing 10% SDS, 5 mM EDTA, 20% glycerol, 0.2% w/w bromophenol blue, 1 M DTT). The samples were then boiled for 5 minutes and electrophoresed on a 10% Bis-Tris SDS-polyacrylamide gel (Invitrogen NuPAGE, catalog no. NP0301BOX). After electrophoresis the gel was sealed in Saran Wrap™ and exposed to a K-type storage phosphoimaging screen (Biorad) for 3 to 16 hours. Imaging screens were scanned at a resolution of 100 μm using a Biorad Personal FX phosphoimager.

For the competition assay, the same protocol was used as for the cross-linking experiment described above using $^{125}$I-CXCL8/IL-8 with the addition of a 500 fold excess of unlabelled CXCL8/IL-8 or CXCL1/Gro-alpha.

Size exclusion chromatography (SEC) was performed with recombinant Evasin-3-6His and CXCL8/IL-8 suspended at 1 mg/ml in PBS. 100 μg (100 μl) of Evasin-3-6His were mixed in a 1:1 ratio with 100 μg (100 μl) of CXCL8/IL-8 and incubated for 1 h at room temperature to allow the formation of the complex: Evasin-3-6His-CXCL8/IL-8. Then, either 200 μg (200 μl) of CXCL8/IL-8, 200 μg (200 μl) of recombinant Evasin-3-6His or 200 μg (200 μl) of the complex were applied to Superdex 75 10/300 GL column (volume 23.56 ml, Invitrogen) previously equilibrated in 1×PBS over 1,5 CV. The column was previously calibrated with blue dextran (2000 kDa), thyroglobulin (669 kDa), ferritin (440 kDa), BSA (67 kDa), ovalbumin (43 kDa), ribonuclease A (13.7 kDa) and cytochrome C (13.6 kDa). The column was eluted over 1,5 CV with 1×PBS and the fractions corresponding to the peak were analyzed by SDS-PAGE with silver staining. For the SDS-PAGE analysis, the samples were diluted 3:1 with 4× sample buffer (Invitrogen) containing 100 mM DTT and boiled for 5 minutes. The samples and a molecular weight standard (Benchmark Protein Ladder; Invitrogen) were electrophoresed on a 10% Bis-Tris gel run in MES-buffer at 200 V for 35 min. The electrophoresed proteins were stained using SilverQuest kit (Invitrogen) according to the manufacturer's instructions. The gel was fixed with a solution of 40% Ethanol and 10% acetic acid, washed with a solution of 30% Ethanol, sensitized with a solution of 30% Ethanol and 10% sensitizer, washed twice with water, and stained with a solution of 1% stainer, washed with water, developed with a solution of 10% developer and stopped with the addition of 10% stopper.

Results

In order to produce recombinant evasin 3, the ORF was subcloned with or without a 6HIS tag sequence at the 3' end of the ORF into the mammalian cell expression vector pEAK12d or the insect cell expression vector (pDEST12.2) using the Gateway cloning system. In addition, the original pEXP_lib_evasin_3 construct was mutated by site directed mutagenesis to introduce a 6HIS tag sequence at the 3' end of the ORF for expression in HEK293 cells. Recombinant Evasin-3-HIS was purified from either pEAK12d-Evasin-3-6His transfected HEK293 EBNA cell supernatants or pEXPII-Evasin-3-6His-transfected HEK293 EBNA cell supernatants using Ni2+-affinity chromatography followed by size exclusion chromatography. The Coomassie blue staining of an SDS-PAGE gel in which the purified protein has been loaded suggests that Evasin-3-6HIS was expressed and purified as a mixture of differently post-translationally modified forms, possibly by glycosylation as shown for another tick protein expressed in insect cells (Alarcon-Chaidez F J et al., 2003). In fact, the protein appears as a smeared band, with an average molecular weight of around 20-30 Kd for the recombinant protein expressed in HEK293 (FIG. 4).

The presence of recombinant Evasin-3-6HIS during the different purification steps from HEK293 was followed by Western blot with anti-Histidine tag as primary antibodies. The N-terminal of the purified, mature sequence has been sequenced, confirming that the sequence LVSTIESR TS (SEQ ID NO: 27) forms the N-terminus of 80% of the mature protein with glycosylation on the S and T residues and that the sequence VSTIESRTSA (SEQ ID NO:28) forms the N-terminus of 20% of the mature protein without presence of glycosylation.

The CXC-chemokine binding activity of the purified Evasin-3-6HIS were compared with the activity observed using the positive control (the viral CC-chemokine binding protein vCCI) using the crosslinking assay used initially to characterize the activity in tick saliva from *Rhipicephalus sanguineus*.

Figure 4:
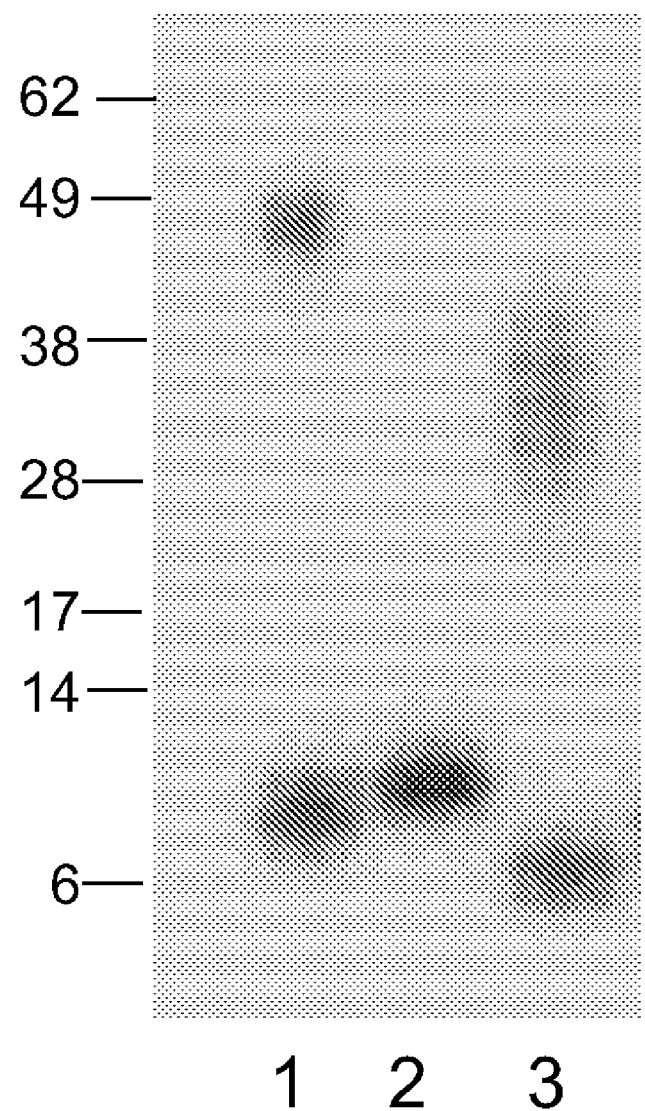
FIG. 4: Autoradiograph of the SDS-PAGE gel showing the complex formed by cross-linking of $^{125}$I-labeled CXC-chemokine CXCL8 (IL-8) with supernatants from HEK293 cells transfected with recombinant Evasin-3, using the cross-linker BS3. Lane 1, the viral CC-chemokine binding protein (p35) is cross-linked to $^{125}$I-eotaxin as a positive control; Lane 2, the viral CC-chemokine binding protein (p35) is incubated with $^{125}$I-eotaxin in the absence of BS3; Lane 3, HEK293 cell culture supernatant from the pool 69.19 incubated with $^{125}$I-CXCL8/IL-8 and BS3.
Figure 6:
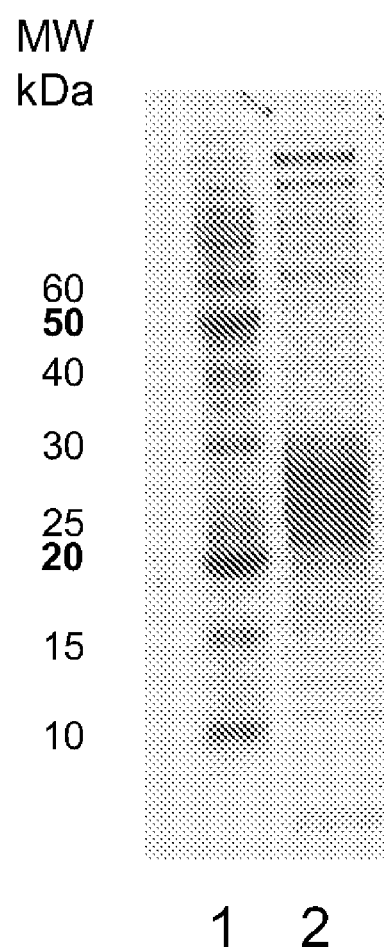
FIG. 6: 10% SDS-polyacrylamide gel (SDS-PAGE) stained with Coomassie blue showing Evasin-3-HIS purified from HEK293 cells using Ni$^{2+}$ affinity chromatography. Lane 1, Molecular weight markers; Lane 2, Recombinant Evasin-3-6His pool after elution from the Ni$^{2+}$ affinity column.

On SDS-PAGE analysis, the free $^{125}$I-labeled CXC-chemokine CXCL8/IL-8 migrates as an 8 kDa band (FIG. 4, Lane 2). When the crosslinking agent is added, a portion of the radioactivity is retained in a protein complex having a molecular weight of 28-40 kDa, in the sample containing recombinant Evasin-3 (FIG. 4, Lane 3). The band corresponding to the complex formed between the protein vCC1 and $^{125}$I-CCL2/MCP-1 used as a control for the crosslinking experiment migrates approximately at 45 kDa (FIG. 4, Lane 1). Given that the molecular weight for mature Evasin-3 polypeptide (66 amino acids) is 7005 Da, the recombinant protein appears to be active when expressed in eukaryotic host cells where it is post-translationally modified. These modifications may account for up to 20-30 kDa (as suggested also by the Coomassie staining in FIG. 6) and are probably due mostly to alternative glycosylation.

Figure 5:
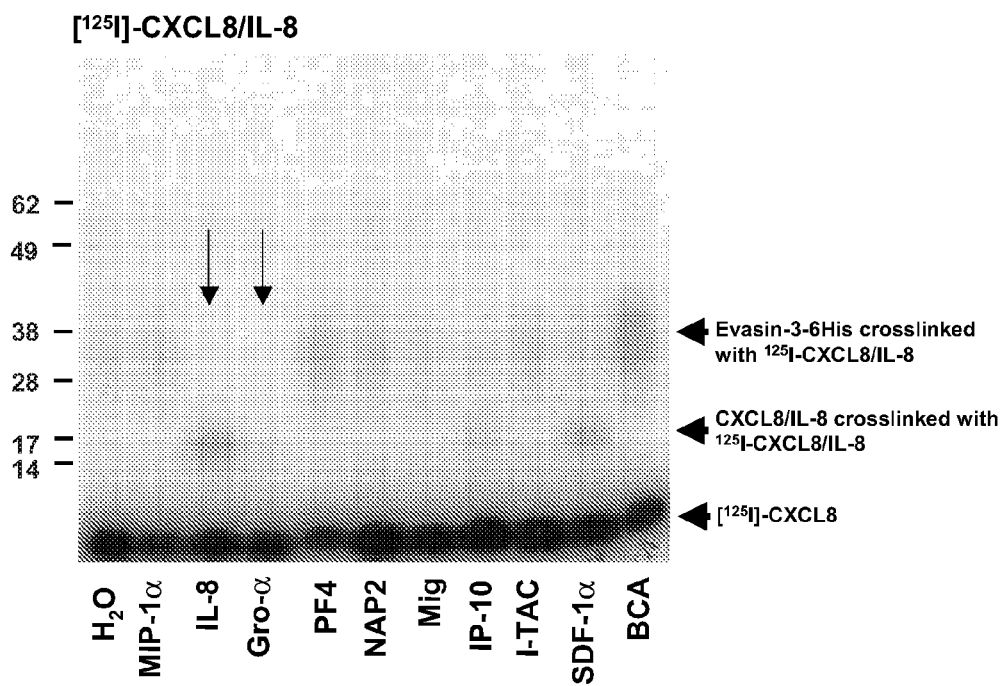
FIG. 5: Autoradiograph of the SDS-PAGE gel showing the competition for complex formation of unlabelled CXCL8/IL-8 and CXCL1/Gro-α with $^{125}$I-CXCL8/IL-8. The unlabeled proteins were added to the radio-labeled CXC-chemokine ($^{125}$I-CXCL8/IL-8) in presence of the cross-linking agent (BS$^3$). The molecular weight standards (M) (in Kd) are indicated on the left hand side of the gel. Lane 1, HEK293 cell supernatant expressing recombinant Evasin-3 cross-linked to $^{125}$I-CXCL8/IL-8; Lanes 2-11, HEK293 cell supernatant expressing recombinant Evasin-3 cross-linked to $^{125}$I-CXCL8/IL-8 in the presence of 1 μg unlabelled CCL3/MIP-1α (Lane 1), CXCL8/IL-8 (Lane 3), CXCL1/Gro-α (Lane 4), CXCL4/PF4 (Lane 5), CXCL7/NAP-2 (Lane 6), CXCL9/Mig (Lane 7), CXCL10/IP-10 (Lane 8), CXCL11 I-TAC (Lane 9), CXCL12/SDF-1α (Lane 10) or CXCL13/BCA-1 (Lane 11).

The selectivity of recombinant Evasin-3 was first tested in a competition assay for cross linking to $^{125}$I-CXCL8/IL-8. Both unlabelled CXCL8/IL-8 and CXCL1/Gro-alpha caused the disappearance of the radiolabelled complex (FIG. 5, indicated by arrows), thereby confirming the binding of recombinant Evasin-3 to CXCL1/Gro-alpha. None of the other chemokines tested caused disappearance of the radiolabelled complex (FIG. 5).

Figure 7:
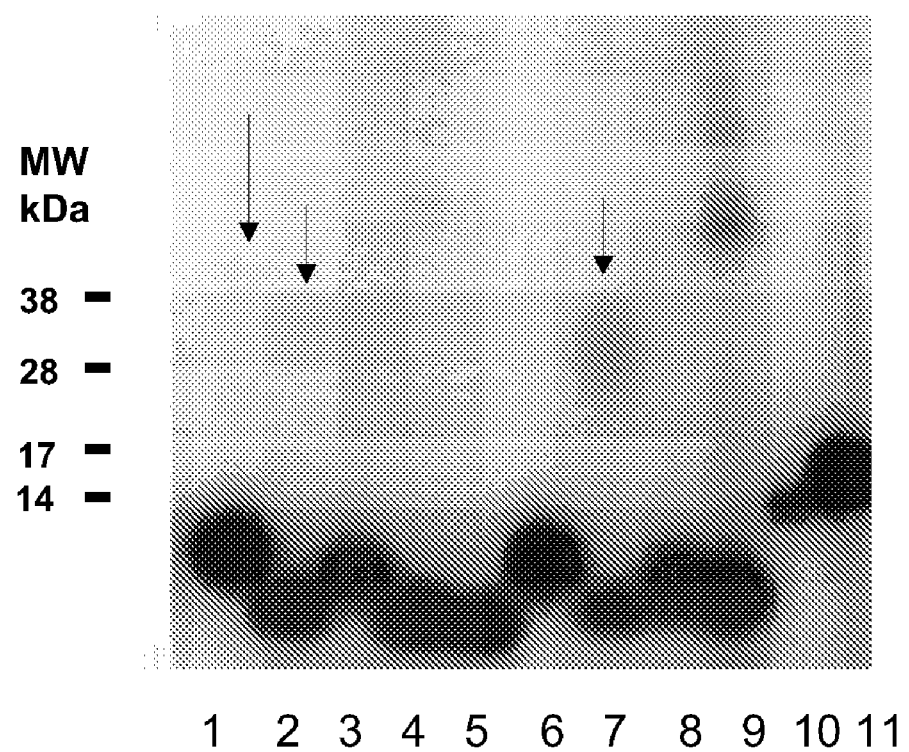
FIG. 7: Autoradiograph of the SDS-PAGE gel showing the complexes formed by crosslinking $^{125}$I-labeled chemokines with purified recombinant Evasin-3-6His. Lane 1, 40 ng viral CC-chemokine binding protein (p35) cross-linked to MCP-1 (positive control); Lanes 2-11, 10 ng Evasin-3-6His cross-linked to Gro-α/CXCL1 (Lane 2); eotaxin/CCL11 (Lane 3); RANTES/CCL5 (Lane 4); TARC/CCL17 (Lane 5); MCP-1/CCL2 (Lane 6); IL-8/CXCL8 (Lane 7); IP-10/CXCL10 (Lane 8); CTACK/CCL27 (Lane 9); IL-2 (Lane 10); IL-1α (Lane 11). The Evasin-3-6HIS complexes are indicated with arrows.

The selectivity was further tested using the purified recombinant Evasin-1 in a cross-linking assay using different $^{125}$I-CC-chemokines, CXC-chemokines and cytokines (FIG. 7.). As for the crosslinking described above, a band between 28-40 kDa (indicated with an arrow) corresponding to the complex is visible when $^{125}$I-CXCL8/IL-8 is added (FIG. 7 lane 7). A band with lower intensity (indicated with an arrow migrating) at the same size is also visible when cross-linked to $^{125}$I-CXCL1/Gro-alpha, indicating that recombinant Evasin-3 is also able to form a complex with this CXC-chemokine (FIG. 7 lane 2). In the case of the other $^{125}$I-proteins tested, no complex formation is visible on the gel. Again, vCC1 incubated with $^{125}$I-MCP-1 was used as positive control (FIG. 7 lane 1, indicated with an arrow).

Therefore, it can be concluded that Evasin-3 is a novel protein having CXC-chemokine binding properties, thereby inhibiting the action of chemokines.

Example 3

Purification and Validation of Evasin-3 Expressed in *Escherichia Coli*

Materials and Methods a. Subcloning of Evasin-3 cDNA into the Expression Vector pET30a.

The first stage of the cloning process involves a PCR reaction, which generates the ORF of Evasin-3 minus the signal peptide, and flanked at the 5' end by an initiating methionine and a NdeI restriction site, and flanked at the 3' end by two stop codons (TAA TAA) and the XhoI restriction site (FIG. 8). The PCR reaction (in a final volume of 50 µl) contains: 1 µl (100 ng) of plasmid pEXP-Lib-Evasin-3, 3.0 µl dNTPs (5 mM), 10 µl of 10×Pfx polymerase buffer, 1 µl MgSO$_4$ (50 mM), 1.5 µl each of gene specific primer (10 µM) (5'NdeI-eva3_ecoli SEQ ID NO:21; 3'XhoI-eva3_ecoli SEQ ID NO:22) (table IV), and 0.5 µl Platinum Pfx DNA polymerase (Invitrogen). The PCR reaction was performed using an initial denaturing step of 95° C. for 4 minutes, followed by 30 cycles of 95° C. for 30 s; 55° C. for 30 s and 68° C. for 1 min; and a holding cycle of 4° C. The resultant PCR product was visualized on 1.5% agarose gel in 1×TAE buffer (Invitrogen) and the band migrating at the predicted molecular mass (321 bp) was purified from the gel using the Wizard PCR Preps DNA Purification System (Promega), and eluted in 50 µl sterile water according to the manufacturer's instructions.

The second stage of the cloning process involves digestion of the modified PCR product using the restriction enzymes NdeI and XhoI followed by ligation into pET30a vector. Five µl of purified product from PCR were incubated with 1.0 µl NdeI (50,000 u/ml, BioLabs), 1 µl XhoI (50'000 u/ml, BioLabs), 6 µl of 100×NED2 buffer (BioLabs) and 0.6 µl of 100×BSA (BioLabs) in a final volume of 60 µl at 37° C. for 16 hours. The reaction mixture was visualized on 1.5% agarose gel run in 1×TAE buffer (Invitrogen) and the band migrating at the predicted molecular mass (320 bp) was purified from the gel using the Wizard PCR Preps DNA Purification System (Promega) and eluted in 50 µl sterile water according to the manufacturer's instructions. The purified insert was ligated into the vector pET30a which had been previously dephosphorylated and digested with NdeI and XhoI restriction enzymes as follows: 15 µl of purified product from digestion were incubated with 3 µl pET30a vector (150 ng), 1 µl T4 ligase (400,000 u/ml, BioLabs) and 2.2 µl T4 buffer 10× (BioLabs) in a final volume of 22 µl at room temperature for 4 hours.

An aliquot of this reaction (1 µl) was used to transform *E. coli* DH10B cells by electroporation as follows: a 25 µl aliquot of DH10B electrocompetent cells (Invitrogen) was thawed on ice and 1 µl of the BP reaction mix was added. The mixture was transferred to a chilled 0.1 cm electroporation cuvette and the cells electroporated using a BioRad Gene-Pulser™ according to the manufacturer's recommended protocol. SOC medium (0.5 ml), which had been pre-warmed to room temperature, was added immediately after electroporation. The mixture was transferred to a 15 ml snap-cap tube and incubated, with shaking (220 rpm) for 1 hour at 37° C. Aliquots of the transformation mixture (10 µl and 50 µl) were then plated on L-broth (LB) plates containing kanamycin (40 µl/ml) and incubated overnight at 37° C.

Plasmid mini-prep DNA was prepared from 5 ml cultures from 6 of the resultant colonies using a Qiaprep Turbo 9600 robotic system (Qiagen). Plasmid DNA (150-200 ng) was subjected to DNA sequencing with T7 (SEQ ID NO: 23) and pRSET-R (SEQ ID NO. 24) primers (table IV) using the BigDyeTerminator system (Applied Biosystems cat. no. 4336919) according to the manufacturer's instructions. Sequencing reactions were purified using Montage SEQ 96 cleanup plates (Millipore cat. no. LSKS09624) then analyzed on an Applied Biosystems 3700 sequencer.

Plasmid DNA (1 µl or 100 ng) from one of the clones, which contained the correct sequence (pET30a-Evasin-3) was then used to transform *E. coli* BL21D3 cells by heat-shock as follows: a 20 µl aliquot of BL21DE3 cells (Novagen) was thawed on ice into a 1.5 ml eppendorf tube, 1 µl of the plasmid was added and the mixture was incubated 5 min. on ice. The cells are then heat-shocked 30 sec in a 42° C. water bath, and put on ice for 2 min. After the addition of 80 µl of room temperature SOC medium, the cells were incubated at 37° C. for 1 hour with shaking and aliquots of the transformation mixture (20 µl and 80 µl) were then plated on L-broth (LB) plates containing kanamycin (40 µl/ml) and incubated overnight at 37° C. One kanamycin resistant colony was chosen for the expression of Evasin-3. Verification of the protein expression in the transformed *E. coli* strain was tested by inoculating a single kanamycin resistant colony in an ehrlenmeyer flask containing 50 ml Luria-Bertani (LB) broth, 40 µg/ml kanamycin. When the culture reached an O.D of 0.6 units, 0.5 mM IPTG (Isopropyl-β-D-thiogalactoside) was added and incubated for a further 3 h. The clone which gave the best expression level after IPTG induction was then used to generate a 100 ml culture which was then inoculated into a 5 L fermenter with medium at pH7 containing glycerol as the carbon source, ammonium sulphate as the nitrogen source, yeast extract, phosphate, salts, oligo-elements, antifoam and 40 µg/l kanamycin and fermented at 37° C. $CO_2$ was maintained at 30% with a constant air flow rate of 2.5 L/min and $O_2$ flow rate varying between 0-5 L min, and a stirring speed of 1000-1200 rpm. Protein expression was induced at an OD of 20-30 with 1 mM IPTG. The cells were harvested 3 h after induction at an OD of 30-40. The wet cell weight obtained was 200-300 g corresponding to a dry cell weight of 10-20 g/L.

b. Purification of Recombinant Evasin-3 Expressed in *E. coli*.

The *E. coli* cell pellet (250 g) was harvested 3 hours post induction with IPTG. from a 5 L fermentation The pellet was suspended in 1.25 L of cell breakage buffer (50 mM Tris-HCl pH 8.5 containing 2 mM $MgCl_2$, complete cocktail protease inhibitors EDTA-free (1 tablet/50 ml buffer, Roche) and 20 mg/l DNAse). Cells were broken by one passage through a French Press (Constant Cell Disruption System) at 1.7 kPa and the solution was centrifuged for 2 hours at 27,500×g (13,000 rpm).

The pH of the soluble cytosolic fraction was adjusted to pH 4.5 using acetic acid and centrifuged at 100,000×g (35,000 rpm) for 1 hour. After filtration through a 0.22 µm membrane filter, the protein in the supernatant was quantified using a colorimetric assay with Coomassie Plus Protein Assay Reagent (PIERCE) using albumin as a standard and a VERSAmax microplate reader (Molecular Devices) to obtain the OD at 780 nm. The supernatant was loaded at 3.5 ml/min at 4° C. onto a cation exchange column of Fractogel $SO_3^-$ (Amersham) previously equilibrated in 50 mM $CH_3COONa$ pH 4.5 using an Äkta purifier system (Amersham Biosciences). Non-specifically bound material was removed by washing the column at 5 ml/min with 5 column volumes (CVs) in 50 mM $CH_3COONa$ pH 4.5. Protein was eluted in 5 ml fractions using a linear gradient of 0-0.7 M NaCl in the same buffer with 17.5 column volumes (CVs).

The fractions containing Evasin-3 were pooled and concentrated 10-fold using centrifugal filter devices with a cut-off of 3.5 kDa (Amicon, Millipore). The concentrated pool was subjected to size exclusion chromatography as the second step of purification. 2 ml of the concentrated Evasin-3 solution was loaded onto an SX75 16/60 column (bed volume of 120 ml; Amersham Biosciences), previously equilibrated in PBS (Phosphate Buffered Saline). The protein was eluted in fractions of 2 ml at 2 ml/min. Evasin-3 containing fractions were pooled, aliquoted, and stored at −80° C.

d. SDS-PAGE and Crosslinking Analysis of Recombinant Evasin-3

The column eluates were diluted 1:1 with 2× sample buffer (Invitrogen) containing 100 mM DTT and boiled for 5 minutes. The samples and a molecular weight standard (Benchmark Protein Ladder; Invitrogen) were electrophoresed on a 10% Bis-Tris gel run in MES-buffer at 200 V for 35 min. The electrophoresed proteins were stained using Simply Blue SafeStain (Invitrogen) according to the manufacturer's instructions: the gel was rinsed three times with distilled water for 5 min, stained for 1 hour at room temperature and wash with water for 1 hour.

Results

The ORF encoding for Evasin-3 was subcloned into an expression vector allowing high level production in *Escherichia coli*.

Figure 9:
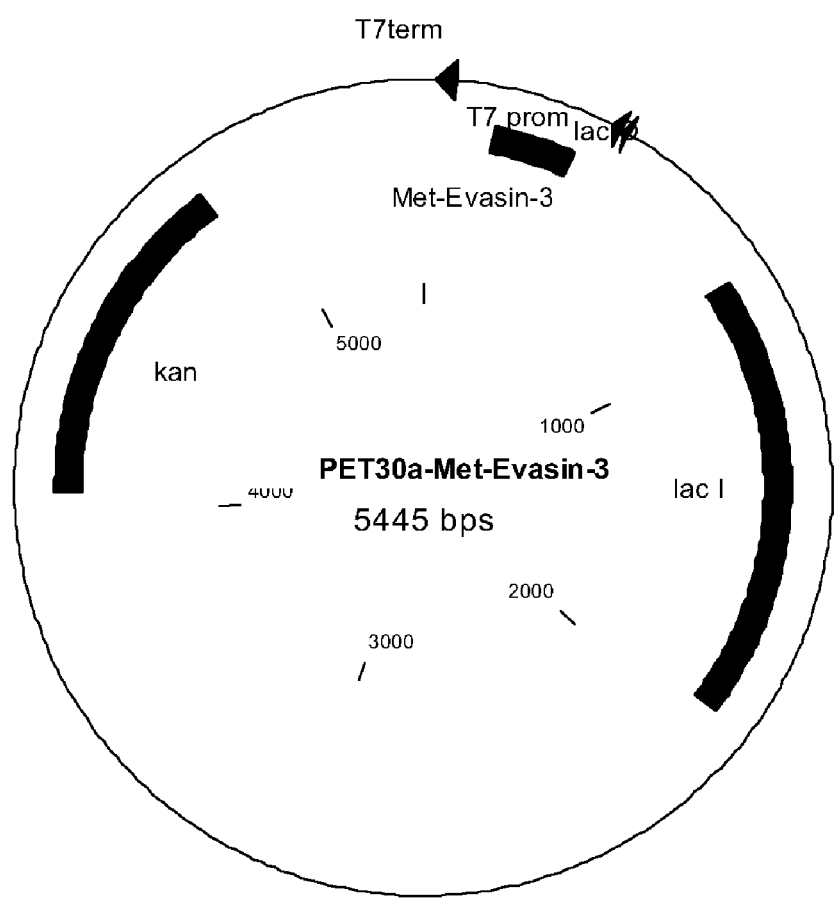
FIG. 9: Map of the pET30a-Evasin-3 vector used for expression in *Escherichia Coli*.

The plasmid containing the full length cDNA of Evasin-3 (pEXP-Lib_Evasin-3) was used as PCR template to generate an Evasin-3 ORF which consists of the mature protein coding sequence of Evasin-3 (after removal of the predicted signal peptide sequence) but which retains an initiating methionine at the N-terminal. The ORF for Met-Evasin-3 (SEQ ID NO: 25) encodes for a 67 amino acids sequence (SEQ ID NO: 26). The vector pET30a-Evasin-3 is given in FIG. 9.

Figure 10:
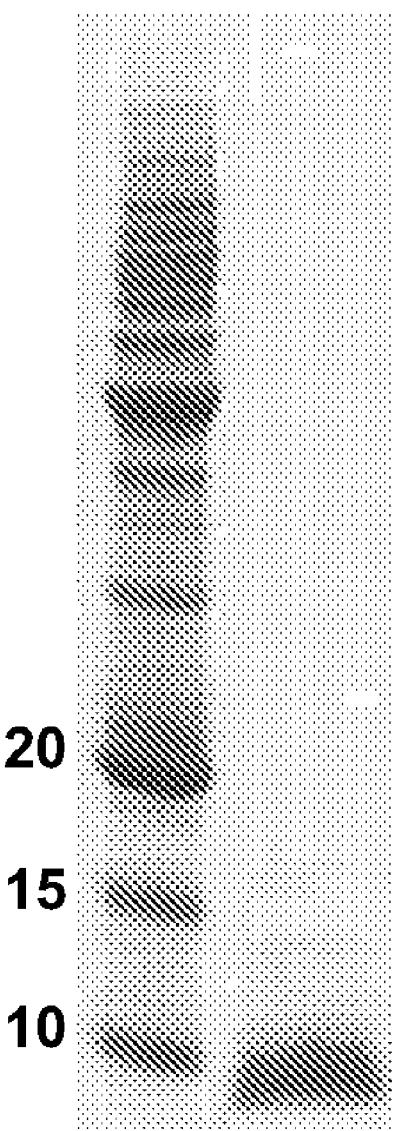
FIG. 10: SDS-PAGE gel stained with Coomassie blue showing Evasin-3 purified from *E. Coli*. The molecular weight standards are indicated on the left ($M_R$).

Recombinant Evasin-3 was purified from *E. coli*. The presence of recombinant Evasin-3 during the different purification steps was followed by SDS-PAGE using SimplyBlue SafeStain stained gels. Evasin-3 migrated with a molecular mass of 7 kDa as confirmed by Coomassie staining after SDS-PAGE (FIG. 10).

Figure 11:
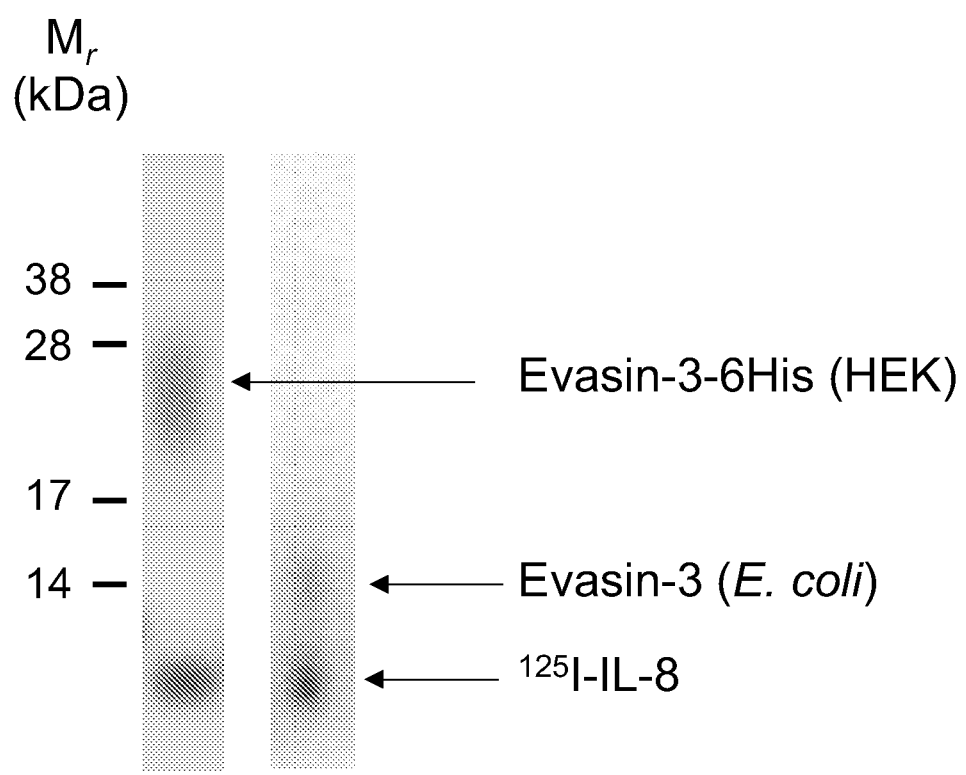
FIG. 11: Autoradiography of the SDS-PAGE gel showing the complexes formed by crosslinking $^{125}$I-labeled CXC-chemokine CXCL8/IL-8 with recombinant Evasin-3-6His expressed in HEK293 or Evasin-3 expressed in *E. Coli* The molecular weight standards (Kd) are indicated on the left (Mk). The complexes and the iodinated CXCL8/IL-8 are indicated with arrows.

On SDS-PAGE analysis, $^{125}$I-labeled CXC-chemokine CXCL8/IL-8 migrates as an 8 kDa band. When the cross-linking agent, BS3 is added, a portion of the radioactivity is detected in a protein complex migrating at 14 kDa, which is due to a complex formed between recombinant Evasin-3 and IL-8 (FIG. 11).

As recombinant proteins produced in *E. coli* are not generally glycosylated, it is likely that post translational glycosylation of Evasin-3 is not necessary for binding to IL-8.

Analysis of the recombinant protein by mass spectrometry by MALDI-TOF identified a mass of 7,131.42 Da, which corresponds to the predicted mass of the recombinant protein including the initiating methionine. The activity does not appear to be affected by the presence of the initiating methionine.

Example 4

Characterization of Recombinant Evasin-3-6His and Evasin-3 Inhibitory Activity on CXC-Chemokines Materials and Methods Receptor Binding Assay.

An equilibrium competition receptor binding assay was used to determine the inhibitory properties of Evasin-3 on the chemokine/chemokine receptor interaction. The binding experiments were performed using CHO cells (Chinese Hamster Ovary cells) which stably express the human IL-8 receptor CXCR1 (CHO/CXCR1). Cells were maintained in D-MEM F12 medium (Dulbecco's Modified Eagle Medium, Invitrogen catalogue no: 41965039) supplemented with 10% FCS (Fetal calf Serum; TerraCell, catalogue no: CS-C08-1000-A), 2 mM L-glutamine (Invitrogen catalogue no: 25030-024), 0.6 mg/ml Geneticin (invitrogen catalogue no: 11811-031), and 1% penicillin-streptomycin (Invitrogen catalogue no: 15140-148). Cells were harvested by centrifugation for 5 minutes at 230×g, and resuspended at a cell density of 4×10⁶ cells/ml in 50 mM Tris/HCl pH 7.5 buffer containing 1 mM $CaCl_2$, 5 mM $MgCl_2$ and 0.5% BSA. Recombinant Evasin-3-6His or Evasin-3, purified from HEK 293 or *E. Coli* cells respectively, was suspended at 0.01 mg/ml in the same medium and eleven serial, 4-fold dilutions were prepared in a MultiScreen HTS 96-well filtration system (Millipore). CHO/CXCR1 cells (1×10⁵ cells), 0.1 nM [$^{125}$I]-IL8 (Amersham catalogue no: IM249) and 25 µl of the serial dilutions of recombinant Evasin-3-6His or Evasin-3 were put in each well of the plate in a final volume of 100 µl to achieve a final concentration range of the recombinant protein from 350 µM to 0.08 µM. The mixture was then incubated 4 h at room temperature with shaking. Cells were then washed three times with 50 mM Tris/HCl pH 7.5 buffer containing 1 mM $CaCl_2$, 5 mM $MgCl_2$, 0.5% BSA and 2M NaCl. Scintillation fluid (50 μl) (PerkinElmer) was added to each well and radioactivity was measured using a β-scintillation counter (Wallac). See Results and FIG. 12.

b. CXC-Chemokine Induced Chemotaxis

Chemotaxis experiments were performed on neutrophils purified from human blood obtained from the University of Geneva Hospital. Human neutrophils naturally express CXCR1 and CXCR2. Human neutrophils were purified on the day of the experiment as follows: blood from a human buffy coat was diluted 2× with sterile PBS and 50 ml was placed in a conical polypropylene tube. Dextran 500 (Amersham Bioscience catalogue no:17-0320-02) was added to the blood (3 ml/20 ml of blood) and red blood cells were allowed to sediment for 1 h at room temperature. The supernatant was decanted into a fresh tube and centrifuged for 5 min at 230×g. The cell pellet was suspended in 10 ml of RPMI 1640 culture medium (Invitrogen, catalogue no: 31870-025) supplemented with 2% FCS. Ficoll-Plaque (10 ml) of was carefully layered onto the cell solution and centrifuged at 345×g at 4° C. for 30 min (without brake). The cell pellet was washed once with RPMI medium and any remaining red blood cells were destroyed by hypotonic shock by addition of 10 ml of 0.2% NaCl for 20 seconds. Isotonicity was quickly restored by adding 10 ml 1.6% NaCl solution. The suspension was centrifuged for 5 minutes at 230×g, the supernatant was carefully discarded and the cell pellet washed twice with medium. Purified neutrophils were suspended at a concentration of $2 \times 10^6$ cells/ml in chemotaxis medium (RPMI 1640 medium without phenol red indicator (Invitrogen catalogue no: 32404-014), supplemented with 2% FCS).

Evasin-3-6His was suspended at $1.25 \times 10^{-2}$ mg/ml in chemotaxis medium and eleven serial, 3-fold dilutions were prepared using the medium containing 1 nM CXCL8/IL-8 or CXCL1/Gro-alpha. Aliquots (32 μl) of the serially diluted chemokine solution or chemokine-Evasin-3-6His solution were added in triplicate to the lower compartments of a chemotaxis chamber and an 8-μm pore size filter unit (Neuroprobe ChemoTx System, catalogue no: 101-8) was carefully placed on top of the lower compartment. The neutrophil cell suspension (20 μl) was added to the top compartment of the chemotaxis chamber (filter unit) and the assembly was incubated for 2 hours at 37° C. in a humidified, 5% $CO_2$ incubator.

After 2 h, the lid of the chemotaxis chamber was then carefully removed and discarded. A 96-well funnel plate (Neuroprobe ChemoTx System catalogue No: FP1) was placed upside down on top of the lower compartment of the chemotaxis chamber. A black-matrix plate (Vitaris catalogue no: 3915) was then placed upside-down on top of the funnel plate and the chemotaxis chamber/funnel plate/black-matrix plate assembly was flipped over. The medium in the lower compartment of the chemotaxis chamber was then transferred into the black-matrix plate by centrifugation for 2 minutes at 700×g. The black-matrix plate containing the migrated cells was sealed and stored frozen for 2 hours at −80° C. The number of cells that had migrated into the lower compartment of the chemotaxis chamber was determined indirectly using the CyQUANT cell proliferation assay kit (Molecular Probes catalogue no: C7026) as follows: the black plate was thawed and cells were immediately and thoroughly resuspended in 200 μl of cell lysis buffer containing the dye provided in the kit, according to manufacturer's instructions. Fluorescence was measured in a Wallac Victor plate reader using 480 nm/520 nm excitation/emission wavelengths. See Results and FIG. 13.

c. Binding Analysis by Surface Plasmon Resonance (SPR).

Surface Plasmon Resonance (SPR) was used to directly measure the affinity and kinetics of CXC-chemokine binding by Evasin-3-6His or Evasin-3. Evasin-3-6His or Evasin-3 were suspended at 20 μg/ml in 10 mM sodium acetate buffer pH 4.5 or pH 4 (Biacore) respectively, and were directly immobilized on a CM4 chip (Biacore) by a standard amine coupling chemistry with the Biacore Amine coupling kit (Biacore), to reach a level of 200-300 response units (RU) using a Biacore3000 system. A blank cell was prepared as a control with the chemical coupling without any added protein. Experiments were performed at 25° C. and 30 μl/min using HBS-P running buffer (0.01 M HEPES pH7.4, 0.15 M NaCl and 0.005% surfactant P20) (Biacore). For all binding experiments, chemokines were suspended at 0.5 μg/ml in running buffer and filtered through a 0.22 μm filter. The injection time was 3 min followed by a dissociation time of 2.5 min after injection. The chip was regenerated using 50 mM Glycine buffer, pH 2 for 30 s. For each experiment, chemokines were injected in triplicate in random order. For the kinetic experiments, 6 dilutions of CXCL1/Gro-alpha, CXCL8/IL-8, murine CXCL1/KC and murine CXCL2/MIP-2 were prepared from 0.1 μg/ml to 6 ng/ml in running buffer, filtered through a 0.22 μm filter, and injected over the experimental and blank flow cells. The injection time was 3 min followed by a dissociation time of 15 min and the chip was regenerated using 50 mM Glycine pH 2 buffer for 30 s. Again, each chemokine dilution was injected in triplicate in a random order.

Figure 15:
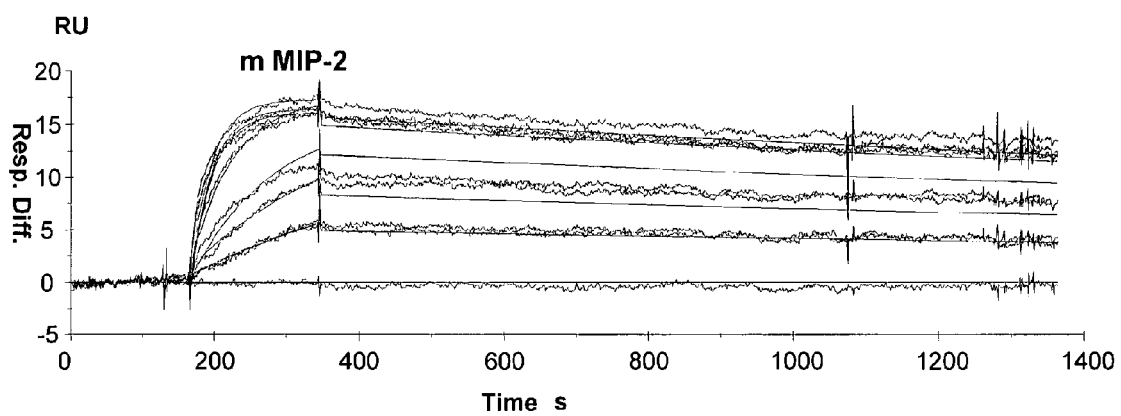
FIG. 15: SPR kinetic analysis of CXC-chemokines binding to Evasin-3-6His. A typical titration experiment is shown for the chemokines A) CXCL8/IL-8, B) Gro-alpha/CXCL1, C) murine CXCL1/KC and D) murine CXCL2/MIP-2. The experimental curves were globally fitted using a Langmuir fitting model to determine the kinetic parameters shown in Table 2.
Figure 16:
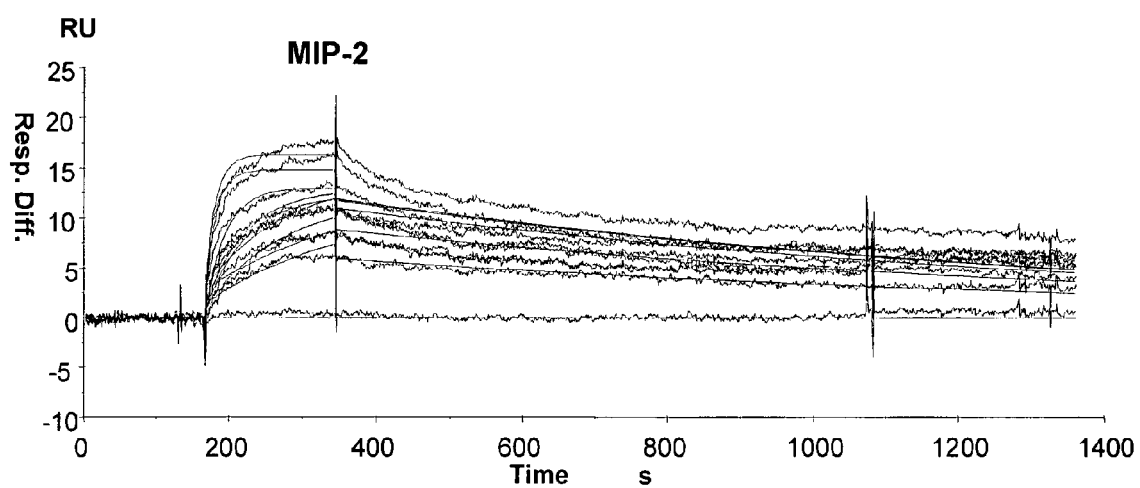
FIG. 16: SPR kinetic analysis of A) CXCL8/IL-8, B) Gro-alpha/CXCL1, C) murine CXCL1/KC and D) murine CXCL2/MIP-2 binding to Evasin-3. The experimental curves are globally fitted using a Langmuir fitting model to determine the kinetic parameters shown in Table 2.

For the analysis, the sensograms from the blank cell, in addition to the sensograms obtained with the running buffer alone were substracted from the binding to remove the system noise. For the kinetics, the association ($k_a$) and the dissociation ($k_d$) values were determined simultaneously by globally fitting sensograms for an entire range of chemokine concentrations according to the langmuir fitting model. The apparent equilibrium dissociation constants ($K_d$) were determined from the mean kinetics values with the equation: $K_d = k_d / k_a$. See Results and FIGS. 14, 15 and 16.

d Inhibition of Chemokine Mediated Neutrophil Recruitment In Vivo

Mice were given Evasin-3 at doses ranging from 0-01 to 100 μg/mouse or vehicle (saline) subcutaneuously (s.c.) 45 minutes prior to the administration of 30 ng KC (murine CXCL1) into the right knee joint of C57Bl6 mice. After 4 hours, mice were killed and the total number of infiltrating leukocytes (neutrophils comprise over 95% of these cells) counted on a Neubauer chamber. Differential counts were performed on stained cytospin slides. There were 3-4 animals in each experimental group. See Results and FIG. 17.

Results

The CXC-chemokine binding properties of Evasin-3-6His and Evasin-3 were studied in a receptor binding assay, a CXC-chemokine induced cell migration assay and by Surface Plasmon Resonance.

The receptor binding assay demonstrated that Evasin-3 expressed either in mammalian cells (HEK293 cells) as a 6His tagged protein or in a prokaryotic expression system (*E. coli*) was able to inhibit the binding of iodinated IL-8 to its receptor CXCR1, with $IC_{50}$ values of 1 and 20 nM respectively (FIG. 12).

Evasin-3 (Evasin-3-6His produced in HEK cells) was also able to inhibit IL-8 and Gro-alpha induced neutrophil chemotaxis with $IC_{50}$ values of 16 and 20 nM respectively (FIG. 13)

SPR analysis showed that Evasin-3 produced in mammalian cells or in *E. coli* is highly selective for the binding of CXCL8/IL-8, CXCL1/Gro-alpha, murine CXCL1/KC and murine CXCL2/MIP-2. Neither recombinant protein was able to bind to the other chemokines tested: CCL5/RANTES, CX3CL1/Fractalkine, CCL11/eotaxin. CCL3/MIP-1-alpha, CCL4/MIP-1-beta, CCL18/PARC, CCL2/MCP-1 and CXCL12/SDF-1-alpha (FIG. 14). The affinity ($K_d$) and kinetic parameters determined by SPR (FIGS. 15 and 16) for Evasin-3-6His and Evasin-3 is shown in Table V.

Figure 17:
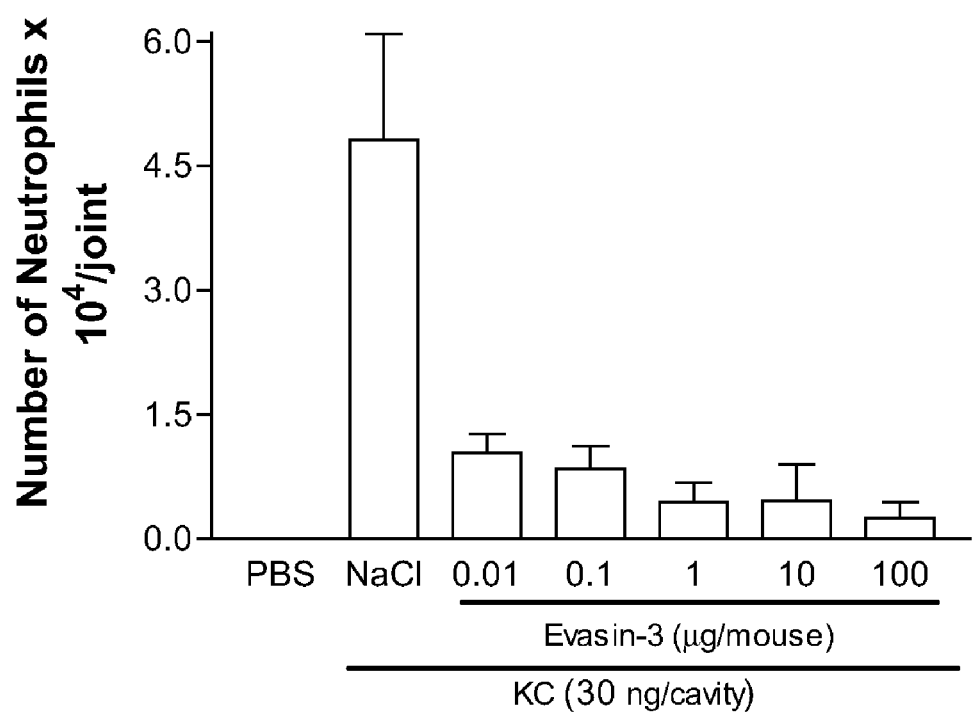
FIG. 17: Inhibition of neutrophil recruitment. Evasin-1 was administered into the knee joint of mice 45 minutes prior to the administration of KC

The inhibitory activity of Evasin-1 was further demonstrated by its ability to inhibit the recruitment of neutrophils induced by the administration of the murine neutrophil chemoattractant, KC, at doses ranging from 0.01-100 µg/mouse (FIG. 17).

It can therefore be concluded that Evasin-3 is a novel CXC-chemokine binding protein which could target neutrophil recruitment. This protein can be usefully applied in human medicine as an anti-inflammatory compound, as well as in problems of medical and veterinary indications related to the parasitic effects of ticks, including tick-borne infectious agents. Molecules based on the proteins of the invention and interfering with the function of such proteins, might disrupt the tick life-cycle, control ectoparasites and their pathogens, or reduce tick's ability to transmit disease-causing organisms.

TABLE I

| Amino Acid | Synonymous Group | More Preferred Synonymous Groups |
|---|---|---|
| Ser | Gly, Ala, Ser, Thr, Pro | Thr, Ser |
| Arg | Asn, Lys, Gln, Arg, His | Arg, Lys, His |
| Leu | Phe, Ile, Val, Leu, Met | Ile, Val, Leu, Met |
| Pro | Gly, Ala, Ser, Thr, Pro | Pro |
| Thr | Gly, Ala, Ser, Thr, Pro | Thr, Ser |
| Ala | Gly, Thr, Pro, Ala, Ser | Gly, Ala |
| Val | Met, Phe, Ile, Leu, Val | Met, Ile, Val, Leu |
| Gly | Ala, Thr, Pro, Ser, Gly | Gly, Ala |
| Ile | Phe, Ile, Val, Leu, Met | Ile, Val, Leu, Met |
| Phe | Trp, Phe, Tyr | Tyr, Phe |
| Tyr | Trp, Phe, Tyr | Phe, Tyr |
| Cys | Ser, Thr, Cys | Cys |
| His | Asn, Lys, Gln, Arg, His | Arg, Lys, His |
| Gln | Glu, Asn, Asp, Gln | Asn, Gln |
| Asn | Glu, Asn, Asp, Gln | Asn, Gln |
| Lys | Asn, Lys, Gln, Arg, His | Arg, Lys, His |
| Asp | Glu, Asn, Asp, Gln | Asp, Glu |
| Glu | Glu, Asn, Asp, Gln | Asp, Glu |
| Met | Phe, Ile, Val, Leu, Met | Ile, Val, Leu, Met |
| Trp | Trp, Phe, Tyr | Trp |

TABLE II

| Amino Acid | Synonymous Group |
|---|---|
| Ser | D-Ser, Thr, D-Thr, allo-Thr, Met, D-Met, Met(O), D-Met(O), L-Cys, D-Cys |
| Arg | D-Arg, Lys, D-Lys, homo-Arg, D-homo-Arg, Met, Ile, D-.Met, D-Ile, Orn, D-Orn |
| Leu | D-Leu, Val, D-Val, AdaA, AdaG, Leu, D-Leu, Met, D-Met |
| Pro | D-Pro, L-I-thioazolidine-4-carboxylic acid, D-or L-1-oxazolidine-4-carboxylic acid |
| Thr | D-Thr, Ser, D-Ser, allo-Thr, Met, D-Met, Met(O), D-Met(O), Val, D-Val |
| Ala | D-Ala, Gly, Aib, B-Ala, Acp, L-Cys, D-Cys |
| Val | D-Val, Leu, D-Leu, Ile, D-Ile, Met, D-Met, AdaA, AdaG |
| Gly | Ala, D-Ala, Pro, D-Pro, Aib, .beta.-Ala, Acp |
| Ile | D-Ile, Val, D-Val, AdaA, AdaG, Leu, D-Leu, Met, D-Met |
| Phe | D-Phe, Tyr, D-Thr, L-Dopa, His, D-His, Trp, D-Trp, Trans-3,4, or 5-phenylproline, AdaA, AdaG, cis-3,4, or 5-phenylproline, Bpa, D-Bpa |
| Tyr | D-Tyr, Phe, D-Phe, L-Dopa, His, D-His |
| Cys | D-Cys, S--Me--Cys, Met, D-Met, Thr, D-Thr |
| Gln | D-Gln, Asn, D-Asn, Glu, D-Glu, Asp, D-Asp |
| Asn | D-Asn, Asp, D-Asp, Glu, D-Glu, Gln, D-Gln |
| Lys | D-Lys, Arg, D-Arg, homo-Arg, D-homo-Arg, Met, D-Met, Ile, D-Ile, Orn, D-Orn |
| Asp | D-Asp, D-Asn, Asn, Glu, D-Glu, Gln, D-Gln |
| Glu | D-Glu, D-Asp, Asp, Asn, D-Asn, Gln, D-Gln |
| Met | D-Met, S--Me--Cys, Ile, D-Ile, Leu, D-Leu, Val, D-Val |

TABLE III

| Primer | Sequence (5'-3') |
|---|---|
| Evasin3 PCR1F | GCAGGCTTC<u>GCCACC</u>ATGGTGTCGATGAAGACAAC (SEQ ID NO: 7) |
| Evasin3 PCR1R | *TGATGGTGATGGT*GACGCCTTACAACTGGTGGTTC (SEQ ID NO: 8) |
| Evasin3 PCR2F | GGGGACAAGTTTGTACAAAAAAGCAGGCTTC<u>GCCAC</u> (SEQ ID NO: 9) |
| Evasin3 PCR2R | GGGGACCACTTTGTACAAGAAAGCTGGGTTCA*ATGGTGA TGGTGATGGTGA* (SEQ ID NO: 10) |
| pEAK12F | GCCAGCTTGGCACTTGATGT (SEQ ID NO: 11) |
| pEAK12R | GATGGAGGTGGACGTGTCAG (SEQ ID NO: 12) |
| pDEST8F | TCTTCTACGGCAAGGTGCTG (SEQ ID NO: 13) |
| pDEST8R | AAGCAAGTAAAACCTCTACA (SEQ ID NO: 14) |
| Evasin3-6HisF | ACCAGTTGTAAGGCGT*CACCATCACCATCACCAT*TAAGGAGATGACCTAC (SEQ ID NO: 19) |
| Evasin3-6HisR | TAGGTCATCTCCTTA*ATGGTGATGGTGATGGTGAC*GCCTTACAACTGGTG (SEQ ID NO:20 |
| T7F | TAATACGACTCACTATAGGG (SEQ ID NO: 23 |

<u>Underlined</u> sequence = Kozak sequence
Bold = Start codon/Stop codon
*Italic* sequence = His tag

TABLE IV

| Primer | Sequence (5'-3') |
|---|---|
| 5'NdeI-eva3_ecoli | GGAATTCCATATGCTTGTTTCAACTATTG (SEQ ID NO: 21) |
| 3'XhoI-eva3_ecoli | CGCTCGAG*TTATTA*ACGCCTTACAACTGGTGGTTC (SEQ ID NO: 22) |

TABLE IV-continued

| Primer | Sequence (5'-3') |
|---|---|
| T7 | TAATACGACTCACTATAGGG (SEQ ID NO: 23) |
| PRSET-R | TGGCAGCAGCCAACTCAGCTT (SEQ ID NO: 24) |

Bold = Start codon
*Italic* = Stop codon

TABLE V

| | Evasin-3-6His | | | Evasin-3 | | |
|---|---|---|---|---|---|---|
| | a (1/Ms) | d (1/s) | d (nM) | a (1/Ms) | d (1/s) | d (nM) |
| CXCL8/IL-8 | $8.26 \times 10^5$ | $1.78 \times 10^{-4}$ | 0.22 | $6.03 \times 10^5$ | $3.20 \times 10^{-4}$ | 0.53 |
| CXCL1/Gro-murine | $2.60 \times 10^6$ | $1.17 \times 10^{-3}$ | 0.45 | $2.23 \times 10^6$ | $2.69 \times 10^{-3}$ | 1.21 |
| CXCL1/KC | $2.25 \times 10^5$ | $1.2 \times 10^{-3}$ | 5.34 | $5.14 \times 10^5$ | $2.35 \times 10^{-3}$ | 4.56 |
| Murine CXCL2/MIP-2 | $1.43 \times 10^6$ | $2.55 \times 10^{-4}$ | 0.18 | $1.05 \times 10^6$ | $8.78 \times 10^{-4}$ | 0.84 |

REFERENCES

Alarcon-Chaidez F J et al., Parasite Immunol, 25: 69-77, 2003.
Aljamali M N et al., Insect Mol Biol, 12: 299-305, 2003.
Baggiolini M et al., Annu Rev Immunol, 15: 675-705, 1997.
Baggiolini M, J Intern Med, 250: 91-104, 2001.
Beck C G et al., J Biol Chem, 276: 43270-43276, 2001.
Ben-Bassat A, Bioprocess Technol., 12:147-159, 1991
Brown A et al., J Pept Sci, 2:40-46, 1996.
Burns J M et al., J Biol. Chem., 277:2785-2789, 2002.
Bursill C A et al., Circulation, 110: 2460-2466, 2004.
Chuang V T et al., Pharm Res., 19: 569-577, 2002.
Clackson et al., Nature, 352:624-628, 1991.
Cleland J L et al., Curr Opin Biotechnol, 12: 212-9, 2001.
Coleman R et al., Drug Discov Today, 6: 1116-1126, 2001.
Dougherty D A, Curr Opin Chem Biol, 4: 645-52, 2000.
Ferreira B R and Silva J S, Vet Immunol Immunopathol, 64: 279-293, 1998.
Gendel S M, Ann NY Acad SCI, 964: 87-98, 2002.
Gillespie R D et al., J Immunol, 166: 4319-4326, 2001.
Golebiowski A et al., Curr Opin Drug Discov Devel, 4: 428-34, 2001.
Goding, Monoclonal Antibodies: Principles and Practice, Academic Press, (1986) pp. 59-103
Graslund T et al., Protein Expr Purif., 9: 125-132, 1997.
Greenwald R B et al., Adv Drug Deliv Rev, 55: 217-250, 2003.
Hajnicka, V., et al., Parasitology 130:333-342, 2005.
Harris J M and Chess R B, Nat Rev Drug Discov, 2: 214-221, 2003.
Hill C A and Gutierrez J A, Med Vet Entomol, 17: 224-227, 2003.
Holt L J et al., Trends Biotechnol, 21:484-490, 2003.
Hoogenboom and Winter, J. Mol. Biol, 227:381, 1991.
Hruby V J and Balse P M, Curr Med Chem, 7: 945-970, 2000.
Jones et al., Nature, 321:522-525, 1986.
Kipriyanov S M and Le Gall F, Mol Biotechnol, 26:39-60, 2004.
Kohler et al, Nature 256: 495, 1975
Jensen K K et al., J Virol, 77: 624-630, 2003.
Li A, Drug Discov Today, 6: 357-366, 2001.
Luo B and Prestwich G D, Exp Opin Ther Patents, 11: 1395-1410, 2001.
Madden R D et al., Exp Appl Acarol, 32: 77-87, 2004.
Marks et al., J. Mol. Biol., 222:581-597, 1991.
Marshall S A et al., Drug Disc Today, 8: 212-221, 2003.
Mulenga A et al., Microbes Infect, 2: 1353-1361, 2000.
Murphy L R et al., Protein Eng, 13:149-152, 2000.
Murrell A et al., Mol Phylogenet Evol, 21: 244-258, 2001.
Nilsson J et al., Protein Expr Purif, 11: 1-16, 1997.
Pearson W R, Methods Mol. Biol., 132:185-219, 2000.
Pillai O and Panchagnula R, Cur Opin Chem Biol, 5: 447-451, 2001.
Presta L, Curr Opin Struct Biol, 13: 519-525, 2003.
Pyo R et al., Am J Pathol, 164: 2289-2297, 2004.
Rapoport T A et al., Annu Rev Biochem., 65:271-303, 1996.
Rogov S I and Nekrasov A N, Protein Eng, 14: 459-463, 2001.
Scatchard G., Ann NY Acad. Sci. 51: 660-672, 1949
Schellekens H, Nat Rev Drug Disc, 1: 457-462, 2002.
Seet B T et al., Proc Natl Acad Sci USA, 98: 9008-9013, 2001.
Ullmann A J et al., Exp Appl Acarol, 28: 107-126, 2002.
Vaitukaitis et al. J Clin Endocrinol Metab. 33, p. 988, 1971
Valenzuela J G, Am J Trop Med Hyg, 66: 223-224, 2002.
Vasserot A P et al., Drug Disc Today, 8: 118-126, 2003.
Van Valkenburgh H A and Kahn R A, Methods Enzymol., 344:186-193, 2002.
Villain M et al., Chem Biol, 8: 673-679, 2001.
Wang H et al., Exp Appl Acarol 1999, 23: 969-975, 1999.
Ward et al., Nature 341:544, 1989
Webb L M et al., FASEB J, 18: 571-573, 2004.

The invention claimed is:

1. An isolated polypeptide comprising:
   a) SEQ ID NO: 5 (Evasin-3);
   b) SEQ ID NO: 6 (mature Evasin-3);
   c) SEQ ID NO: 17 (Evasin-3-HIS);
   d) SEQ ID NO: 18 (mature Evasin-3-HIS);
   e) SEQ ID NO: 26 (Met-Evasin-3); or
   f) SEQ ID NO: 5 in which a cysteine residue in the position corresponding to residues 48, 52, 59, 63, 65 or 76 or the asparagine at position 51 or 82 has been substituted.

2. The isolated polypeptide according to claim 1, wherein said polypeptide comprises SEQ ID NO: 5 (Evasin-3).

3. The isolated polypeptide according to claim 1, wherein said polypeptide comprises SEQ ID NO: 6 (mature Evasin-3).

4. The isolated polvpeptide according to claim 1, wherein said polypeptide comprises SEQ ID NO: 17 (Evasin-3-HIS).

5. The isolated polypeptide according to claim 1, wherein said polypeptide comprises SEQ ID NO: 18 (mature Evasin-3-HIS).

6. The isolated polypeptide according to claim 1, wherein said polypeptide comprises SEQ ID NO: 26 (Met-Evasin-3).

7. The isolated polypeptide according to claim 1, wherein said polypeptide comprises SEQ ID NO: 5 (Evasin-3) and in which a cysteine residue in the position corresponding to residues 48, 52, 59, 63, 65 or 76 or the asparagine at position 51 or 82 has been substituted.

8. The isolated polypeptide according to claim 1 wherein said polypeptide further comprises one or more amino acid sequences chosen from the following: an extracellular domain of a membrane-bound protein, an immunoglobulin constant region, a multimerization domain, a heterodimeric protein hormone, a signal peptide, an export signal or a tag sequence operably linked to said polypeptide.

9. A composition comprising a pharmaceutically acceptable carrier and a polypeptide comprising;
   a) SEQ ID NO: 5 (Evasin-3);
   b) SEQ ID NO:6 (mature Evasin -3);
   c) SEQ ID NO: 17 (Evasin-3-HIS);
   d) SEQ ID NO: 18 (mature Evasin-3-HIS);
   e) SEQ ID NO: 26 (Met-Evasin-3); or
   f) SEQ ID NO: 5 in which a cysteine residue in the position corresponding to residues 48, 52, 59, 63, 65 or 76 or the asparagine at position 51 or 82 has been substituted.

10. The composition according to claim 9, wherein said polypeptide comprises SEQ ID NO: 5 (Evasin-3).

11. The composition according to claim 9, wherein said polypeptide comprises SEQ ID NO: 6 (mature Evasin-3).

12. The composition according to claim 9, wherein said polypeptide comprises SEQ ID NO: 17 (Evasin-3-HIS)

13. The composition according to claim 9, wherein said polypeptide comprises SEQ ID NO): 18 (mature Evasin-3-HIS).

14. The composition according to claim 9, wherein said polypeptide comprises SEQ ID NO: 26 (Met-Evasin-3).

15. The composition according to claim 9, wherein said polypeptide comprises SEQ ID NO: 5 (Evasin-3) and in which a evsteine residue in the position corresponding to residues 48, 52, 59, 63, 65 or 76 or the asparagine at position 51 or 82 has been substituted.

16. The composition according to claim 9, wherein said polypeptide further comprises one or more amino acid sequences chosen from the following: an extracellular domain of a membrane-bound protein, an immunoglobulin constant region, a multimerization domain, a heterodimeric protein hormone, a signal peptide, an export signal or a tag sequence operably linked to said polypeptide.

17. An isolated nucleic acid encoding a polypeptide comprising:
   a) SEQ ID NO:5 (Evasin-31);
   b) SEQ ID NO:6 (mature Evasin-3);
   c) SEQ ID NO: 17 (Evasin-3-HIS);
   d) SEQ ID NO: 18 (mature Evasin-3HIS);
   e) SEQ ID NO: 26 (Met-Evasin-3); or
   f) SEQ ID NO: 5 in which a cysteine residue in the position corresponding to residues 48, 52, 59, 63, 65 or 76 or the asparagine at position 51 or 82 has been substituted.

18. An isolated cloning or expression vector comprising a nuclcic acid encoding a polypeptide comprising; a) SEQ ID NO: 5 (Evasin-3); b) SEQ ID NO: 6 (mature Evasin-3); c) SEQ ID NO: 17 (Evasin-3-HIS); d) SEQ ID NO: 18 (mature Evasin-3-HIS); e) SEQ ID NO: 26 (Met-Evasin-3); or f) SEQ ID NO: 5 in which a cysteine residue in the position corresponding to residues 48, 52, 59, 63, 65 or 76 or the asparagine at position 51 or 82 has been substituted.

19. An isolated host cell comprising an expression vector comprising a nucleic acid encoding a polypeptide comprising: a) SEQ ID NO: 5 (Evasin-3); b) SEQ ID NO: 6 (mature Evasin-3); c) SEQ ID NO: 17 (Evasin-3-HIS); d) SEQ ID NO: 18 (mature Evasin-3-HIS); e) SEQ ID NO: 26 (Met-Evasin-3); or f) SEQ ID NO: 5 in which a cysteine residue in the position corresponding to residues 48, 52, 59, 63, 65 or 76 or the asparagine at position 51 or 82 has been substituted.

20. A method for producing a polypeptide comprising culturing a host cell under conditions allowing or promoting expression of said polypeptide, wherein said host cell comprising an expression vector comprising: a nucleic acid encoding a polypeptide comprising: a) SEQ ID NO: 5 (Evasin-3); b) SEQ ID NO: 6 (mature Evasin-3); c) SEQ ID NO: 17 (Evasin-3-HIS); d) SEQ ID NO: 18 (mature Evasin-3-HIS); e) SEQ ID NO: 26 (Met-Evasin-3); or f) SEQ ID NO:5 in which a cysteine residue in the position corresponding to residues 48, 52, 59, 63, 65 or 76 or the asparagine at position 51 or 82 has been substituted.

21. The method according to claim 20, further comprising purifying the polypeptide.

22. The method according to claim 21, further comprising formulating the polypeptide with a pharmaceutically acceptable carrier.

23. A method for immunizing an animal against a blood-feeding ectoparasite comprising administering to said animal a polypeptide comprising: comprising a nucleic acid encoding a polypeptide comprising: a) SEQ ID NO: 5 (Evasin-3); b) SEQ ID NO: 6 (mature Evasin-3) c) SEQ ID NO: 17 (Evasin-3-HIS); d) SEQ ID NO: 18 (mature Evasin-3-HIS); e) SEQ ID NO: 26 (Met-Evasin-3); or f) SEQ ID NO: 5 in which a cysteine residue in the position corresponding to residues 48, 52, 59, 63, 65 or 76 or the asparagine at position 51 or 82 has been substituted.

* * * * *

UNITED STATES PATENT AND TRADEMARK OFFICE
CERTIFICATE OF CORRECTION

PATENT NO. : 7,670,802 B2
APPLICATION NO. : 12/067221
DATED : March 2, 2010
INVENTOR(S) : Amanda Proudfoot et al.

It is certified that error appears in the above-identified patent and that said Letters Patent is hereby corrected as shown below:

Column 9,
Line 33, "the formation or dimers" should read --the formation of dimers--.

Column 13,
Line 7, "initiatingMethionine" should read --initiating Methionine--.

Column 25,
Line 60, "b. Construction" should read --a. Construction--.

Column 26,
Line 28, "c. Library" should read --b. Library--.

Column 27,
Line 38, "Evasin 3" should read --Evasin-3--.

Column 28,
Lines 29-30, "vector (0.1 µl/µl)" should read --vector (0.1 µg/µl)--.
Line 46, "(40 µl/ml)" should read --(40 µg/ml)--.

Column 29,
Line 29, "of 1 µl/µl" should read --of 1 µg/µl--.

Column 30,
Line 18, "1 µl/µl" should read --1 µg/µl--.

Column 34,
Line 9, "XhoI (50'000" should read --XhoI (50,000--.
Lines 37-38, "(40 µl/ml)" should read --(40 µg/ml)--.
Line 60, "(40 µl/ml)" should read --(40 µg/ml)--.

Signed and Sealed this

Eighth Day of June, 2010

David J. Kappos
*Director of the United States Patent and Trademark Office*

Column 35,
Line 62, "and wash with" should read --and washed with--.

Column 36,
Line 64, "0.08 μM" should read --0.08 pM--.

Column 37,
Line 19, "(10 ml) of was carefully" should read --(10 ml) was carefully--.

Column 38,
Line 40, "d Inhibition of" should read --d. Inhibition of--.

Column 55,
Line 62, "comprising;" should read --comprising:--.

Column 56,
Line 44, "which a evsteine" should read --which a cysteine--.
Line 56, "a) SEQ ID NO:5 (Evasin-31);" should read --a) SEQ ID NO:5 (Evasin-3);--.
Line 65, "nuclcic acid" should read --nucleic acid--.
Line 65, "comprising;" should read --comprising:--.

Column 58,
Lines 11-12, "comprising: comprising a nucleic acid encoding a polypeptide comprising: a)" should read
--comprising: a)--.

SEQUENCE LISTING

<160> NUMBER OF SEQ ID NOS: 28

<210> SEQ ID NO 1

<211> LENGTH: 247
<212> TYPE: PRT
<213> ORGANISM: Ectromelia virus

<400> SEQUENCE: 1

Met Lys Gln Tyr Ile Val Leu Ala Cys Ile Cys Leu Ala Ala Ala
1               5                   10                  15

Ile Pro Thr Ser Leu Gln Gln Ser Phe Ala Ser Ser Cys Thr Glu Glu
            20                  25                  30

Glu Asn Asn His His Met Gly Ile Asp Val Ile Ile Lys Val Thr Lys
            35                  40                  45

Gln Asp Gln Thr Pro Thr Asn Asp Lys Ile Cys Gln Ser Val Thr Glu
    50                  55                  60

Val Thr Glu Ser Glu Asp Asp Gly Val Ser Glu Val Val Lys Gly
65                  70                  75                  80

Asp Pro Thr Thr Tyr Tyr Thr Val Val Gly Gly Gly Leu Arg Met Asn
                85                  90                  95

Phe Gly Phe Thr Lys Cys Pro Gln Ile Lys Ser Ile Ser Glu Ser Ala
            100                 105                 110

Asp Gly Asn Thr Val Asn Ala Arg Leu Ser Ser Val Ser Pro Met Tyr
            115                 120                 125

Gly Ile Glu Ser Pro Ala Ile Thr His Glu Glu Ala Leu Ala Met Ile
    130                 135                 140

Asn Asp Cys Ala Val Ser Ile Asn Ile Lys Cys Ser Glu Glu Glu Lys
145                 150                 155                 160

Asp Ser Asn Ile Lys Thr His Pro Val Leu Gly Ser Asn Ile Ser His
                165                 170                 175

Lys Lys Val Arg Tyr Glu Asp Ile Ile Gly Ser Thr Ile Val Asp Ile
            180                 185                 190

Lys Cys Val Lys Asp Leu Glu Phe Ser Val Arg Ile Gly Asp Met Cys
            195                 200                 205

Lys Glu Ala Ser Glu Leu Glu Val Lys Asp Gly Phe Lys Tyr Ile Asp
    210                 215                 220

Gly Ser Val Ser Glu Gly Ala Thr Asp Asp Thr Ser Leu Ile Asp Ser
225                 230                 235                 240

Thr Lys Leu Lys Ala Cys Val
            245

<210> SEQ ID NO 2
<211> LENGTH: 744
<212> TYPE: DNA
<213> ORGANISM: Ectromelia virus

<400> SEQUENCE: 2
atgaaacaat atatcgtcct ggcatgcata tgcctggcgg cagctgctat ccctaccagt      60
cttcagcaat cattcgcatc ctcgtgtacg gaagaagaaa acaaccatca tatgggaatc     120
gatgttatta tcaaagtcac caagcaagac caaacaccga ctaatgataa gatttgtcaa     180
tcagtaaccg aagttacaga gtctgaagac gatggggtat ccgaagaagt cgtaaaagga     240
gatcccacca cttattacac tgtcgtcggt ggaggtctga atgaacttt ggattcacc      300 aaatgtcctc agattaaatc catctcagaa tccgctgatg aaacacagt gaatgctcgg      360 ttgtctagcg tctctccaat gtacggcatt gaatctccag ccatcactca tgaagaagct     420
cttgctatga tcaacgactg tgcggtgtct atcaatatca aatgtagtga agaagagaaa     480
gacagcaaca tcaagaccca tccagtactc gggtctaaca tctctcataa gaaagtgagg     540

```
tacgaagata tcatcggttc aacgatcgtc gatataaaat gtgtcaagga tctagagttt    600
agcgttcgta tcggagacat gtgcaaggaa gcatctgaac ttgaagtcaa ggatggattc    660
aagtatatcg acggatcggt atctgaaggt gcaaccgatg atacttcact catcgattca    720
acaaaactca aagcgtgtgt ctga                                           744
```

<210> SEQ ID NO 3
<211> LENGTH: 491
<212> TYPE: DNA
<213> ORGANISM: Rhipicephalus sanguineus
<220> FEATURE:
<221> NAME/KEY: misc_feature
<222> LOCATION: (468)..(468)
<223> OTHER INFORMATION: n is a, c, g, or t

<400> SEQUENCE: 3

```
cggccggggg agcaaacatc gcagttgctg aacggttgcg ctcgtcttat aagcaggagt     60
aataccggtg atcagagggc gtataacggt aaggaaggta gtgagcttat tcctttgtac    120
gagacattgt gcatcgcagg tatggtgtcg atgaagacaa cgcatcatgt cctatttctg    180
ctagttgctt tggaatcaat gcgaccctac acgactgctc ttgtttcaac tattgagtca    240
agaacgagtg gagatggcgc agataacttt gatgtagtat cttgtaataa gaattgcact    300
tcaggtcaaa acgaatgccc tgaaggctgt ttttgcggct gttgggccag aacaaaaaa     360 ggtcattgct acaaaattat agggaacctt tctggagaac caccagttgt aaggcgttaa    420
ggagatgacc tacagctcag atgaataata aaaaaatta agactaanaa aaaaaaaaa     480 aaaaaaaaaa a                                                         491
```

<210> SEQ ID NO 4
<211> LENGTH: 279
<212> TYPE: DNA
<213> ORGANISM: Rhipicephalus sanguineus

<400> SEQUENCE: 4

```
atggtgtcga tgaagacaac gcatcatgtc ctatttctgc tagttgcttt ggaatcaatg     60
cgaccctaca cgactgctct tgtttcaact attgagtcaa gaacgagtgg agatggcgca    120
gataactttg atgtagtatc ttgtaataag aattgcactt caggtcaaaa cgaatgccct    180
gaaggctgtt tttgcggctt gttgggccag aacaaaaaag gtcattgcta caaaattata    240
gggaaccttt ctggagaacc accagttgta aggcgttaa                           279
```

<210> SEQ ID NO 5
<211> LENGTH: 92
<212> TYPE: PRT
<213> ORGANISM: Rhipicephalus sanguineus

<400> SEQUENCE: 5

```
Met Val Ser Met Lys Thr Thr His His Val Leu Phe Leu Leu Val Ala
1               5                   10                  15

Leu Glu Ser Met Arg Pro Tyr Thr Thr Ala Leu Val Ser Thr Ile Glu
            20                  25                  30

Ser Arg Thr Ser Gly Asp Gly Ala Asp Asn Phe Asp Val Val Ser Cys
        35                  40                  45

Asn Lys Asn Cys Thr Ser Gly Gln Asn Glu Cys Pro Glu Gly Cys Phe
    50                  55                  60

Cys Gly Leu Leu Gly Gln Asn Lys Lys Gly His Cys Tyr Lys Ile Ile
65                  70                  75                  80
```

Gly Asn Leu Ser Gly Glu Pro Pro Val Val Arg Arg
            85                  90

<210> SEQ ID NO 6
<211> LENGTH: 66
<212> TYPE: PRT
<213> ORGANISM: Rhipicephalus sanguineus

<400> SEQUENCE: 6

Leu Val Ser Thr Ile Glu Ser Arg Thr Ser Gly Asp Gly Ala Asp Asn
1               5                   10                  15

Phe Asp Val Val Ser Cys Asn Lys Asn Cys Thr Ser Gly Gln Asn Glu
            20                  25                  30

Cys Pro Glu Gly Cys Phe Cys Gly Leu Leu Gly Gln Asn Lys Lys Gly
        35                  40                  45

His Cys Tyr Lys Ile Ile Gly Asn Leu Ser Gly Glu Pro Pro Val Val
    50                  55                  60

Arg Arg
65

<210> SEQ ID NO 7
<211> LENGTH: 35
<212> TYPE: DNA
<213> ORGANISM: Artificial Sequence
<220> FEATURE:
<223> OTHER INFORMATION: Primer evasin3 PCR1F

<400> SEQUENCE: 7
gcaggcttcg ccaccatggt gtcgatgaag acaac                          35

<210> SEQ ID NO 8
<211> LENGTH: 35
<212> TYPE: DNA
<213> ORGANISM: Artificial Sequence
<220> FEATURE:
<223> OTHER INFORMATION: Primer evasin3 PCR1R

<400> SEQUENCE: 8
tgatggtgat ggtgacgcct tacaactggt ggttc                          35

<210> SEQ ID NO 9
<211> LENGTH: 36
<212> TYPE: DNA
<213> ORGANISM: Artificial Sequence
<220> FEATURE:
<223> OTHER INFORMATION: Primer evasin3 PCR2F

<400> SEQUENCE: 9
ggggacaagt ttgtacaaaa aagcaggctt cgccac                         36

<210> SEQ ID NO 10
<211> LENGTH: 51
<212> TYPE: DNA
<213> ORGANISM: Artificial Sequence
<220> FEATURE:
<223> OTHER INFORMATION: Primer evasin3 PCR2R

<400> SEQUENCE: 10
ggggaccact ttgtacaaga aagctgggtt caatggtgat ggtgatggtg a        51

<210> SEQ ID NO 11
<211> LENGTH: 20
<212> TYPE: DNA

<210> SEQ ID NO 11
<211> LENGTH: 20
<212> TYPE: DNA
<213> ORGANISM: Artificial Sequence
<220> FEATURE:
<223> OTHER INFORMATION: Primer pEAK 12F

<400> SEQUENCE: 11
gccagcttgg cacttgatgt                                          20

<210> SEQ ID NO 12
<211> LENGTH: 20
<212> TYPE: DNA
<213> ORGANISM: Artificial Sequence
<220> FEATURE:
<223> OTHER INFORMATION: Primer pEAK 12R

<400> SEQUENCE: 12
gatggaggtg gacgtgtcag                                          20

<210> SEQ ID NO 13
<211> LENGTH: 20
<212> TYPE: DNA
<213> ORGANISM: Artificial Sequence
<220> FEATURE:
<223> OTHER INFORMATION: Primer pDEST 8F

<400> SEQUENCE: 13
tcttctacgg caaggtgctg                                          20

<210> SEQ ID NO 14
<211> LENGTH: 20
<212> TYPE: DNA
<213> ORGANISM: Artificial Sequence
<220> FEATURE:
<223> OTHER INFORMATION: Primer pDEST 8R

<400> SEQUENCE: 14
aagcaagtaa aacctctaca                                          20

<210> SEQ ID NO 15
<211> LENGTH: 294
<212> TYPE: DNA
<213> ORGANISM: Artificial Sequence
<220> FEATURE:
<223> OTHER INFORMATION: cDNA allowing the expression of Evasin-3 as a
      recombinant protein fused to a Histidine tag

<400> SEQUENCE: 15
atggtgtcga tgaagacaac gcatcatgtc ctatttctgc tagttgcttt ggaatcaatg      60
cgaccctaca cgactgctct tgtttcaact attgagtcaa gaacgagtgg agatggcgca     120
gataactttg atgtagtatc ttgtaataag aattgcactt caggtcaaaa cgaatgccct     180
gaaggctgtt tttgcggctt gttgggccag aacaaaaaag gtcattgcta caaaattata     240
gggaaccttt ctggagaacc accagttgta aggcgtcacc atcaccatca ccat           294

<210> SEQ ID NO 16
<211> LENGTH: 20
<212> TYPE: DNA
<213> ORGANISM: Artificial Sequence
<220> FEATURE:
<223> OTHER INFORMATION: T7 Primer

<400> SEQUENCE: 16
taatacgact cactataggg                                          20

<210> SEQ ID NO 17

```
<211> LENGTH: 98
<212> TYPE: PRT
<213> ORGANISM: Artificial Sequence
<220> FEATURE:
<223> OTHER INFORMATION: Evasin-3-His

<400> SEQUENCE: 17

Met Val Ser Met Lys Thr Thr His His Val Leu Phe Leu Leu Val Ala
1               5                   10                  15

Leu Glu Ser Met Arg Pro Tyr Thr Thr Ala Leu Val Ser Thr Ile Glu
            20                  25                  30

Ser Arg Thr Ser Gly Asp Gly Ala Asp Asn Phe Asp Val Val Ser Cys
        35                  40                  45

Asn Lys Asn Cys Thr Ser Gly Gln Asn Glu Cys Pro Glu Gly Cys Phe
    50                  55                  60

Cys Gly Leu Leu Gly Gln Asn Lys Lys Gly His Cys Tyr Lys Ile Ile
65                  70                  75                  80

Gly Asn Leu Ser Gly Glu Pro Pro Val Val Arg Arg His His His His
                85                  90                  95

His His

<210> SEQ ID NO 18
<211> LENGTH: 72
<212> TYPE: PRT
<213> ORGANISM: Artificial Sequence
<220> FEATURE:
<223> OTHER INFORMATION: Mature Evasin-3-His

<400> SEQUENCE: 18

Leu Val Ser Thr Ile Glu Ser Arg Thr Ser Gly Asp Gly Ala Asp Asn
1               5                   10                  15

Phe Asp Val Val Ser Cys Asn Lys Asn Cys Thr Ser Gly Gln Asn Glu
            20                  25                  30

Cys Pro Glu Gly Cys Phe Cys Gly Leu Leu Gly Gln Asn Lys Lys Gly
        35                  40                  45

His Cys Tyr Lys Ile Ile Gly Asn Leu Ser Gly Glu Pro Pro Val Val
    50                  55                  60

Arg Arg His His His His His His
65                  70

<210> SEQ ID NO 19
<211> LENGTH: 50
<212> TYPE: DNA
<213> ORGANISM: Artificial Sequence
<220> FEATURE:
<223> OTHER INFORMATION: Primer evasin 3-6His F

<400> SEQUENCE: 19
accagttgta aggcgtcacc atcaccatca ccattaagga gatgacctac           50

<210> SEQ ID NO 20
<211> LENGTH: 50
<212> TYPE: DNA
<213> ORGANISM: Artificial Sequence
<220> FEATURE:
<223> OTHER INFORMATION: Primer evasin 3-6His R

<400> SEQUENCE: 20
taggtcatct ccttaatggt gatggtgatg gtgacgcctt acaactggtg           50

<210> SEQ ID NO 21
```

```
<211> LENGTH: 29
<212> TYPE: DNA
<213> ORGANISM: Artificial Sequence
<220> FEATURE:
<223> OTHER INFORMATION: Primer 5' NdeI-eva3 e.coli

<400> SEQUENCE: 21
ggaattccat atgcttgttt caactattg                                    29

<210> SEQ ID NO 22
<211> LENGTH: 35
<212> TYPE: DNA
<213> ORGANISM: Artificial Sequence
<220> FEATURE:
<223> OTHER INFORMATION: Primer 3' XhoI-eva3_e.coli

<400> SEQUENCE: 22
cgctcgagtt attaacgcct tacaactggt ggttc                             35

<210> SEQ ID NO 23
<211> LENGTH: 20
<212> TYPE: DNA
<213> ORGANISM: Artificial Sequence
<220> FEATURE:
<223> OTHER INFORMATION: T7 primer

<400> SEQUENCE: 23
taatacgact cactataggg                                              20

<210> SEQ ID NO 24
<211> LENGTH: 21
<212> TYPE: DNA
<213> ORGANISM: Artificial Sequence
<220> FEATURE:
<223> OTHER INFORMATION: pRSET-R primer

<400> SEQUENCE: 24
tggcagcagc caactcagct t                                            21

<210> SEQ ID NO 25
<211> LENGTH: 203
<212> TYPE: DNA
<213> ORGANISM: E.coli

<400> SEQUENCE: 25
atgcttgttt caactattga gtcaagaacg agtggagatg gcgcagataa ctttgatgta    60
gtatcttgta ataagaattg cacttcaggt caaaacgaat gccctgaagg ctgttttgc    120 ggcttgttgg gccagaacaa aaaaggtcat tgctacaaaa ttatagggaa cctttctgga   180
gaaccaccag ttgtaaggcg tta                                          203

<210> SEQ ID NO 26
<211> LENGTH: 67
<212> TYPE: PRT
<213> ORGANISM: E.coli

<400> SEQUENCE: 26

Met Leu Val Ser Thr Ile Glu Ser Arg Thr Ser Gly Asp Gly Ala Asp
1               5                   10                  15

Asn Phe Asp Val Val Ser Cys Asn Lys Asn Cys Thr Ser Gly Gln Asn
            20                  25                  30

Glu Cys Pro Glu Gly Cys Phe Cys Gly Leu Leu Gly Gln Asn Lys Lys
        35                  40                  45
```

```
-continued

Gly His Cys Tyr Lys Ile Ile Gly Asn Leu Ser Gly Glu Pro Pro Val
    50                  55                  60

Val Arg Arg
65

<210> SEQ ID NO 27
<211> LENGTH: 10
<212> TYPE: PRT
<213> ORGANISM: Rhipicephalus sanguineus

<400> SEQUENCE: 27

Leu Val Ser Thr Ile Glu Ser Arg Thr Ser
1               5                   10

<210> SEQ ID NO 28
<211> LENGTH: 10
<212> TYPE: PRT
<213> ORGANISM: Rhipicephalus sanguineus

<400> SEQUENCE: 28

Val Ser Thr Ile Glu Ser Arg Thr Ser Ala
1               5                   10
```